(12) United States Patent
Campbell et al.

(10) Patent No.: US 9,415,193 B2
(45) Date of Patent: *Aug. 16, 2016

(54) ELUTING MEDICAL DEVICES

(75) Inventors: Carey V. Campbell, Flagstaff, AZ (US);
Robert L. Cleek, Flagstaff, AZ (US);
Daniel L. Crandall, Flagstaff, AZ (US);
James F. Davidson, Flagstaff, AZ (US);
Paul D. Drumheller, Flagstaff, AZ (US);
Cody L. Hartman, Flagstaff, AZ (US);
Theresa A. Holland, Flagstaff, AZ (US);
Thane L. Kranzler, Flagstaff, AZ (US);
Mei Li, Flagstaff, AZ (US); Gregory LoStracco, Flagstaff, AZ (US); Bruce M. Steinhaus, Flagstaff, AZ (US);
Benjamin M. Trapp, Flagstaff, AZ (US); Thomas G. Triebes, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/603,296

(22) Filed: Sep. 4, 2012

(65) Prior Publication Data

US 2013/0253426 A1    Sep. 26, 2013

Related U.S. Application Data

(63) Continuation-in-part of application No. 13/409,843, filed on Mar. 1, 2012, now abandoned.

(60) Provisional application No. 61/560,659, filed on Nov. 16, 2011.

(51) Int. Cl.
*A61M 25/10*    (2013.01)
*A61L 29/08*    (2006.01)
*A61L 29/16*    (2006.01)

(52) U.S. Cl.
CPC .............. *A61M 25/10* (2013.01); *A61L 29/085* (2013.01); *A61L 29/16* (2013.01); *A61L 2300/602* (2013.01); *A61M 2025/105* (2013.01); *A61M 2025/1081* (2013.01)

(58) Field of Classification Search
CPC .......... A61M 25/10; A61M 2025/105; A61M 2025/1081; A61L 29/085; A61L 29/16; A61L 2300/602
USPC ................. 604/93.01, 96.01, 103.01, 103.02, 604/103.05, 103.08
See application file for complete search history.

(56) References Cited

U.S. PATENT DOCUMENTS 4,193,138 A    3/1980  Okita
5,066,298 A    11/1991 Hess (Continued)

FOREIGN PATENT DOCUMENTS

CN    101795630    8/2010
EP    0565604      7/1999

(Continued)

OTHER PUBLICATIONS

Salzmann, et al. Effects of balloon dilation on ePTFE structural characteristics. J Biomed Mater Res Sep. 15, 1997; 36(4):498-507.

(Continued)

*Primary Examiner* — Theodore Stigell
(74) *Attorney, Agent, or Firm* — Kilpatrick Townsend & Stockton, LLP

(57) ABSTRACT

The invention is directed to eluting medical devices that enable consistent "on-demand" delivery of therapeutic agents to a vessel. The medical device of the current invention comprises an expandable member, a hydrophilic coating comprising at least one therapeutic agent about the expandable member or structural layer and an outer sheath with a variably permeable microstructure. The design and methods disclosed herein ensures that therapeutic agent delivery occurs essentially only during expansion of the expandable member, minimizing coating and/or therapeutic agent loss to the bloodstream and providing controlled delivery to the treatment site.

27 Claims, 33 Drawing Sheets

(56) References Cited

U.S. PATENT DOCUMENTS

| | | | |
|---|---|---|---|
| 5,269,755 A * | 12/1993 | Bodicky | 604/523 |
| 5,318,531 A | 6/1994 | Leone | |
| 5,458,568 A | 10/1995 | Racchini et al. | |
| 5,478,349 A | 12/1995 | Nicholas | |
| 5,609,629 A | 3/1997 | Fearnot et al. | |
| 5,616,119 A | 4/1997 | Davis | |
| 5,773,019 A | 6/1998 | Ashton et al. | |
| 5,868,704 A | 2/1999 | Campbell et al. | |
| 5,893,840 A | 4/1999 | Hull et al. | |
| 5,902,745 A | 5/1999 | Butler et al. | |
| 5,954,706 A | 9/1999 | Sahatjian | |
| 6,001,386 A | 12/1999 | Ashton et al. | |
| 6,096,070 A | 8/2000 | Ragheb et al. | |
| 6,280,411 B1 | 8/2001 | Lennox | |
| 6,306,166 B1 | 10/2001 | Barry et al. | |
| 6,395,208 B1 | 5/2002 | Herweck et al. | |
| 6,450,989 B2 | 9/2002 | Dubrul et al. | |
| 6,524,274 B1 | 2/2003 | Rosenthal et al. | |
| 6,544,222 B1 | 4/2003 | Yang | |
| 6,716,444 B1 | 4/2004 | Castro | |
| 6,733,474 B2 | 5/2004 | Kusleika | |
| 6,753,071 B1 | 6/2004 | Pacetti | |
| 6,939,320 B2 | 9/2005 | Lennox | |
| 6,939,374 B2 | 9/2005 | Banik et al. | |
| 6,955,661 B1 | 10/2005 | Herweck et al. | |
| 7,020,529 B2 | 3/2006 | Krall et al. | |
| 7,066,904 B2 | 6/2006 | Rosenthal et al. | |
| 7,179,251 B2 | 2/2007 | Palasis | |
| 7,572,245 B2 | 8/2009 | Herweck et al. | |
| 7,740,793 B2 | 6/2010 | Herweck et al. | |
| 7,811,622 B2 | 10/2010 | Bates et al. | |
| 7,875,284 B2 | 1/2011 | Reyes et al. | |
| 7,892,201 B1 | 2/2011 | Laguna et al. | |
| 7,919,108 B2 | 4/2011 | Reyes et al. | |
| 7,947,015 B2 | 5/2011 | Herweck et al. | |
| 8,114,049 B2 | 2/2012 | Freyman et al. | |
| 8,162,880 B2 | 4/2012 | Jayaraman | |
| 8,177,743 B2 | 5/2012 | Lennox | |
| 2004/0236279 A1 * | 11/2004 | Herweck | A61M 25/10 604/103.01 |
| 2005/0182361 A1 * | 8/2005 | Lennox | 604/103.01 |
| 2008/0015500 A1 | 1/2008 | Herweck et al. | |
| 2008/0021385 A1 | 1/2008 | Barry et al. | |
| 2008/0118544 A1 | 5/2008 | Wang | |
| 2009/0226502 A1 | 9/2009 | Chen | |
| 2009/0227948 A1 | 9/2009 | Chen et al. | |
| 2009/0227949 A1 | 9/2009 | Knapp et al. | |
| 2009/0287182 A1 | 11/2009 | Bishop et al. | |
| 2010/0021519 A1 | 1/2010 | Shenoy | |
| 2010/0042199 A1 | 2/2010 | Burton | |
| 2010/0049225 A1 * | 2/2010 | To et al. | 606/159 |
| 2011/0015725 A1 | 1/2011 | Bates et al. | |
| 2011/0054396 A1 | 3/2011 | Kangas et al. | |
| 2011/0190863 A1 | 8/2011 | Ostroot et al. | |
| 2011/0196340 A1 | 8/2011 | Barry et al. | |
| 2011/0251582 A1 | 10/2011 | Lennox | |
| 2011/0270226 A1 | 11/2011 | Kocur et al. | |
| 2011/0301565 A1 | 12/2011 | Weber | |
| 2012/0053517 A1 | 3/2012 | Chen et al. | |
| 2013/0103062 A1 | 4/2013 | To et al. | |

FOREIGN PATENT DOCUMENTS

| | | |
|---|---|---|
| EP | 0708671 | 11/2001 |
| EP | 0747069 | 9/2002 |
| EP | 0863729 | 12/2004 |
| EP | 0920843 | 2/2005 |
| EP | 1263492 | 4/2005 |
| EP | 0836429 | 11/2005 |
| EP | 1148899 | 4/2006 |
| EP | 1351739 | 5/2006 |
| EP | 1800702 | 6/2007 |
| EP | 1011743 | 7/2011 |
| EP | 2043704 | 8/2011 |
| WO | 96/40305 | 12/1996 |
| WO | 01/64278 | 9/2001 |
| WO | 03/015677 | 2/2003 |
| WO | 2008/064058 | 5/2008 |
| WO | 2010/093800 | 8/2010 |
| WO | 2013/074185 | 5/2013 |

OTHER PUBLICATIONS

International Search Report for PCT/US2013/058171 mailed Dec. 16, 2013, corresponding to U.S. Appl. No. 14/018,053, 4 pages.

International Search Report for PCT/US2013/058242 mailed Dec. 19, 2013, corresponding to U.S. Appl. No. 14/018,202, 4 pages.

* cited by examiner

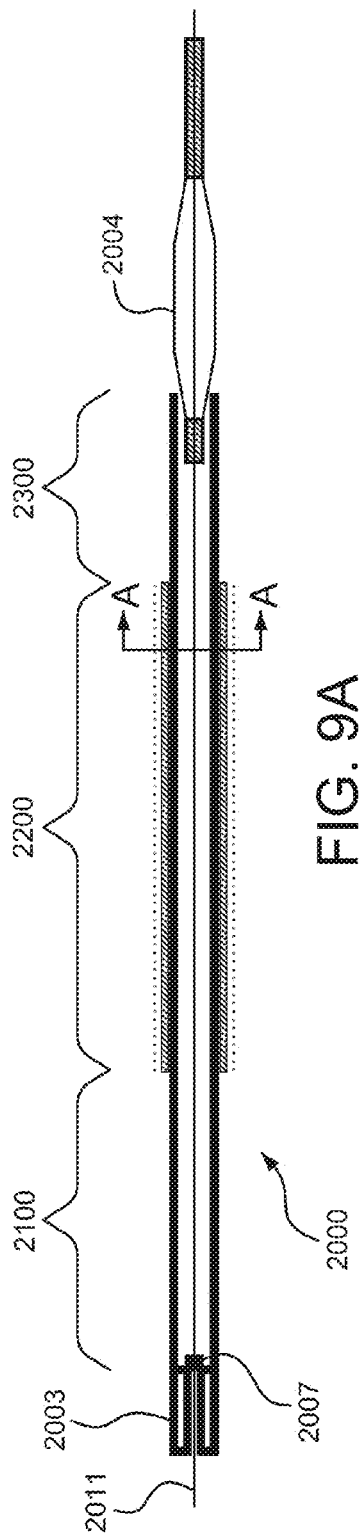
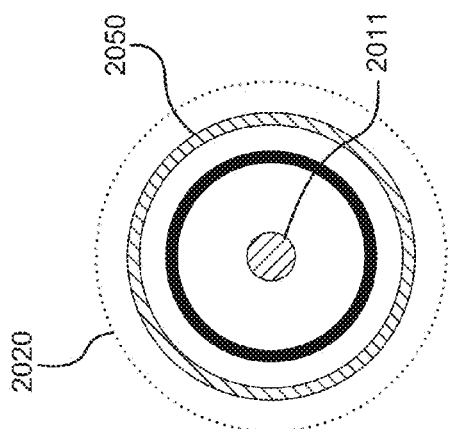
FIG. 9A
FIG. 9B

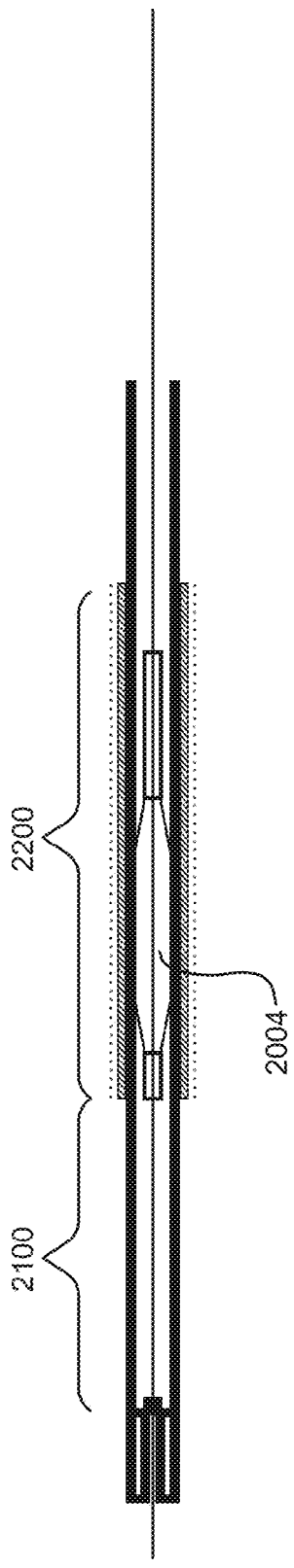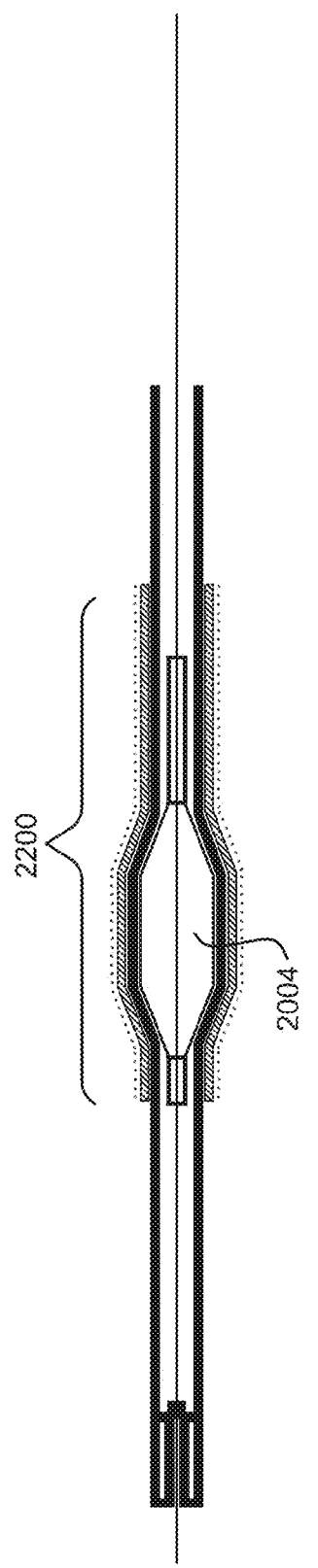

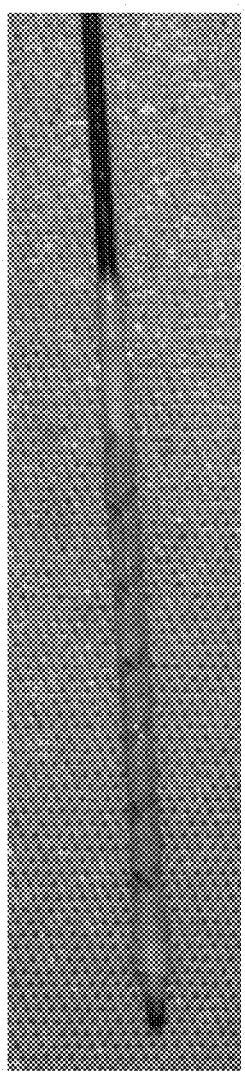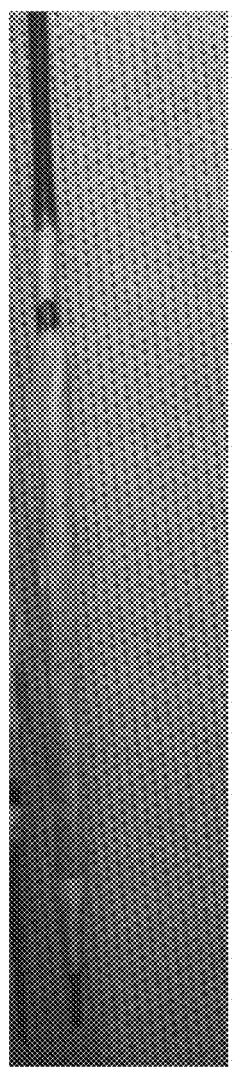
FIG. 11A
FIG. 11B

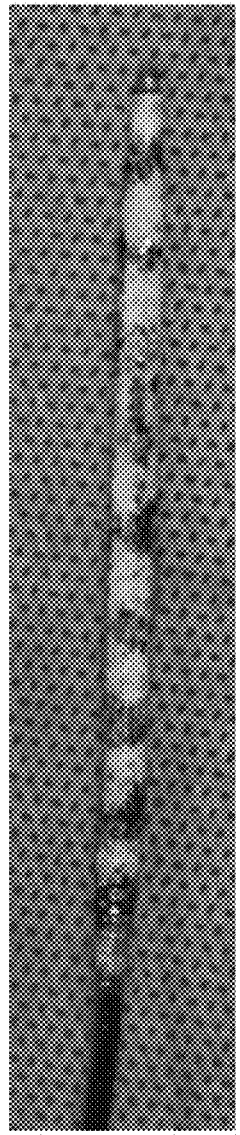
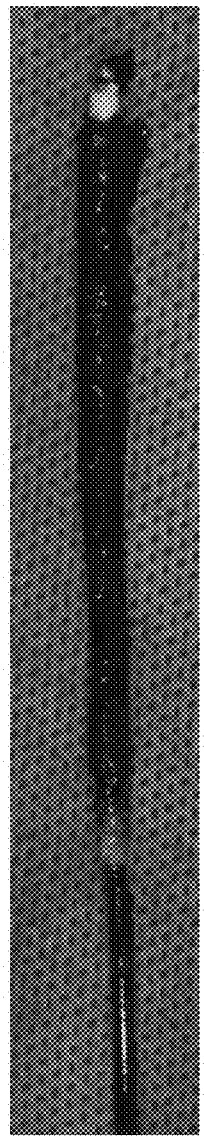
FIG. 19A
FIG. 19B

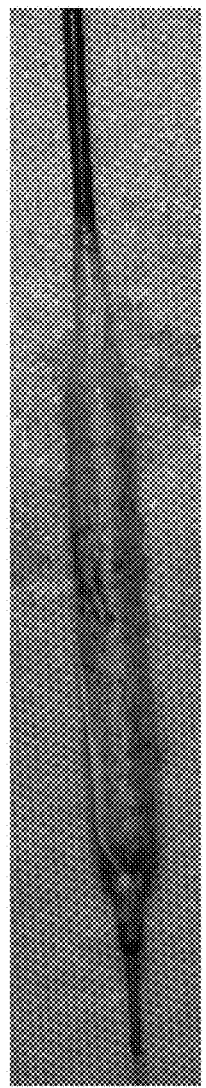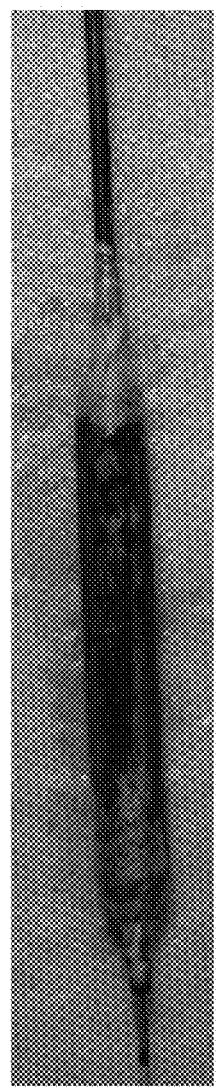

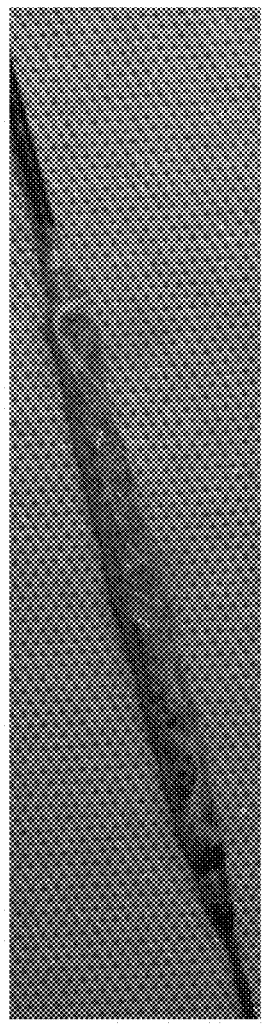 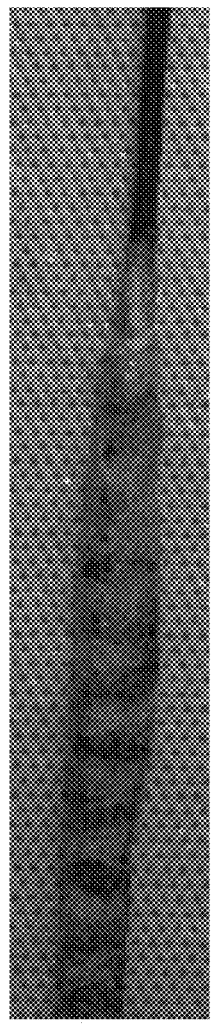 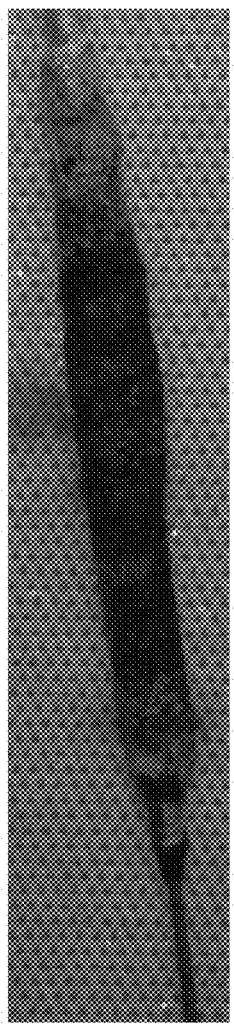

ELUTING MEDICAL DEVICES

CROSS-REFERENCE TO RELATED APPLICATIONS

This application is a Continuation in Part of U.S. patent application Ser. No. 13/409,843 filed on Mar. 1, 2012, which claims priority to U.S. Provisional Application No. 61/449,427 filed on Mar. 4, 2011 and U.S. Provisional Application No. 61/560,659 filed on Nov. 16, 2011, all of which are incorporated by reference herein in their entireties.

BACKGROUND

The systemic administration of therapeutic agents treats the body as a whole even though the disease to be treated may be localized. In some cases of localized disease, systemic administration may not be desirable because the drug agents may have unwanted effects on parts of the body which are not to be treated or because treatment of the diseased part of the body requires a high concentration of a drug agent that may not be achievable by systemic administration.

It is therefore often desirable to administer therapeutic agents to only localized sites within the body. Common examples of where this is needed include cases of localized disease (e.g., coronary heart disease) and occlusions, lesions, or other disease in body lumens. Several devices and methods for localized drug delivery are known. In one example, such devices are drug delivery balloons, and methods of their use include the steps of coating a balloon attached to a balloon catheter with a drug and a carrier matrix, inserting the catheter into a blood vessel, tracking the balloon to a desired location, and expanding the balloon against the surrounding tissue to transfer the drug locally at the intended treatment site.

One of the potential drawbacks to localized drug delivery is the possibility of premature or unintended release of the drug, the carrier matrix, and/or the drug/carrier matrix combination. This may occur during tracking and placement at the treatment site of a drug delivery device and post delivery as the device is withdrawn from the body. Such unintended release may result from drug diffusion, device contact with areas proximate the treatment site, or washing of the drug from the surface of the delivery device due to blood flow. This is of particular concern when the device comprises a therapeutic agent of a type or dosage not intended to be released to tissue or blood outside the treatment site.

Drugs or coating components shed in this unwanted fashion may be in particulate form or may be in solution. The release of undesirable particles is known as "particulation". Particulation of large particles can create problems such as ischemia in tissues, especially in tissues supplied by small diameter vessels. Furthermore, the resulting effects of biodistribution of such particles are not well understood and may result in adverse effects.

When combining a drug with an implantable device, the drug may be in a solid form (as a particulate or crystal) but is preferably released from the device as a solubilized molecule. The advantages of localized, solubilized drug delivery are believed to be uniform drug distribution at the treatment site, well-known drug biodistribution, and the avoidance of particulation.

In view of the potential drawbacks to current, localized drug delivery, there exists a need for devices and methods that allow for controlled, localized delivery of drug agents, especially soluble agents, to specific treatment sites within a mammalian body that avoids particulation and premature or unintended drug release away from the intended treatment site, while ensuring that desired dosing occurs.

SUMMARY

The invention is directed to an expandable medical device that delivers a therapeutic agent to a vessel or other lumen of cavity that enables consistent "on-demand" delivery of the agent, while not substantially eluting or releasing said therapeutic agent as the device is being tracked to the desired treatment site. The medical device of the current invention comprises an expandable member with or without a structural layer serving as a substrate over said expandable member, at least one hydrophilic coating comprising at least one therapeutic agent on the expandable member or structural layer, and an outer sheath comprising a variably permeable microstructure. During use, the underlying hydrophilic coating becomes hydrated or partially hydrated and facilitates fluid transfer across the outer sheath. However, said outer sheath's closed microstructure in the unexpanded state prevents unwanted, premature release of said therapeutic agent. Upon expansion, the outer sheath disposed over the expandable member or structural layer transforms from a closed microstructure to an open microstructure allowing the hydrated or partially hydrated coating and said therapeutic agent to be transferred (e.g. pushed) outward. Once the hydrated or partially hydrated hydrophilic coating passes through the sheath, the therapeutic agent is delivered to the treatment site. In another embodiment, the hydrated or partially hydrated coating comprises a soluble therapeutic agent and once the outer sheath is expanded, the therapeutic agent is transferred through the sheath. In another embodiment, said expandable member is a medical balloon.

In another embodiment, the invention comprises a medical device comprising an expandable member, a coating comprising a therapeutic agent disposed around said expandable member, a sheath disposed around said coating, wherein said sheath has a variably permeable microstructure that initially prevents or limits unintended transfer of therapeutic agent through said sheath, wherein said coating and therapeutic agent are disposed between the surface of the expandable member and the sheath, and wherein when said expandable member and sheath are expanded, said sheath allows rapid transfer of said coating and therapeutic agent to an area external to said sheath when said sheath is in an unexpanded state while preventing transfer of particles out of said sheath greater than about 25 microns in size. For example, the maximum effective pore size of the microstructure at second diameter is less than or equal to about 25 microns. In other embodiments, particles greater than about 25 microns in size can transfer through said sheath. In one embodiment, said expandable member is a medical balloon. In another embodiment, said medical device comprises a catheter. In another embodiment, said sheath allows rapid transfer of said coating and therapeutic agent because said sheath rapidly wets out during expansion. In another embodiment, said sheath undergoes only microscopic wetting in a vessel while said balloon and sheath are in the unexpanded state and being tracked to a desired location within a vessel. In another embodiment, bodily fluids substantially wet-out the sheath when said sheath is expanded. In another embodiment, said sheath is modified to include a hydrophilic component located within at least a part of the sheath and/or on part or all of said sheath's external surface. In another embodiment, said hydrophilic component of said sheath also wets the sheath before and as said sheath is expanded. In another embodiment, substantially all of said sheath is wet by the time said sheath is fully expanded (i.e., expanded to its rated or nominal diameter). In another embodiment, fluid external to said sheath is allowed to flow through said sheath and contact said therapeutic agent before and as said sheath is expanded. In another embodiment, said wetting of the sheath is facilitated when said sheath is in contact with the vessel wall. In another embodiment, said sheath comprises a fluoropolymer. In another embodiment, the outer sheath is wet-out by a prescribed preparatory procedure prior to being inserted into the patient. In another embodiment, said sheath comprises a microstructure comprised of nodes interconnected by fibrils. In another embodiment, said nodes are aligned longitudinally to the longitudinal axis of said balloon catheter and said fibrils are aligned circumferentially to said axis. In another embodiment, said nodes are aligned circumferentially to the longitudinal axis of said balloon catheter and said fibrils are aligned longitudinally to said axis. In another embodiment, the distance between said fibrils increases as said outer sheath expands. In another embodiment, the distance between said nodes increases as said outer sheath expands. In another embodiment, the orientation of said nodes and/or fibrils changes as said outer sheath expands. In another embodiment, said sheath comprises expanded polymers, such as polytetrafluoroethylene (ePTFE). In another embodiment, said coating comprises a hydrophilic component. In another embodiment, said therapeutic agent is a hydrophilic agent. In another embodiment, said coating comprises at least one compound selected from the group consisting of benzethonium chloride, poloxamer-188, polyethylene glycol, calcium salicylate, and hydroxypropyl-β-cyclodextrin. In another embodiment, said therapeutic agent is a hydrophobic agent. In another embodiment, said therapeutic agent is paclitaxel. In another embodiment, said expandable member further comprises a structural layer. In another embodiment, said structural layer comprises said coating and therapeutic agent. In another embodiment, the microstructure of the outer sheath changes as said expandable member expands.

In another embodiment, the invention comprises a medical device comprising: an expandable member; a coating comprising a therapeutic agent disposed around said expandable member a sheath having an inner surface and an outer surface wherein said sheath comprises a variably permeable microstructure that initially limits unintended transfer of said therapeutic agent through said sheath when said sheath has a substantially closed microstructure; wherein said coating is disposed on the inner surface of said sheath; and wherein when said expandable member and sheath are expanded, said sheath has an open microstructure and allows the transfer of said therapeutic agent to an area external to said sheath. In various embodiments, the sheath can prevent transfer of particles out of said sheath greater than about 25 microns in size. For example, the maximum effective pore size of the microstructure at second diameter is less than or equal to about 25 microns. In other embodiments, particles greater than about 25 microns in size can transfer through said sheath. In one embodiment, said expandable member is a medical balloon. In another embodiment, said medical device comprises a catheter. In another embodiment, said sheath allows rapid transfer of said coating and therapeutic agent because said sheath rapidly wets out just prior to and/or during expansion. In another embodiment, said sheath undergoes only microscopic wetting in a vessel while said balloon and sheath are in the unexpanded state and being tracked to a desired location within a vessel. In another embodiment, bodily fluids substantially wet-out the sheath when said sheath is expanded. In another embodiment, said sheath is modified to include a hydrophilic component located within at least a part of the sheath and/or on part or all of said sheath's external surface. In another embodiment, said hydrophilic component of said sheath aids wetting of the sheath before and as said sheath is expanded. In another embodiment, substantially all of said sheath is wetted by the time said sheath is fully expanded (i.e., expanded to its rated or nominal diameter). In another embodiment, fluid external to said sheath is allowed to flow through said sheath and contact said therapeutic agent before and as said sheath is expanded. In another embodiment, said wetting of the sheath is facilitated when said sheath is in contact with the vessel wall. In another embodiment, said sheath comprises a fluoropolymer. In another embodiment, the outer sheath is wet-out by a prescribed preparatory procedure prior to being inserted into the patient. In another embodiment, said sheath comprises a microstructure comprised of nodes interconnected by fibrils. In another embodiment, said nodes are aligned longitudinally to the longitudinal axis of said balloon catheter and said fibrils are aligned circumferentially to said axis. In another embodiment, said nodes are aligned circumferentially to the longitudinal axis of said balloon catheter and said fibrils are aligned longitudinally to said axis. In another embodiment, the distance between said fibrils increases as said outer sheath expands. In another embodiment, the distance between said nodes increases as said outer sheath expands. In another embodiment, the orientation, size, or conformation of said nodes and/or fibrils changes as said outer sheath expands. In another embodiment, said sheath comprises an expanded polymer, such as expanded polytetrafluoroethylene (ePTFE). In another embodiment, said coating comprises a hydrophilic component. In another embodiment, said therapeutic agent is a hydrophilic agent. In another embodiment, said coating comprises at least one compound selected from the group consisting of benzethonium chloride, poloxamer-188, polyethylene glycol, sodium salicylate, and hydroxypropyl-β-cyclodextrin. In another embodiment, said therapeutic agent is a hydrophobic agent. In another embodiment, said therapeutic agent comprises paclitaxel. In another embodiment, said expandable member further comprises a structural layer. In another embodiment, said structural layer comprises said coating and therapeutic agent. In another embodiment, the microstructure of the outer sheath changes as said expandable member expands. In constructing the above embodiment, a coating can be applied to the outer surface of the sheath. Once applied, the sheath can be everted so that the outer surface becomes the inner surface and is disposed about the expandable member.

Another embodiment of the invention comprises a balloon catheter comprising, a balloon comprising a coating and a therapeutic agent disposed around the outer surface of said balloon, a sheath disposed around said balloon wherein said sheath has a microstructure composed of nodes interconnected by fibrils and has characteristics which prevent macroscopic wetting of said sheath in the unexpanded state, wherein said coating and therapeutic agent are disposed between the surface of the balloon and the sheath, and wherein when said balloon and sheath are expanded, substantially all of said sheath wets out rapidly and allows rapid transfer of said coating through the outer sheath. In one embodiment, said coating is transferred through said outer sheath and onto or into a target tissue. In one embodiment, upon expansion said coating is transferred through said outer sheath in a hydrated or partially hydrated state. In another embodiment, said coating remains substantially adhered to the target tissue for greater than 1 minute after contact between balloon and treatment site is substantially eliminated. In another embodiment, said sheath undergoes microscopic wetting in a vessel while said balloon and sheath are in the unexpanded state and being delivered to a desired location within a vessel. In another embodiment, bodily fluids substantially wet-out the sheath when said sheath is expanded. In another embodiment, said coating also wets the sheath when said sheath is expanded. In another embodiment, substantially all of said sheath is wet by the time said sheath is fully expanded. In another embodiment, said wetting of the sheath is facilitated when said sheath is in contact with a vessel wall. In another embodiment, said sheath comprises a fluoropolymer. In another embodiment, said nodes are aligned longitudinally to the longitudinal axis of said balloon catheter and said fibrils are aligned circumferentially to said axis. In another embodiment, said nodes are aligned circumferentially to the longitudinal axis of said balloon catheter and said fibrils are aligned longitudinally to said axis. In another embodiment, said nodes are spread apart as said outer sheath expands, i.e., the distance between said nodes increase. In another embodiment, the distance lying between said fibrils increases as said outer sheath expands. In another embodiment, the orientation of said nodes and/or fibrils changes as said outer sheath expands. In another embodiment, said sheath comprises ePTFE. In another embodiment, said coating comprises a hydrophilic component. In another embodiment, said therapeutic agent is a hydrophilic agent. In another embodiment, said therapeutic agent is a hydrophobic agent. In another embodiment, said therapeutic agent is paclitaxel. In another embodiment, said balloon further comprises a structural layer. In another embodiment, said structural layer comprises said coating and therapeutic agent. In another embodiment, the microstructure of the sheath changes as said balloon expands.

Another embodiment of the invention comprises a balloon catheter comprising: a balloon comprising a coating and a therapeutic agent disposed around the outer surface of said balloon; a first outer sheath disposed around said coating; and a second outer sheath disposed around said first outer sheath, wherein said second sheath does not prevent macroscopic wetting of said sheath in an unexpanded state, wherein said first sheath has a microstructure composed of nodes interconnected by fibrils and has characteristics which prevent macroscopic wetting of said sheath in the unexpanded state and when said balloon and sheaths are expanded, said first sheath forms opening which expose sections of the underlying coating and allows rapid transfer of said coating through the outer sheath. In an embodiment, said first sheath is configured to split or tear to form openings. In another embodiment, said first sheath can be folded or otherwise configured onto the balloon in such a way that a plurality of openings is not exposed through the thickness until inflated. In one embodiment, said coating is transferred through said second sheath and onto or into a target tissue. In one embodiment, upon expansion said coating is transferred through said second sheath in a hydrated or partially hydrated state. In another embodiment, said coating remains substantially adhered to the target tissue for greater than 1 minute after contact between balloon and treatment site is substantially eliminated. In another embodiment, said sheaths undergo microscopic wetting in a vessel while said balloon and sheaths are in the unexpanded state and being delivered to a desired location within a vessel. In an embodiment, said transfer of the hydrated or partially hydrated coatings is facilitated when said second sheath is in contact with a vessel wall. In another embodiment, said first sheath comprises a fluoropolymer. In another embodiment, said second sheath also comprises a fluoropolymer. In another embodiment, said nodes are aligned longitudinally to the longitudinal axis of said balloon catheter and said fibrils are aligned circumferentially to said axis. In another embodiment, said nodes are aligned circumferentially to the longitudinal axis of said balloon catheter and said fibrils are aligned longitudinally to said axis. In another embodiment, said first sheath comprises ePTFE. In another embodiment, said coating comprises a hydrophilic component. In another embodiment, said therapeutic agent is a hydrophilic agent. In another embodiment, said therapeutic agent is a hydrophobic agent. In another embodiment, said therapeutic agent is paclitaxel. In another embodiment, said balloon further comprises a structural layer. In another embodiment, said structural layer comprises said coating and therapeutic agent.

In another embodiment, the invention comprises a medical device comprising an expandable member and a casing comprising a lumen disposed around said expandable member. Said casing comprises a coating located inside the lumen. The coating comprises a therapeutic agent. In an embodiment, said casing can helically wrapped around the expandable member. In another embodiment, said casing can comprise an annular shape disposed about the expandable member. In an embodiment, a casing can be longitudinally oriented. In another embodiment, a plurality of said casings can be disposed around or along the expandable member. In an embodiment, said casing has a microstructure composed of nodes interconnected by fibrils and has characteristics which prevent macroscopic wetting of said casing in the unexpanded state, wherein said coating and therapeutic agent are disposed inside the lumen of the casing, and wherein when said expandable member is expanded, substantially all of said casing wets out rapidly and allows rapid transfer of said coating through the casing. In one embodiment, said coating is transferred through said casing and onto or into a target tissue. In one embodiment, upon expansion said coating is transferred through said casing in a hydrated or partially hydrated state. In another embodiment, said coating remains substantially adhered to the target tissue for greater than 1 minute after contact between expandable member and treatment site is substantially eliminated. In another embodiment, said casing undergoes microscopic wetting in a vessel while said balloon and casing are in the unexpanded state and being delivered to a desired location within a vessel. In another embodiment, bodily fluids substantially wet-out the casing when said casing is expanded. In another embodiment, said coating also wets the casing when said casing is expanded. In another embodiment, substantially all of said casing is wet by the time said casing is fully expanded. In another embodiment, said wetting of the casing is facilitated when said casing is in contact with a vessel wall. In another embodiment, said casing comprises a fluoropolymer. In another embodiment, said nodes are aligned longitudinally to the longitudinal axis of said expandable member and said fibrils are aligned circumferentially to said axis. In another embodiment, said nodes are aligned circumferentially to the longitudinal axis of said expandable member and said fibrils are aligned longitudinally to said axis. In another embodiment, said nodes are spread apart as said casing expands, i.e., the distance between said nodes increase. In another embodiment, the distance lying between said fibrils increases as said casing expands. In another embodiment, the orientation of said nodes and/or fibrils changes as said casing expands. In another embodiment, said casing comprises ePTFE. In another embodiment, said coating comprises a hydrophilic component. In another embodiment, said therapeutic agent is a hydrophilic agent. In another embodiment, said therapeutic agent is a hydrophobic agent. In another embodiment, said therapeutic agent is paclitaxel. In another embodiment, said expandable member further comprises a structural layer. In another embodiment, said structural layer comprises said coating and therapeutic agent. In another embodiment, the microstructure of the casing changes as said expandable member expands. In another embodiment, the casing becomes strained as said expandable member expands facilitating transfer of the hydrated or partially hydrated coating through the casing.

In another embodiment, the invention comprises a medical device comprising an expandable member and a neckable casing comprising a lumen disposed around said expandable member. Said casing comprises a coating located inside the lumen. In a further embodiment, a second coating can be located in between the expandable member and the neckable casing. Both coatings can comprise a therapeutic agent, which can be the same or different. In an embodiment, said neckable casing can helically wrapped around the expandable member. In another embodiment, said casing can comprise an annular shape disposed about the expandable member. In an embodiment, a casing can be longitudinally oriented. In another embodiment, a plurality of said casings can be disposed around or along the expandable member. In an embodiment, said casing has a microstructure composed of nodes interconnected by fibrils and has characteristics which prevent macroscopic wetting of said casing in the unexpanded state and wherein when said expandable member is expanded, substantially all of said casing wets out rapidly and allows rapid transfer of said coating through the casing. In one embodiment, said coating is transferred through said casing and onto or into a target tissue. In an embodiment, the necking of the casing during expansion facilitates driving out the hydrated or partially hydrated coating through the casing. In another embodiment, upon expansion, the neckable casing reduces in cross-section to expose at least a portion of the underlying second coating to the surrounding tissue. In one embodiment, upon expansion both coatings are transferred to said tissue in a hydrated or partially hydrated state. In another embodiment, said coating remains substantially adhered to the target tissue for greater than 1 minute after contact between expandable member and treatment site is substantially eliminated. In another embodiment, said casing undergoes microscopic wetting in a vessel while said balloon and casing are in the unexpanded state and being delivered to a desired location within a vessel. In another embodiment, bodily fluids substantially wet-out the casing when said casing is expanded. In embodiment, both coatings also wet the casing when said casing is expanded. In another embodiment, substantially all of said casing is wet by the time said casing is fully expanded. In another embodiment, said wetting of the casing is facilitated when said casing is in contact with a vessel wall. In another embodiment, said casing comprises a fluoropolymer. In another embodiment, said nodes are aligned longitudinally to the longitudinal axis of said expandable member and said fibrils are aligned circumferentially to said axis. In another embodiment, said nodes are aligned circumferentially to the longitudinal axis of said expandable member and said fibrils are aligned longitudinally to said axis. In another embodiment, said nodes are spread apart as said casing expands, i.e., the distance between said nodes increase. In another embodiment, the distance lying between said fibrils increases as said casing expands. In another embodiment, the orientation of said nodes and/or fibrils changes as said casing expands. In another embodiment, said casing comprises ePTFE. In another embodiment, said coating comprises a hydrophilic component. In another embodiment, said therapeutic agent is a hydrophilic agent. In another embodiment, said therapeutic agent is a hydrophobic agent. In another embodiment, said therapeutic agent is paclitaxel. In another embodiment, said expandable member further comprises a structural layer. In another embodiment, said structural layer comprises said coating and therapeutic agent. In another embodiment, the microstructure of the casing changes as said expandable member expands. In another embodiment, the casing becomes strained as said expandable member expands facilitating transfer of the hydrated or partially hydrated coating through the casing.

Other embodiments of the invention comprise a method of delivering a therapeutic agent to a desired location within a vessel comprising, inserting a catheter in a vessel, said catheter comprising an expandable member comprising a coating with a therapeutic agent, a sheath disposed around said expandable member, wherein said sheath has a variably permeable microstructure that prevents said coating from being transported through substantially all of said sheath in the unexpanded state, and wherein said coating and therapeutic agent are disposed between the surface of the expandable member and the sheath, advancing said catheter to a desired location within said vessel, and expanding the expandable member and sheath at the desired location within said vessel, and wherein substantially all of said sheath allows transfer of said coating and therapeutic agent from between the surface of the expandable member and the sheath to an area external to said sheath when said sheath is in an unexpanded state while preventing transfer of particles out of said sheath greater than about 25 microns in size. For example, the maximum effective pore size of the microstructure at second diameter is less than or equal to about 25 microns. In other embodiments, particles greater than about 25 microns in size can transfer through said sheath. In one embodiment, said expandable member is a medical balloon. In another embodiment, said sheath allows rapid transfer of said coating and therapeutic agent because said sheath rapidly wets out during expansion. In another embodiment, said sheath undergoes microscopic wetting in a vessel while said balloon and sheath are in the unexpanded state and being delivered to a desired location within a vessel. In another embodiment, said macroscopic wetting of the sheath is facilitated when said sheath is in contact with the vessel wall. In another embodiment, said sheath comprises a fluoropolymer. In another embodiment, the sheath comprises a microstructure comprised of nodes interconnected by fibrils. In another embodiment, said nodes are aligned longitudinally to the longitudinal axis of said balloon catheter and said fibrils are aligned circumferentially to said axis. In another embodiment, said nodes are aligned circumferentially to the longitudinal axis of said balloon catheter and said fibrils are aligned longitudinally to said axis. In another embodiment, said nodes expand (elongate) said outer sheath expands. In another embodiment, said nodes are spread apart as said outer sheath expands. In another embodiment, the orientation of said nodes changes as said outer sheath expands. In another embodiment, said fibrils are spread apart as said outer sheath expands. In another embodiment, said fibrils are unfolded, straightened out or reoriented as said outer sheath expands. In another embodiment, said sheath comprises ePTFE. In another embodiment, said therapeutic agent is a hydrophilic agent. In another embodiment, said therapeutic agent is a hydrophobic agent. In another embodiment, said therapeutic agent is paclitaxel. In another embodiment, said coating is hydrophilic. In another embodiment, said expandable member further comprises a structural layer. In another embodiment, said structural layer comprises said coating and therapeutic agent. In another embodiment, the microstructure of the sheath changes as said expandable member expands. In another embodiment, the hydrated or partially hydrated hydrophilic coating containing a therapeutic agent is tissue adherent, and thus, even after the expandable member is removed from the site, the drug continues to be absorbed into the tissue until the coating and drug dissipate from the site. This approach effectively increases the total drug delivery time to the tissue.

In another embodiment of the invention, said coating contains a hydrophobic drug that is complexed or sequestered by one or more solubilizing agents. In another embodiment, said solubilizing agent helps said hydrophobic drug transfer to a target tissue. In another embodiment, said solubilizing agent, when delivered to the intended tissue site, dissociates from said drug and the drug binds to tissue.

Another embodiment of the invention comprises a balloon catheter comprising a balloon comprising a relatively low-solubility therapeutic agent in the form of micelles, liposomes, micro-aggregates, nanospheres, microspheres, nanoparticles, microparticles, crystallites, or inclusion complexes combined with or suspended in a coating material that hydrates or dissolves more rapidly than the agent; the agent and coating being disposed around the outer surface of said balloon; a sheath disposed around said balloon, wherein said coating and therapeutic agent are disposed between the surface of the balloon and the sheath, and wherein when said sheath is wetted and said coating hydrates and the form of said agent remain essentially intact, and wherein when said balloon and sheath are expanded, transfer of the hydrated coating and agent occurs through said outer sheath and onto or into a target tissue.

Another embodiment of the invention comprises a sheath disposed around a coating disposed about an expandable member where the sheath is purposefully under- or over-sized in diameter to further modulate fluid transfer through the outer sheath.

Another embodiment of the invention comprises a sheath disposed around a coating disposed about an expandable member wherein the sheath is purposefully modified with a wetting agent to facilitate wetting of said sheath in the unexpanded state. However, said modified sheath, even when wet-out, prevents drug transfer across said sheath in the unexpanded state.

In another embodiment, an expandable device such as a stent or stent-graft may be mounted to the "on-demand" agent elution construct of the invention, delivered to a site within the body where the expandable device is expanded and placed using the construct of the invention. The advantage of this application is that a therapeutic can be delivered to a treatment site along with another treatment device.

In another embodiment, following therapeutic treatment with the "on-demand" agent elution construct of the invention, an expandable device such as a stent, stent-graft, or other endoprosthesis may be placed in the treatment region, and the construct of the invention is used to "touch-up" or otherwise modify the degree to which at least a portion of the device is expanded.

In another embodiment, placement and/or "touching up" of an endoprosthesis with therapeutic agent elution constructs of the instant invention may comprise transferring a therapeutic agent from the construct to the endoprosthesis (e.g., by absorptive transfer), whereby the endoprosthesis subsequently becomes a drug eluting endoprosthesis which operates therapeutically over short or long periods of time.

BRIEF DESCRIPTION OF THE DRAWINGS

The exemplary embodiments of the present invention will be described in conjunction with the accompanying drawings. The accompanying drawings are included to provide a further understanding of the invention and are incorporated in and constitute a part of this specification, illustrate embodiments of the invention and together with the description serve to explain the principles of the invention. Figures are not drawn to scale.

FIGS. 3A and 3B are SEMs of sheath 1, while FIGS. 3C and 3D are SEMS of sheath 2. FIGS. 3A and 3C respectively show sheath 1 and sheath 2 in their first state with a closed microstructure, and FIGS. 3B and 3D respectively show sheath 1 and sheath 2 in their second state with an open microstructure.

FIG. 9A depicts a catheter construct that can be used to deliver therapeutic agents. FIG. 9B depicts a cross-section of the catheter construct of FIG. 9A. FIGS. 9C through 9F depict a method of using the catheter construct of FIG. 9A.

FIG. 10C depicts a cross-section of the sleeve. FIGS. 9D to 9G depict a method of using a drug eluting sleeve embodiment.

FIGS. 11A and 11B depict degree of wetting of a device with a hydrophilic coating (Device 8a, FIG. 11A) and a device without a coating (Device 8b, FIG. 11B) after being submerged in blood in an unexpanded state.

FIG. 18A depicts a light micrograph of a histological cross-section of the Control Artery of Example 12. FIG. 18B shows a fluorescence micrograph of a histological cross-section of the Control Artery shown in FIG. 18A. FIG. 18C depicts a light micrograph of a histological cross section of the Test Artery of Example 12 after contact with a construct of the invention comprising Texas Red-labeled dextran. FIG. 18D shows a fluorescence micrograph of a histological cross-section of the Test Artery shown in FIG. 18C.

FIGS. 19A and 19B show degree of wetting of Device 13 after in vivo incubation in canine arteries in unexpanded (FIG. 19A) and expanded (FIG. 19B) states.

FIG. 20A depicts a light micrograph of a histological cross-section of the Control Iliac Artery of Example 13. FIG. 20B shows a fluorescence micrograph of a histological cross-section of the Control Iliac Artery shown in FIG. 20A. FIG. 20C depicts a light micrograph of a histological cross section of the Test Iliac Artery of Example 13 after contact with a construct of the invention comprising Texas Red-labeled dextran. FIG. 20D shows a fluorescence micrograph of a histological cross-section of the Test Iliac Artery shown in FIG. 20C.

FIG. 21 shows Device 14 of Example 14 after expansion to 6 atm (FIG. 21A) and 12 atm (FIG. 21B) in blood in a rigid tube without prehydration in blood.

FIGS. 24A, 24B, and 24C show the degree of wetting of Device 16 when uninflated (FIG. 24A), inflated to 6 atm in a rigid tube in blood (FIG. 24B), and inflated to 12 atm in a rigid tube in blood (FIG. 24C).

DETAILED DESCRIPTION OF THE EMBODIMENTS

Certain embodiments of the invention are directed to a catheter comprising an agent eluting construct for delivery of at least one therapeutic agent to a desired site within a mammalian body. The therapeutic agent elution construct of the instant invention comprises additional structures which ensure drug delivery to the target site without significant drug loss during device tracking to the target site and without particulation of the agent. In one embodiment, said agent elution construct comprises an expandable member. In another embodiment, said expandable member is a medical balloon. (As used herein balloon and medical balloon are used interchangeably, unless otherwise noted).

For clarity, the figures, the description and the examples describe and depict an agent elution construct comprising a medical balloon. However, the invention is not intentioned to be limited to this one embodiment. As described below, other expandable members are envisioned as part of this invention.

Reference will now be made in detail to embodiments of the present invention, examples of which are illustrated in the accompanying drawings.

Figure 1:
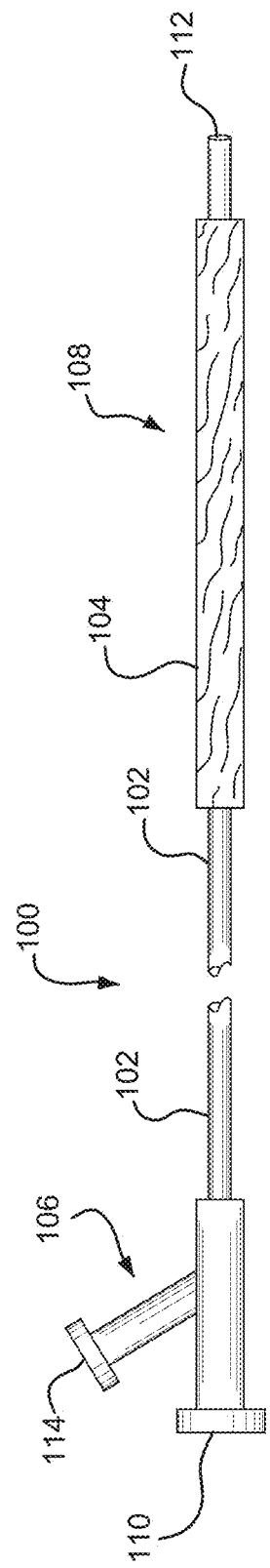
FIG. 1 depicts a general balloon catheter having an elongated tubular body with a balloon.

FIG. 1 is illustrative of a balloon catheter 100 having an elongated tubular body 102 with a balloon 104. In one embodiment, balloon 104 can be a length adjustable balloon. Length adjustable balloons can comprise constructs known in the art. In an embodiment, an evertable balloon can be used to adjust the length.

The elongated tubular body 102 has a proximal control end 106 and a distal functional end 108. The balloon catheter also has a proximal guidewire lumen 110 that extends through the length of the elongated tubular body 102 and exits the distal end at a guidewire port 112. The balloon catheter shown is an "Over The Wire" configuration, as commonly known in the art. Alternatively, the catheter could have a guidewire port located midway between proximal and distal ends and therefore have a "Rapid Exchange" configuration, as commonly known in the art. The balloon catheter 100 also incorporates a proximal inflation port 114 that allows fluid communication between the inflation port 114 and the lumen of the balloon 104. The length and inner and outer diameter of the tubular body are selected based upon the desired application of the medical device. The tubular body generally has a circular cross-sectional configuration. However, oval and other cross-sectional configurations can also be used. In one embodiment, said balloon catheter is compatible with 0.038", 0.035", 0.018" or 0.014", 0.010", or similar conventional guidewires.

The tubular body must have sufficient structural integrity to permit the medical device to be advanced to distal vascular locations without bending or buckling upon insertion. Various techniques are known for manufacturing the tubular bodies. In one embodiment, the tubular body is manufactured by extrusion of a biocompatible polymer.

The invention is also directed to an expandable medical device that delivers a therapeutic agent to a vascular site using consistent "on-demand" delivery while not substantially eluting or releasing therapeutic agent(s) while the device is being tracked to a desired location within the vasculature. The medical device of the current invention comprises an expandable member with (or without) a structural or substrate layer over the expandable member, at least one hydrophilic coating comprising at least one therapeutic agent disposed on the expandable member or structural layer, and an outer sheath comprising a variably permeable microstructure. During use, the underlying hydrophilic coating becomes hydrated or partially hydrated and facilitates fluid transfer across the outer sheath. However, said outer sheath's closed microstructure in the unexpanded state prevents unwanted, premature release of said therapeutic agent in the unexpanded state. Upon expansion, the orientation or configuration of the microstructure of the material comprising the outer sheath, which is disposed over the expandable member, transforms from a substantially closed microstructure to a substantially open microstructure allowing the hydrated or partially hydrated coating to be transferred outward. This feature of the microstructure of the material is one embodiment of a material having a variably permeable microstructure. Once the hydrated or partially hydrated hydrophilic coating passes through the outer sheath, the therapeutic agent is delivered to the treatment site. In one embodiment, the hydrated or partially hydrated coating comprises a therapeutic agent and once the outer sheath is expanded, the therapeutic agent transfers through the sheath. In another embodiment, said expandable member is a medical balloon. In another embodiment, said outer sheath has a relatively closed microstructure when there is no strain on the outer sheath. In another embodiment, said sheath has a more open microstructure when said sheath is strained (i.e., diametrically strained). The strain on said outer sheath can be exerted by said expandable member during expansion.

Figure 2A:
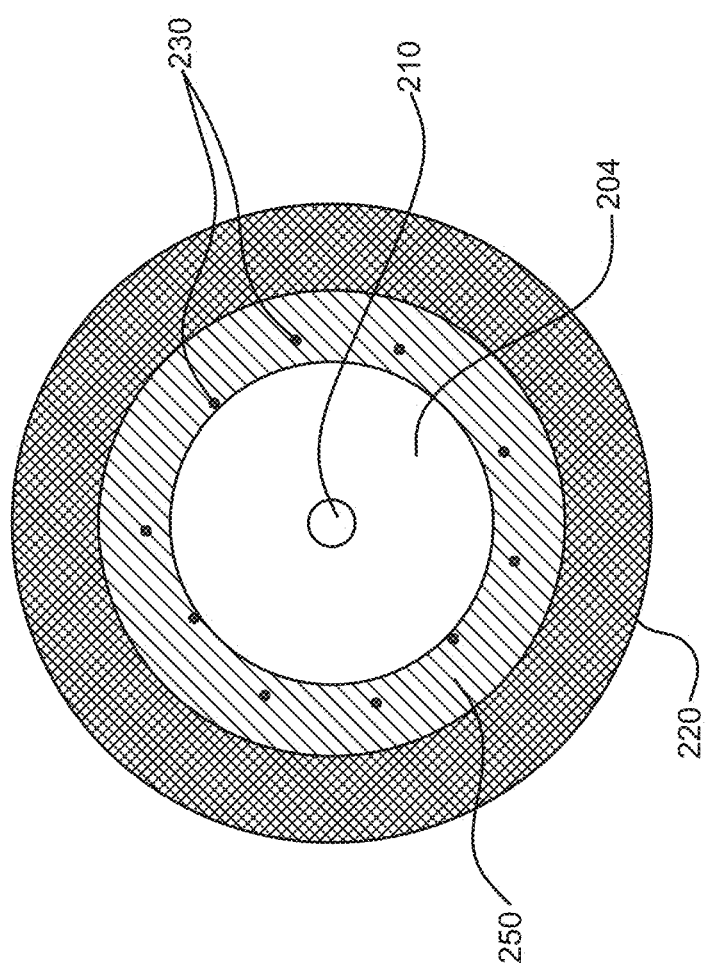
FIGS. 2A and 2B depict a cross-section of the drug delivery balloon of the invention in its first, unexpanded state (2A) and in its second, fully expanded, state (2B).

The agent elution construct of the invention comprises several aspects to help control delivery of therapeutic agents from an expandable member. FIG. 2A is a cross-section of an agent elution construct comprising a balloon in its first, uninflated, state. The construct comprises a balloon 204, a hydrophilic coating 250 on balloon 204 and an outer sheath 220. Hydrophilic coating 250 further comprises at least one therapeutic agent 230. Also depicted is guidewire lumen 210 that extends through the length of the balloon. In one embodiment, said hydrophilic coating is substantially dehydrated prior to device insertion into the vasculature. Alternatively, in other embodiments, said coating is pre-solvated or pre-hydrated prior to introduction into body. In various embodiments, the outer sheath 220 is made from a material having a variably permeable microstructure. In another embodiment, outer sheath 220 is wrapped or folded over hydrophilic coating 250 at a first, uninflated diameter.

Materials which may exhibit variably permeable microstructures are known to the art. These include, but are not limited to, fibrillated structures, such as expanded fluoropolymers (for example, expanded polytetrafluoroethylene (ePTFE)) or expanded polyethylene (as described in U.S. Pat. No. 6,743,388 and incorporated herein by reference); fibrous structures (such as woven or braided fabrics; non-woven mats of fibers, microfibers, or nanofibers; materials made from processes such as electrospinning or flash spinning; polymer materials consisting of melt or solution processable materials such as fluoropolymers, polyamides, polyurethanes, polyolefins, polyesters, polyglycolic acid (PGA), polylactic acid (PLA), and trimethylene carbonate (TMC), and the like; films with openings created during processing (such as laser- or mechanically-drilled holes); open cell foams; microporous membranes made from materials such as fluoropolymers, polyamides, polyurethanes, polyolefins, polyesters, PGA, PLA, TMC, and the like; porous polyglycolide-co-trimethylene carbonate (PGA:TMC) materials (as described in U.S. Pat. No. 8,048,503 and incorporated herein by reference); or combinations of the above. Processing of the above materials may be used to modulate, enhance or control permeability between a first, closed state and second, expanded. Such processing may help close the microstructure (thus lower permeability) in a first state, help open the microstructure in a second state, or a combination of both. Such processing which may help close the microstructure may include, but is not limited to: calendaring, coating (discontinuously or continuously), compaction, densification, coalescing, thermal cycling, or retraction and the like. Such processing that may help open the microstructure may include, but is not limited to: expansion, perforation, slitting, patterned densification and/or coating, and the like. In another embodiment, said materials comprise micropores between nodes interconnected by fibrils, such as in ePTFE. In another embodiment, said material comprises micropores in an essentially nodeless ePTFE, as described in U.S. Pat. No. 5,476,589, which is hereby incorporated by reference in its entirety for all purposes.

In another embodiment of the invention, the surface(s) or outward configuration of the sheath material may be modified with textures, protrusions, wires, blades, spikes, scorers, depressions, grooves, coatings, particles, and the like. In another embodiment of the invention, the surface(s) or outward configuration of the sheath material may be modified with needles, cannulae, and the like. These modifications may serve various purposes such as to modify tissues into which therapeutic agents will be (or have been) delivered, control placement of the system of the invention, and direct fluid transfer. Such textures may help in increased transfer of a therapeutic agent onto, more deeply and/or into deeper tissues. Optionally, coatings can aid in enhancing microscopic or macroscopic wetting of said sheath material. In one embodiment, said coating of said sheath material comprises crosslinked polyvinyl alcohol (see, e.g., U.S. Pat. No. 7,871,659). Said coating of said variably permeable microstructure material can also comprise a heparin coating, such those described in U.S. Pat. Nos. 4,810,784 and 6,559,131, both of which are hereby incorporated by reference herein in their entireties for all purposes.

In another embodiment of the invention, the location(s) of the permeable microstructure may be varied. For example, a sheath may be constructed such that only a portion of its microstructure is variably permeable. Such a configuration may be desirable where fluid transfer is not desired to occur, for example, at one or both of the ends of the expandable medical device of the invention. This may be desirable where multiple drug eluting devices will be used in a specific anatomy, and it would be undesirable to overlap treatments sites, i.e., delivering too much drug to a particular site.

In another embodiment, the sheath may contain or be marked with radiopaque markers or be constructed to be radiopaque in its entirety. Such radiopaque indicators are used by clinicians to properly track and place an expandable medical device of the invention.

As used herein, the term "variably permeable microstructure" refers to a structure or material with a resistance to fluid transfer at a first state that is higher than the resistance of the same structure or material at a second state with such resistance varying between the two states. One skilled in the art will appreciate various methods which characterize the change in permeability from testing at a first state and comparing to testing done at a second state. These methods include, but are not limited to, characterizations of air or liquid flux across the microstructure at a given pressure differential, characterization which determines the pressure differential at which different fluids strike through the microstructure such as Water Entry Pressure or Bubble Point, characterization of porosity, and visual characterization such as inter-nodal or inter-fibril spacing as measured from an image (e.g. from a scanning electron microscope or light microscope). One non-limiting embodiment of a variable permeable material comprises a material that has a substantially closed microstructure when the material is not under a strain and has a more open microstructure when the material is strained.

As used herein, the terms "micropores" and "microporous" refer to openings in materials, for example the area between ePTFE nodes and fibrils. Usually, as in the case of ePTFE, these micropores contain air when the material is not "wetted".

As used herein, the terms "wet", "wet-out" and "wetted" refer to the displacement of air in a microporous material by a fluid. Wetting of a material lowers the resistance to subsequent fluid transfer and facilitates the flow of fluids though the microporous material. Furthermore, these microporous materials are intended to be open cell structures, meaning the micropores are interconnected, and not closed cell structures. This allows fluid to flow through the material. Capillary effects may also play an important role in fluid flow though the material as wetting occurs, especially for highly porous materials with small interconnected pores. The microstructure of outer sheath can be selected to maximize capillary effects to produce improved hydration, recognizing that this can compete with obtaining a microstructure at second diameter that provides optimal drug transfer. Wetting can be accomplished with the aid of one or more surfactants added to the fluid. The surfactant can absorb onto the fluid-vapor, solid-fluid, and solid-vapor interfaces, which in turn modifies the wetting behavior of hydrophobic materials. The wetting will also depend on the viscosity to the fluid.

As used herein, the term "coating" refers to one or more materials disposed on the surface of a substrate. In the present invention the substrate may include the structural layer or substrate or expandable member or outer sheath. Said coating may lie completely on the surface or may be incorporated, in whole or in part, within the openings or pores present in a substrate. The latter coating configuration is commonly referred to in the art as "imbibed" or "filled" materials.

As used herein, the term "dry coating" or "dehydrated coating" refers to the inability of the coating alone to sufficiently wet the outer sheath by the displacement of air in a microporous material. Some dry coating embodiments may be formulated with at least one component that is in a liquid state in its pure form capable of causing wet-out, but when combined with additional components results in a dry coating. In contrast, as used herein, the term "pre-hydrated" refers to a coating that is hydrated or partially solvated prior to introduction into a body. Pre-hydrated coatings may not require pre-wetting of the sheath.

Figure 2B:
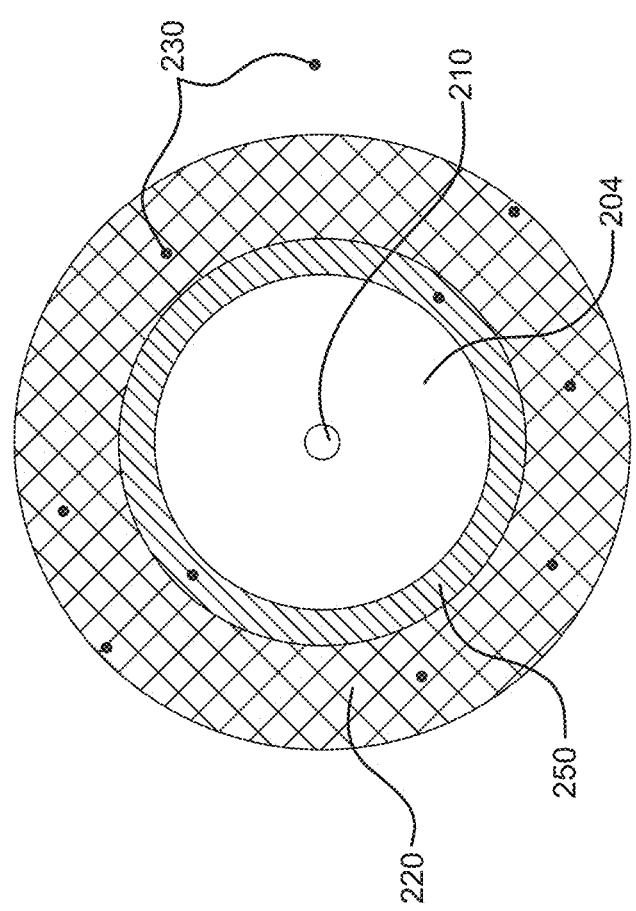

As used herein, the term "vessel" refers to any luminal or tubular structure within the body to which these constructs can be utilized. This includes, but not limited to, vascular blood vessels, vascular defects such as arteriovenous malformations, aneurysm, or others, vessels of the lymphatic system, esophagus, intestinal anatomy, sinuous cavity, uterus, or other. The embodiments of the present invention are also suitable for the treatment of a malignant disease (i.e. cancer) within or associated with a vessel FIG. 2B depicts the same construct as FIG. 2A, except that the agent elution construct is at its second, expanded, state. This Figure depicts an inflated balloon 204, a hydrophilic coating 250 on the balloon 204 and an outer sheath 220, depicting a more open microstructure (e.g., if said sheath comprises ePTFE, said open microstructure comprises increased distance between the nodes and/or increased distance between the fibrils and/or changes in orientation of the fibrils and/or nodes (fibril and/or node re-orientation)). The hydrophilic coating 250 further comprises at least one type of therapeutic agent 230. Also depicted is guidewire lumen 210 that extends through the length of the balloon. As seen in this Figure, therapeutic agent 230 is passing from the surface of balloon 204, into and through the outer sheath 220, and out of the balloon construct. It will be understood that the hydrophilic coating 250 may, in some embodiments, pass into and through the outer sheath 220, and out of the balloon construct. In another embodiment, upon expansion, the hydrophilic coating 250 passes into and through the outer sheath 220 in a hydrated or partially hydrated state. In another embodiment, outer sheath 220 is wetted after expansion. In another embodiment, said sheath is fully wetted before expansion. In another embodiment, said sheath is partially wetted before expansion. In another embodiment, coating 250, once external to the sheath 220, is tissue adherent and remains adhered to the target tissue even after the device is removed. This embodiment allows for continued drug transfer from the adherent coating at the tissue interface until the tissue adherent coating dissipates from the target tissue, as described in the co-pending and co-assigned U.S. Patent Publication 20100233266. In another embodiment, the coating comprises a thixotropic gel.

FIGS. 3A, 3B, 3C, and 3D are scanning electron micrographs (SEMs) of two different outer sheaths with variably permeable microstructures that comprises ePTFE. Specifically, FIGS. 3A and 3C respectively show outer sheath 1 and outer sheath 2 when these agent elution constructs are in their first, unexpanded, state. As seen in 3A and 3C, the microstructures of these outer sheaths are relatively compact with fibrils and nodes positioned close to one another. There are very few and/or very small micropores in these structures.

Figure 3A:
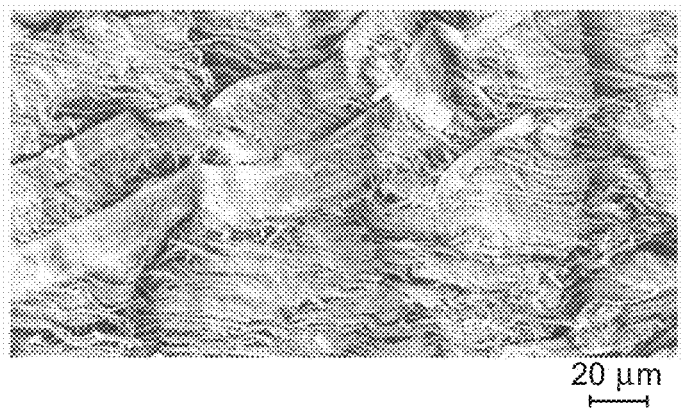
FIGS. 3A through 3D are scanning electron micrographs (SEMs) of two different outer sheaths comprising ePTFE.
Figure 3B:
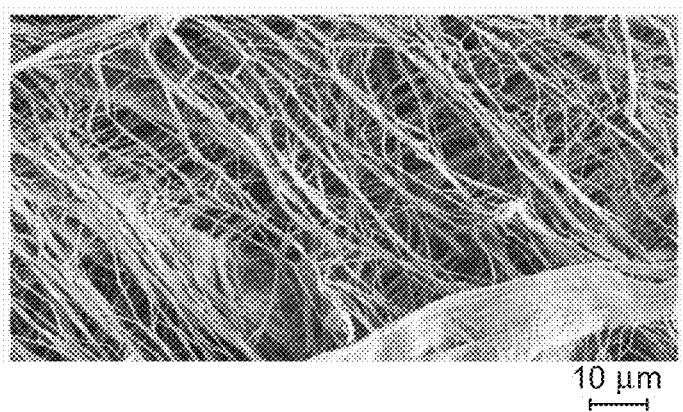
Figure 3C:
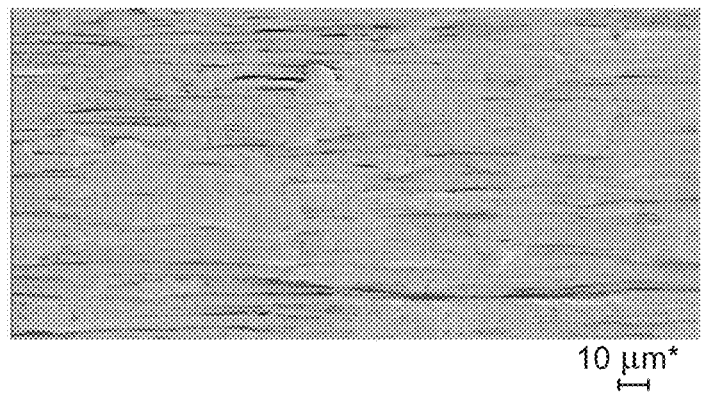
Figure 3D:
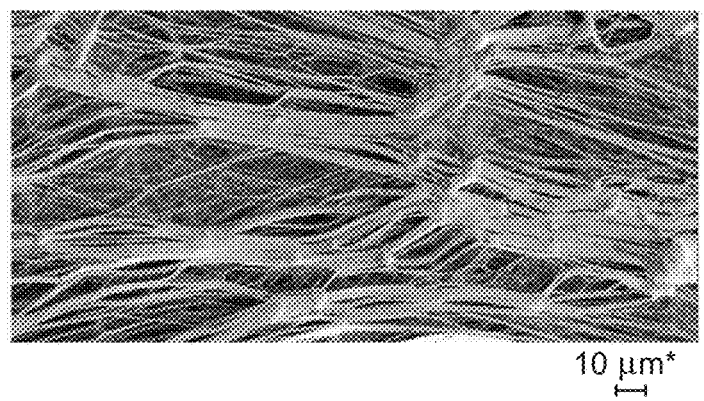

FIGS. 3B and 3D show outer sheath 1 and outer sheath 2 of FIGS. 3A and 3C, respectively, in their second, expanded state. As shown in these micrographs, the microstructures are now considerably more open than that seen in FIGS. 3A and 3C. In other words, the distance between nodes and/or the distance between fibrils have increased. As can be seen in these Figures, distance between nodes has increased and the orientation of the fibrils has changed. As a result, micropores are larger (as compared to FIGS. 3A and 3C). Since the micropores of FIGS. 3B and 3D are larger than the micropores of FIGS. 3A and 3B, fluid can penetrate and (at least partially) displace the air within the micropores. When this occurs, the outer sheath is wetted.

Most microporous materials will eventually wet-out with body fluids following implantation. However, this process may require significant time (hours to days). In the case of some fluoropolymers, such as ePTFE, its hydrophobic nature can greatly slow the process of replacing air with fluid, which may slow or completely restrict therapeutic agent release from a coated expandable member, e.g. balloon, underlying under the outer sheath. However, if the ePTFE is wet too quickly, which can occur when the micropores are too large, then premature drug release may occur before balloon catheter is positioned at the desired location.

In one embodiment, one of the disclosed inventions addresses this dilemma by the use of a "switch" mechanism that controls drug elution as a function of expansion of the expandable member. This controlling switch mechanism results from the novel combination of an expandable microporous material in the outer sheath with a dehydrated hydrophilic coating underneath the outer sheath. In one embodiment, once the hydrophilic coating begins to become, or is fully hydrated, the tight porosity of the outer sheath at its first state, as shown in FIGS. 3A and 3C, will serve as a bulk fluid transfer barrier to the hydrated or partially hydrated coating and/or the therapeutic agent associated therewith. However, upon expansion (i.e., inflation of the medical balloon), the combination of the opening of the micropores, as shown in FIGS. 3B and 3D, with pressure-driven expansion and the hydrated or partially hydrated hydrophilic coating rapidly displacing air within at least a portion of the outer sheath (i.e., the coating wets-out the outer sheath), transfer of the coating or coating and therapeutic agent occurs. Such transfer occurs without particulation. At the same time, as the outer sheath expands, body fluids will also displace air within the outer sheath allowing for an influx of body fluids which will further hydrate the coating and which, in turn, help the coating displace the air in the outer sheath. In this embodiment, the hydrophilic coating is selected from a group that while being hydrophilic is also compatible with the sheath material to affect sheath wetting and subsequently provide for efficient coating transfer into and through the microstructure of the sheath. Such compatibility of coating to sheath material(s) can be tailored to meet the desired wetting characteristics (see, e.g., U.S. Pat. No. 5,874,165 which is hereby incorporated by reference in its entirety for all purposes).

This "switching" phenomenon is possible due to a unique combination of a dehydrated hydrophilic coating which contains a therapeutic agent combined with a variably permeable and expandable outer sheath. The combination results in an agent eluting construct that prevents the transfer of therapeutic agent at first state but which allows for transfer of therapeutic agent at its second state where there the agent eluting construct exhibits an increase in pore size of the outer sheath. Without being bound to a particular theory, therapeutic agent transfer may be related to two main drivers: the hydrophilic coating acting as a wetting agent; and shear forces at the interfaces of the outer sheath and coating as expansion occurs.

The switch mechanism represents a dynamic continuum as the variably permeable microstructure of the outer sheath changes in response to wetting and/or an expansion force. When the microstructure opens in response to said expansion force, there is also sufficient force to drive fluid transfer. When this occurs the agent elution construct of the invention is said to be "switched" from an "off" state in which the therapeutic agent and/or coating cannot pass through the sheath to an "on" state in which it can. It will be understood that the agent elution construct of the invention is not binary in its operation. Instead, while fluid transfer may be initiated at a discrete point in time, transfer rates will vary in accordance with the degree (and period of time) at which the microstructure of the outer sheath changes, e.g., opens and/or closes, is wet, or remains partially wetted, etc. Such changes may be controlled, for example, by varying the pressure of a semi-compliant expandable member. Such transfer rates can also be variably distributed across the surface of the outer sheath. For example, by selecting an outer sheath material which offers different pore sizes or pore densities in one region as compared to another, transfer rates between each region will be different. In another example, the outer sheath can comprise a composite or combination of materials, each with their own pore characteristics. An outer sheath with essentially uniform pore size and density can also be modified to provide variably distributed transfer, for example, by forming microbores in one surface region of the sheath while leaving the remaining regions unmodified. Microbores, as used herein, are formed holes that go straight through the sheath and can be formed by any known techniques, e.g., laser perforation. In comparison, micropores are typically meandering and are part of the material's microstructure.

In the embodiment in which the expandable member is a balloon and the outer sheath comprises ePTFE, when the balloon is in its first state, the ePTFE comprising outer sheath has a substantially closed microstructure, as shown in FIGS. 3A and 3C, because said sheath is collapsed around said balloon. Thus, the micropores are very small and will not readily: allow body fluids to substantially traverse the outer sheath, allow fluid transfer of the underlying coating (even if hydrated or partially hydrated), or allow for particulation of the therapeutic agent and/or coating during the time course of typical clinical usage of the therapeutic intervention. (As will be described below, there may be partial and/or full hydration of the underlying coating due to a small amount fluid transfer inward through the sheath enhanced by the addition of wetting agent(s) to the outer sheath). Once the drug delivery balloon of the invention is at the desired location in the patient's body, the balloon is inflated, thus expanding the outer sheath to an open microstructure, as shown in FIGS. 3B and 3D. As the microstructure expands, micropores become larger, bodily fluids (e.g., blood, serous fluid) displace air in the microstructure, and these fluids begin to flow inward through the outer sheath. The underlying hydrophilic coating is now exposed to an influx of said body fluids. As the body fluids hydrate the hydrophilic coating, the coating, in turn, will facilitate rapid wetting of the outer sheath by body fluids. Without being bound to a particular theory, this mechanism provides a feed-back loop that imparts rapid wet-out of the outer sheath and hydration of the hydrophilic coating. As the outer sheath wets out and the hydrophilic coating hydrates, the therapeutic agent is transported through the outer sheath by bulk fluid flow of the hydrated or partially hydrated coating as the balloon is inflated. This, in turn, will cause further wetting of the ePTFE and further reduce the barrier to transfer of the therapeutic agent. This embodiment enables consistent, controlled on-demand drug delivery to a target site (e.g. a body vessel). In another embodiment, the hydrated or partially hydrated coating will be forced through the outer sheath by the pressure applied by the expanding balloon.

In other embodiments, the space between the outer sheath and the expandable member can be in fluid communication with an infusion lumen. In such embodiments, said coating can be hydrated or solvated by an infused fluid rather than, or in addition to, the fluid transfer inward through the sheath from surrounding body fluids. In various embodiments, a structural layer can comprise a wicking material as described herein to facilitate distribution of infusion fluid about the outer surface of the expandable member. In addition, a therapeutic agent can be delivered via said infusion lumen. In another embodiment, the fluid can comprise a gel or viscous fluid comprising a therapeutic agent.

In another embodiment, a cover may surround all or a portion of the drug eluting balloon catheter of the present invention. Such covers may work to isolate the balloon catheter surface from the external environment during shipment and storage or during use, e.g., during tracking of the catheter to a treatment site. In one embodiment, the cover comprises a film cover held in place by stitching, for example the stitching as disclosed in U.S. Pat. No. 6,352,553. In another embodiment, the cover comprises a film which can be everted off of the drug eluting balloon.

In another embodiment, an expandable device, such as a stent or stent-graft, may be mounted to the agent elution construct of the invention, delivered to a site within the body where the expandable device is expanded and placed. The advantage of this application is that a therapeutic agent can be delivered to the treatment site at the same time as said expandable device is being delivered. This prevents clinicians from having to switch between a stent delivery balloon and a drug delivery balloon. In one embodiment, said stent is made from a balloon expandable material, such as stainless steel. In another embodiment, said stent is made from a self-expanding material, such as Nitinol. In another embodiment, said stent is made from a biodegradable material, such as a biodegradable polymer, metal or metal alloy. In another embodiment, said stent comprises a graft. In another embodiment, said graft comprises ePTFE.

In another embodiment, a hydrophilic coating or a hydrophilic coating in combination with a therapeutic agent is applied to only a portion of an expandable member, e.g., the surface of the balloon, in a discontinuous fashion. Upon "switching" the coating and/or therapeutic agent are delivered to a discrete or more localized site external to the outer sheath. In contrast, when the coating and/or therapeutic agent is applied in an even distribution to the entire surface of the expandable member, expansion (e.g. "switching") enables uniform delivery of the coating and/or therapeutic agent from the entire circumference of the expandable member.

As described in the examples below, fluid transfer through the outer sheath is also assisted by touching the expanding outer sheath against the vessel wall. In this situation, outer sheath's contact with the vessel may cause the surrounding body fluid pressure to exceed the fluid entry pressure of the outer sheath. In other words, the vessel may push fluid external to the outer sheath into the micropores of the sheath. Thus, in one embodiment, fluid transfer of the outer sheath is facilitated when said sheath is in contact with the vessel wall.

As also described in examples below, the outer sheath can be prepared with a second diameter that is less than or more than the nominal diameter of the underlying expandable member to help modulate fluid transfer. For example, in an embodiment, the second diameter of the outer sheath is less than the nominal diameter of the underlying expandable member. As such, the outer sheath can provide a resistance to growth above nominal diameter of the underlying expandable member, e.g., balloon. This may, in turn, help to facilitate rapid wetting of the outer sheath, which aids in fluid/coating/ therapeutic agent transfer through the outer sheath. Thus, in one embodiment, as the balloon is inflated to nominal diameter, the hydrated or partially hydrated coating is trapped between an underlying balloon that is growing and an outer sheath that is resisting such growth. This provides some of the driving force for bulk fluid transfer of the hydrated or partially hydrated coating through the outer sheath. In further embodiments, the compliancy of the outer sheath material can also be varied to also modulate fluid transfer.

Similarly, a medical device can be configured to provide tension along the length of outer sheath. Before, during, or after inflation of the expandable member, tension (for example, axial tension) can be applied to the outer sheath, which can decrease its radial dimension providing an increased stress on the underlying balloon. This increased stress can further aid in the transfer of the fluid/coating/ therapeutic agent through the outer sheath, due to increased pressures between the expandable member and the tensioned sheath. For example, in an embodiment, the proximal and distal ends of the outer sheath can be attached to two different elongate members. These two elongate members are coaxial and slidable with respect to each other. This construct can be used to apply tension across the outer sheath by extending the inner elongate member relative to the outer elongate member. In further embodiments, the outer sheath can be configured to "neck down" upon the application of axial tension. For example, the outer sheath can comprise a braided member or two oppositely oriented helical wraps. Upon application of tension, the angle between the braided elements or the helical wraps and the longitudinal axis will decrease, creating a corresponding decrease in diameter.

In addition, due to the dimensions of the microstructure of the outer sheath as the balloon is tracked to the treatment site and during inflation, substantially no coating particles greater than about 25 µm are released. In another embodiment, a very small amount of coating particles greater than about 5 µm, about 10 µm, about 15 µm, or about 25 µm are released through the outer sheath. Thus, particulation of the drug and/ or the coating matrix is minimized. In another embodiment, said outer sheath expands, but does not tear or break.

Thus, one embodiment of the invention comprises the drug delivery system comprising an expandable member, such as a balloon, which may comprise a structural layer and/or a substrate, at least one dehydrated or partially dehydrated hydrophilic coating containing at least one therapeutic agent, said coating located on the expandable member or structural layer and/or substrate, and an outer sheath with a variably permeable microstructure which is expandable by the expandable member. In its unexpanded state, the sheath is of a lower permeability. As it is expanded, it becomes more permeable. In one embodiment, the hydrophilic coating becomes at least partially hydrated prior to the sheath being expanded, but the coating and the therapeutic agent do not pass (or substantially pass) through the outer unexpanded sheath. In another embodiment, a driving force sufficient to transfer the coating across the sheath is necessary. In another embodiment, as the sheath is expanded and its microstructure opens, the hydrated or partially hydrated coating lowers the fluid entry pressure of the sheath and this, in combination with increasing pore size of the sheath and a higher driving force supplied by the expandable member, causes fluid transfer of the coating and/ or the therapeutic agent through the sheath. Once the hydrated or partially hydrated hydrophilic coating passes through the sheath, the therapeutic agent in the coating is delivered to the treatment site. In another embodiment of the invention, the lowering of the fluid entry pressure of the sheath is effected via wetting of the outer sheath by a wetting agent applied to said outer sheath. In another embodiment, the wetting agent on said outer sheath comprises poly(vinyl alcohol) (PVA) or a heparin coating.

In another embodiment of the invention, the fluid entry pressure of the sheath can be determined by selection of a suitable porous, hydrophilic material which does not require a wetting agent to function in accordance with the invention. For example, hydrophilic membranes comprising an expanded functional TFE copolymer may be used to constructed the sheath. Such membranes are disclosed in U.S. Patent Publication 2012/0035283, hereby incorporated by reference in its entirety.

In another embodiment of the invention, a hydrophobic drug is sequestered by or complexed with one or more solubilizing agents such that when delivered to the intended tissue site the drug dissociates from the solubilizing agent and binds to tissue. In various embodiments, coating can comprise a solubilizing agent, such as a sequesterant, a surfactant, a hydrotrope, or a wetting Agent. Solubilizing agents are known in the art (see, e.g., U.S. Patent Publication 2008/ 0118544, hereby incorporated by reference in its entirety).

Figure 4A:
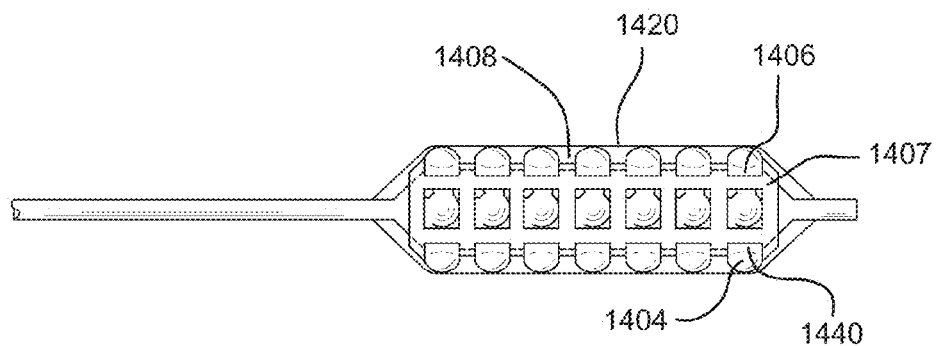
FIGS. 4A and 4B depict side views of a drug eluting balloon having a three-dimensional surface in a first inflated state
Figure 4B:
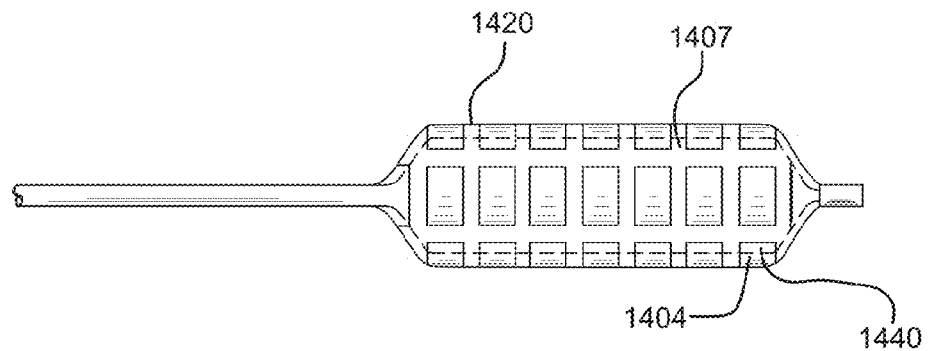

Optionally, with reference to FIGS. 4A and 4B, the underlying expandable member 1404 or structural layer 1440 can be configured to assume a three dimensional surface upon inflation to a first diameter, said surface comprising at least one protrusion 1406 and regions surrounding or between the protrusion(s) ("channels" 1408) in which the coating can collect when hydrating or when hydrated. The three dimensional surface can be formed by overlaying the expandable member 1404 or structural layer 1440 with a plurality of constraints (for example fibers or wires) or a template 1407 that defines apertures through which the underlying balloon 1404 or structural layer 1440 will protrude during inflation. Such constraints or templates 1407 will typically be less compliant than the underlying expandable member 1404. In an embodiment, the pressure within the expandable member 1404 can be increased to a certain pressure threshold, at which the restraining force of the constraints or template 1407 is overcome thus causing the protrusions 1406 to be reduced or eliminated as the constrained regions increase in size. The fluid collected in the channels will then be driven through the outer sheath 1420. The template or constraints 1407 can, for example, be constructed of a frangible material configured to release at a certain pressure threshold, thereby eliminating the protrusions. In an embodiment, the template or constraints 1407 can be constructed to release at different inflation pressures. In an embodiment, coating that is held on the surface of the expandable member 1404 in the location above these constraints 1407 will be delivered upon release of the constraints 1407 allowing for a sequential delivery of therapeutic agent. In another embodiment, tension can be applied to the outer sheath 1420, as described herein, causing the height of protrusions 1406 to be reduced or eliminated and the coating to be released.

Another embodiment of the invention comprises a medical device comprising, an expandable member, a coating comprising a therapeutic agent disposed around said expandable member, a sheath disposed around said coating, wherein said sheath has a variably permeable microstructure that initially prevents or limits unintended transfer of therapeutic agent through said sheath, wherein said coating and therapeutic agent are disposed between the surface of the expandable member and the sheath, and wherein when said expandable member and sheath are expanded, said sheath allows transfer of said coating and therapeutic agent to an area external to said sheath while preventing transfer of particles out of said sheath greater than about 25 microns in size. For example, the maximum effective pore size of the microstructure at second diameter is less than or equal to about 25 microns. In other embodiments, particles greater than about 25 microns in size can transfer through said sheath. In one embodiment, said expandable member is a medical balloon. In another embodiment, said medical device comprises a catheter. In another embodiment, said sheath rapidly wets out during expansion, and said sheath allows rapid transfer of said coating and therapeutic agent. In another embodiment, said sheath undergoes microscopic wetting in a vessel while said balloon and sheath are in the unexpanded state and being delivered to a desired location within a vessel. In another embodiment, bodily fluids substantially wet-out the sheath when said sheath is being expanded. In another embodiment, said hydrophilic component also wets the sheath when said sheath is being expanded. In another embodiment, substantially all of said sheath is wet by the time said sheath is fully expanded. In another embodiment, fluid external to said sheath is allowed to flow through said sheath, and contact said therapeutic agent. In another embodiment, said wetting of said sheath is facilitated when said sheath is in contact to the vessel wall. In another embodiment of the invention, wetting of the outer sheath is facilitated by a wetting agent applied to said outer sheath. In another embodiment, the wetting agent of said sheath comprises poly(vinyl alcohol) (PVA) or a heparin coating. In another embodiment, said sheath comprises a fluoropolymer. In another embodiment, the sheath comprises a microstructure comprised of nodes interconnected by fibrils. In another embodiment, said nodes are aligned longitudinally to the longitudinal axis of said balloon catheter and said fibrils are aligned circumferentially to said axis. In another embodiment, said nodes are aligned circumferentially to the longitudinal axis of said balloon catheter and said fibrils are aligned longitudinally to said axis. In another embodiment, said nodes are spread apart as said outer sheath expands. In another embodiment, the orientation of said nodes changes as said outer sheath expands. In another embodiment, said fibrils are spread apart as said outer sheath expands. In another embodiment, said fibrils are unfolded, straightened out or reoriented as said outer sheath expands. In another embodiment, said coating comprises a hydrophilic component. In another embodiment said coating comprises at least one compound selected from the group consisting of benzethonium chloride, poloxamer-188, polyethylene glycol, sodium salicylate, and hydroxypropyl-β-cyclodextrin. In another embodiment, said therapeutic agent is a hydrophilic agent. In another embodiment, said therapeutic agent is a hydrophobic agent. In another embodiment, said therapeutic agent is paclitaxel or a taxane domain-binding drug. In another embodiment, said expandable member further comprises a structural layer. In another embodiment, said structural layer comprises said coating and therapeutic agent. In another embodiment, the microstructure of the sheath changes as said expandable member expands.

In some embodiments, if the sheath and/or the structural layer are composed of a thin film wherein said film comprises a microstructure of nodes interconnected by fibrils, then unlike extruded tubes, said nodes will not pass through the entire thickness of said structural layer and/or sheath. Said nodes are only as thick as the film. Accordingly, the along the thickness of a film tube (i.e., a tube made of wrapping a film) in which there are several passes of a film, there will be a number nodes only as thick as the film and placed randomly along the thickness of said film tube. For the purposes of this invention, the term "nodes aligned circumferentially" means that if a majority of nodes have a length that is longer than the width of said node, then the length of said node will be aligned in the circumferential direction of a wrapped tubular construct, such as a structural layer and/or sheath (see, e.g. FIG. 3C). For the purposes of this invention, the term "nodes aligned longitudinally" means that if a majority of nodes have a length that is longer than the width of said node, then the length of said node will be aligned to the longitudinal axis of a wrapped tubular construct, such as a structural layer and/or sheath. In another embodiment, if a tubular construct made from a film wherein said film comprises a microstructure of nodes interconnected by fibrils and said nodes are aligned in a circumferential direction, then upon radial expansion of said tube, said nodes increases in length. Methods of making tubes made from films are described below.

The variably permeable microstructure can be selected so that at second diameter there is a decreased resistance to flow. In various embodiments, the variably permeable microstructure at second diameter can have a lower surface area per area of cover, thereby decreasing the resistance to bulk flow of a therapeutic agent. As the variably permeable microstructure opens upon expansion and is strained, the specific surface area per area of cover is reduced.

Another embodiment of the invention comprises a sheath disposed around a coating disposed on an expandable member where the sheath is purposefully under- or over-sized in diameter to further modulate fluid transfer through the outer sheath. By "under-sized" it is meant a sheath which will not expand greater than the nominal diameter of the underlying expandable member without stretching. This is useful because it can prevent the balloon from bursting and also constrain the volume of coating and/or therapeutic agent, helping to drive transfer of the coating and/or therapeutic agent through the outer sheath. By "over-sized" it is meant a sheath expandable beyond (or constructed to be) of a diameter larger than the nominal diameter of the underlying expandable member.

In another embodiment, the variably permeable microstructure of the outer sheath can be selected or controlled to modify how inflation pressure affects the release of the therapeutic agent. For example a sheath may be selected which allows transfer of the coating and/or therapeutic agent over a narrow range of inflation pressures. Conversely, the sheath may be constructed to provide transfer over a larger range of inflation pressures. In addition, the sheath may be constructed to tailor transport in conjunction with changes in diameter of the agent eluting device due to changes in inflation pressure. The desired variability can, for example, be achieved by using different materials for the outer sheath and/or different thickness of said materials and/or different orientations of said materials and/or different processing of said materials.

As used herein, the terms "rapid" and "rapidly" refer to a clinically relevant timeframe, e.g., less than about 5.0 minutes. In another embodiment, the terms "rapid" and "rapidly" are defined herein to mean about 90, about 60, about 50, about 45, about 30, about 20, or about 10 seconds.

In some embodiments, the outer sheath will not be fully wet out. As further described below, very small, microscopic areas of the outer sheath can be wetted out. As used herein the term, "microscopic-wetting" refers to small areas of the outer sheath which wet, (i.e., air is replaced by liquid fluids) but these wet areas are so small that such wetting, that may be indicated by translucence of the wetted material (depending on the material), will not be visible to naked eye. In one embodiment, the outer sheath is composed of ePTFE which may undergo microscopic wetting, and thus, the outer sheath will not become translucent. Microscopic-wetting can occur when the outer sheath is in its first diameter and may contribute to pre-hydration of the coating. As will be further described below, wetting occurs in areas of the outer sheath where the micropores are large enough to allow air displacement by fluids.

As used therein the term "macroscopic wetting" is when the outer sheath is wet and wetting can be detected by the naked eye, for example, by at least a portion of an ePTFE comprising outer sheath becoming translucent.

In some instances, the outer sheath, by design or due to variations in manufacturing, may have pores that allow microscopic wetting by fluids. This allows the fluids to enter through the outer sheath and to the coating, thus pre-hydrating the coating. Therefore, as the agent elution construct of the invention is being tracked to the desired location, body fluids may be pre-hydrating the dehydrated or partially-dehydrated hydrophilic coating. The examples below suggest that it may be helpful to pre-soak the balloon construct of the invention in order to achieve rapid and complete wet-out of the outer sheath. Thus, one embodiment of the invention provides for pre-hydration of the hydrophilic coating provided by body fluids as the agent elution construct of the invention is being tracked to the target site. As used herein the term "pre-hydration" means that the hydrophilic coating is hydrated or partially hydrated while the expandable member and the outer sheath are in their first, unexpanded, state. In this embodiment, in their first, unexpanded, state, the coating and/or therapeutic agent will not be released to an area external to the outer sheath in significant quantities. It will be appreciated by one of skill in the art that pre-hydration might be accomplished in whole or in part during preparation of the device prior to introduction into a patient.

As discussed, it may be beneficial to have some fluid transfer into and through the outer sheath in order to have pre-hydration of the hydrophilic coating, depending, inter alia, on the coating and/or therapeutic agent formulation. However, relying on pores due to variability in manufacturing of a microporous structure, such as ePTFE, may not be sufficient to induce pre-hydration of the hydrophilic coating and rapid wet-out of the outer sheath during expansion. Thus, in one embodiment, a portion of the outer sheath (exterior area) is treated with a wetting agent. Suitable wetting agents include a hydrophilic coating or others well known in the art. That portion of the sheath "imbibed," "filled" or treated by the wetting agent will instantaneously (i.e., in less than about 10 seconds) wet-out when contacted by bodily fluids ("point wetting"). In turn, this allows said bodily fluids to pass through the sheath and into the hydrophilic coating, thus causing said coating to hydrate or partially hydrate. In another embodiment, the hydrophilic coating will fully hydrate, even if such "point wetting" is employed. This is because even small amounts of bodily fluids in contact with the coating are rapidly transported throughout the coating, hydrating the coating to some degree. Because the rest of the sheath remains unexpanded and/or unwetted, the now hydrated or partially hydrated coating remains substantially on the inside of the outer sheath until it is expanded by mechanisms described above. In another embodiment, said fluid is a vapor that can pass through the outer sheath and condense on the dehydrated coating. In this embodiment, the outer sheath may not become wet but allows for coating hydration. In another embodiment, conditioning the outer sheath with a wetting agent can be varied and/or patterned along the length and surface area of the outer sheath so that wetting of said outer sheath is uneven. This may help in adjusting the rate of wetting, the rate of delivery and/or amount of said therapeutic agent/coating delivered. In one embodiment, the outer sheath is partially conditioned with a wetting agent in a pattern along the outer sheath's surface to allow for "near instantaneous" wetting (i.e., in less than about 20 seconds).

In other embodiments, the entire outer sheath is treated, coated, imbibed and/or filled with a wetting agent that can be cross-linked to allow instantaneous wetting (i.e., in less than about 10 seconds) of the outer sheath following contact with an aqueous medium, as described in U.S. Pat. No. 7,871,659, and U.S. Pat. No. 5,897,955, both of which are hereby incorporated by reference in their entireties for all purposes. In one embodiment, said wetting agent includes, but is not limited to poly(vinyl alcohol) polyethylene glycol, heparin, heparin coatings (such as those described in U.S. Pat. No. 6,461,665), polypropylene glycol, dextran, agarose, alginate, polyacrylamide, polyglycidol, poly(vinyl alcohol-co-ethylene), poly(ethyleneglycol-co-propyleneglycol), poly(vinyl acetate-co-vinyl alcohol), poly(tetrafluoroethylene-co-vinyl alcohol), poly(acrylonitrile-co-acrylamide), poly(acrylonitrile-co-acrylic acid-co-acrylamidine), polyacrylic acid, poly-lysine, polyethyleneimine, polyvinyl pyrrolidone, polyhydroxyethylmethacrylate, and polysulfone, and their copolymers, either alone or in combination. In another embodiment, said wetting agent includes glycols, fatty acid salts, and fatty alcohols, and combinations thereof. However, the hydrated or partially hydrated coating and/or therapeutic agent will not be substantially transferred (or only a small amount may transfer) through the outer sheath in its first, unexpanded state because the outer sheath has closed microstructure and/or because there is no back pressure forcing the hydrated or partially hydrated coating to be transferred (e.g. pushed) outward.

In other embodiments, an outer sheath which is treated, coated, imbibed and/or filled with a wetting agent will exhibit a decreased thickness from the sheath material prior to application of a wetting agent.

In another embodiment, said outer sheath has small perforations, holes, slits, larger pores, or any other imperfection that allows body fluids to pre-hydrate the hydrophilic coating, without substantially allowing any therapeutic agent or coating particles to be released into the bloodstream while the balloon is in the first state. In another embodiment, controlled release of the inflation media from the underlying balloon may also serve to pre-hydrate the coating. In another embodiment, the pre-hydration occurs due to purposeful leaking of a seal between the expandable member and the outer sheath. In another embodiment, said outer sheath does not tear or come apart during expansion. As explained above and suggested by data in the examples, pre-hydration may help in rapid and complete wetting of the outer sheath as it expands. However, this may be dependent on the formulation of the coating.

In another embodiment, the microporous nature and/or "wettability" of the outer sheath may be distributed over only a portion or portions of the outer sheath. For example, certain locations on the surface of the microporous sheath material may be filled with another material (e.g., silicone and or polyurethane) and made non-microporous and/or non-wettable, but leaving the non-filled areas microporous. Similarly, changes in sheath surface structure (e.g., from "patterning" of the surface) may also be selectively located to create regions of the sheath which are not wettable. Such modifications to the sheath may be useful in instances where therapeutic agents transport through the sheath occur from only certain locations of the sheath. In one embodiment, this approach may be used to deliver therapeutic agents from only a portion of the sheath e.g., to treat only a portion of the radial diameter of a blood vessel which is especially useful where eccentric lesions are present. Such lesions account for approximately 70% of all flow-limiting intravascular lesions. In another embodiment, said distributed wettability can control the rate that said outer sheath becomes wet. Thus, said outer sheath can be modified to have differential permeability throughout the entire outer sheath or can be patterned in such a way to allow for differential permeability at different locations throughout the outer sheath. This embodiment allows for uneven and/or a patterned delivery of therapeutic agents and/or coatings.

In another embodiment, the outer sheath is wet-out by a prescribed preparatory procedure prior to being inserted into the patient. In this embodiment, said agent eluting construct is prewetted in a sterile liquid (e.g. saline) supplied with said construct or in the patient's own blood.

Figure 5:
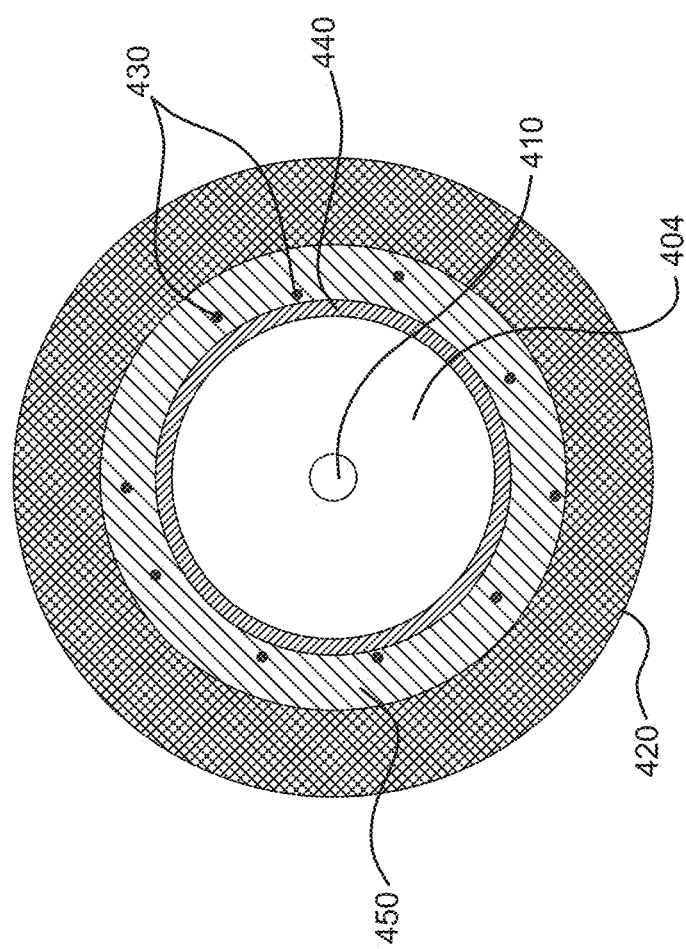
FIG. 5 depicts a cross-section of the drug eluting balloon of the invention similar to FIG. 2A with the addition of a structural layer.

Another embodiment of the invention, as depicted in FIG. 5, comprises a cross-section of an agent elution construct in its first, unexpanded, state. In this embodiment, the construct comprises a balloon 404, a substrate or structural layer or cover 440, a hydrophilic coating 450 on balloon 404 and an outer sheath 420. Hydrophilic coating 450 further comprises at least one therapeutic agent 430. Also depicted is guidewire lumen 410 that extends through the length of the balloon. Structural layer 440 can serve many functions. One of its functions may be to serve as a substrate for uniformly applying the hydrophilic coating 450 to the underlying balloon 404. Since some balloon materials may not be conducive to being uniformly coated, the structural layer can serve as a scaffold to achieve a uniform coating. In addition, if the structural layer comprises an elastomer, the structural layer can help with recompaction of the underlying balloon (see, e.g., U.S. Pat. No. 6,120,477, Campbell, et al., which is hereby incorporated by reference in its entirety for all purposes). In another embodiment, the structural layer can be coated with said hydrophilic coating and said therapeutic agent prior to placement on an expandable member. With such a pre-fabricated, coating construct, any balloon can be converted to an agent elution construct of the invention. Thus, one embodiment of the invention comprises using a coated structural layer and placing it on any "off the shelf balloon" or OEM balloon to make the balloon a drug delivery balloon. In another embodiment, the hydrophilic coating is coated onto structural layer 440 and then dehydrated or partially dehydrated. In another embodiment, said dehydrated or partially dehydrated hydrophilic coating comprises at least one therapeutic agent. In another embodiment, structural layer 440 and/or outer sheath 420 are wrapped or folded over at a first, uninflated diameter.

A structural layer, for example one made according to the examples below, also provides for a uniform tube to be coated at first state which will concentrically/uniformly expand up to a second state. In contrast, conventional Percutaneous Transluminal Angioplasty (PTA) balloons must be coated at second state (in their molded shape) and then be compacted down to a first state. A structural layer can be coated separate from the catheter or balloon on a mandrel, and later assembled onto the balloon with increased manufacturing yields, lower costs, and higher uniformity. As described above, the coating on said structural layer will be covered by an outer sheath. As the balloon is inflated to its second state, the coating will become hydrated or partially hydrated. The hydrated or partially hydrated coating can flow around said structural layer as the balloon is inflated.

The structural layer can be made from any material that is compatible with the coating and which can be expanded to accommodate expansion of the balloon. These materials include, but are not limited to ePTFE, fluoropolymers, expanded polyethylene, polyvinylchloride, polyurethane, silicone, polyethylene, polypropylene, polyurethane, polyglycolic acid, polyesters, polyamides, elastomers and their mixtures, blends and copolymers, are all suitable. In one embodiment, said structural layer comprises ePTFE. In another embodiment, said ePTFE is imbibed with an elastomer, such as a thermoplastic copolymer of tetrafluoroethylene and perfluoroalkylvinylether, which can be free of cross-linking monomers and curing agents as described in U.S. Pat. No. 8,048,440, hereby incorporated by reference in its entirety.

In another embodiment of the invention, the surface(s) or outward configuration of the structural layer (or expandable member if a structural layer is not used) may comprise textures, folds, flaps, invaginations, corrugations, pleats, protrusions, spikes, scorers, depressions, grooves, pores, coatings, particles, and the like or combinations thereof. In another embodiment, said depressions, corrugations, pleats, grooves, and/or pores can be used increase the effective surface area over which the coating can be placed. Such surfaces can be etched to increase the effective surface area. In other embodiments, structural layer can comprise a fibrillated microstructure. The fibrils can comprise folds/micropleats to increase the effective surface area. This may help enhance the solvation or hydration cycle. It can also help in reduction of length or profile of the overall medical device. In another embodiment, the structural layer may comprise a wicking material. Wicking material can facilitate the hydration of the coating. As microwetting occurs wicking material can distribute the fluid. In further embodiments, the wicking material can be partially exposed, i.e., not covered by the outer sheath, at one or more sites along the medical device. The exposed sites allow for body fluids to migrate into wicking material and hydrate the coating. In an embodiment, the wicking layer helps transport a fluid to the coating from a source external to the expandable member, for example from a catheter hub. In an embodiment, the wicking layer can comprise a material having an open pore membrane of PTFE such as that described in U.S. Pat. No. 5,814,405 by Branca et al. entitled "Strong, Air Permeable Membranes of Polytetrafluoroethylene," which is hereby incorporated by reference describes in further detail. Other suitable materials can include open cell polyurethane foam, open cell silicone foam, open cell fluoropolymers, or any other pliable materials comprising micro or macro channels to allow infusion. Wicking material can contain a wetting agent as described herein to improve the distribution of the fluid. Wicking material can also serve as a sponge that holds the therapeutic agent until sufficient pressure between a body surface and the expandable member expels the therapeutic agent from the wicking material, forcing it through the outer sheath.

Figure 6:
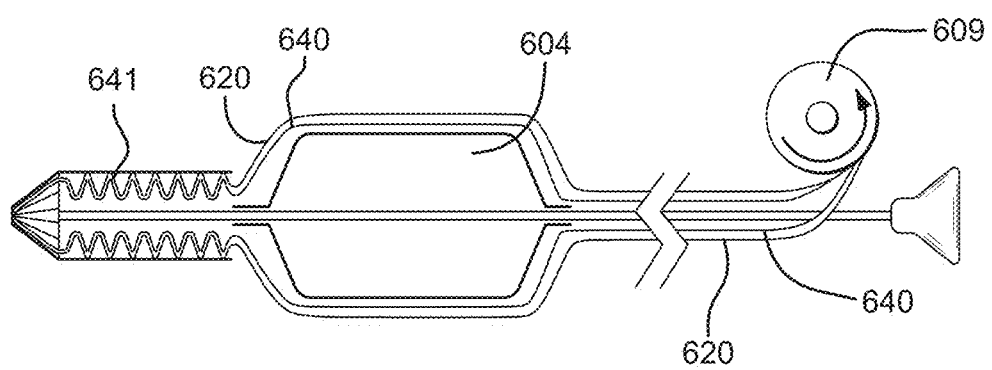
FIG. 6 depicts a cross-section of a drug eluting balloon construct capable of delivering multiple doses. A structural layer and outer sheath with a coating disposed there between is located about the balloon and additional length of the same is shown stored at a location distal the balloon. This excess length can be slid over the balloon to "reload" the balloon with a new section of drug eluting cover.

In another embodiment, with reference to FIG. 6, the structural layer 640 comprising a coating (not shown), and optionally the outer sheath 620, can comprise a length greater than that of the expandable member 604, wherein the excess length can be stored at a location proximal or distal the expandable member 604 and can be slid into position over the working length of the expandable member 604 by the clinician as needed. In this manner, once a section of coated structural layer has applied a therapeutic agent to a surrounding tissue, the spent section of structural layer 640 can be replaced with a new section by axially displacing the structural layer 640. In one embodiment, as is depicted in FIG. 6, excess length 641 can be stored at a location distal the expandable member 604 and a retraction wheel 609 or any other retraction mechanism can pull the structural layer in a proximal direction. In other embodiment, the excess length can be stored at location proximal the expandable member, and a slidable coaxial elongate member can extend in a distal direction to pull the structural layer in the distal direction.

In another embodiment of the invention and as an alternative to coating a structural layer, which is subsequently combined with an expandable member, the coating material may itself be formed into a structural component that is combined with an expandable member. Such constructs eliminate the requirement for a structural layer per se, yet fully preserve the key functions provided by the coatings of the invention. Such constructs may also improve manufacturability and can be combined with most any expandable member, such as a balloon. For example, where the expandable member comprises a balloon, a tubular form can be cast or otherwise formed from one or more materials of the described coating and disposed over the balloon prior to placement of the outer sheath. In one embodiment such tubular forms would be made by solvating the coating material(s) into a viscous state and through processes known to the art such as gel extrusion, casting, molding or solution casting/forming formed into the desired tubular shape. The solvent(s) used are subsequently removed to dry or partially dry the tube and makes it easy to dispose over the balloon. During use, the tube is rehydrated much like the coatings used with the invention and described herein.

In another embodiment, the structural layer is treated, coated, imbibed and/or filled with a wetting agent that can be cross-linked to allow rapid macrowetting (e.g., in less than about 10 seconds) of the outer sheath following contact with an aqueous medium. Such wetting agents include those described in U.S. Pat. No. 7,871,659, and U.S. Pat. No. 5,897,955, both of which are hereby incorporated by reference in their entireties for all purposes. In one embodiment, said wetting agent includes, but is not limited to poly(vinyl alcohol) polyethylene glycol, heparin, heparin coatings (such as those described in U.S. Pat. No. 6,461,665), polypropylene glycol, dextran, agarose, alginate, polyacrylamide, polyglycidol, poly(vinyl alcohol-co-ethylene), poly(ethyleneglycol-co-propyleneglycol), poly(vinyl acetate-co-vinyl alcohol), poly(tetrafluoroethylene-co-vinyl alcohol), poly(acrylonitrile-co-acrylamide), poly(acrylonitrile-co-acrylic acid-co-acrylamidine), polyacrylic acid, poly-lysine, polyethyleneimine, polyvinyl pyrrolidone, polyhydroxyethylmethacrylate, and polysulfone, and their copolymers, either alone or in combination. In another embodiment, said wetting agent includes glycols, fatty acid salts, and fatty alcohols, and combinations thereof.

The outer sheath and/or the structural layer can be made from any of the appropriate materials disclosed above. These structures can be made by extrusion or by layering any of the material described above, e.g. ePTFE. A layer is considered one thickness of a material which may be wrapped, folded, laid or weaved over, around, beside or under another thickness. A longitudinal pass comprises a distinctive layer or series of layers of material which are wound to form a region or area distinct from surrounding or adjoining parts. For instance, a pass may comprise multiple layers of a material wrapped at a desired angle relative to the longitudinal axis. This exemplary pass may then be flanked by layers of balloon material wrapped at dissimilar angles in relation to the longitudinal axis, thus defining the boundary of the pass. These layers may be oriented helically or circumferentially (or 90 degrees from the longitudinal axis). In addition, the sheath or structural layer can be helically wrapped at a low or high angle. A low angle wrap can yield a wrapped construct more distensible than a high angle wrap, all else being equal. The angle of the wrap can also vary the amount of stored length/foreshortening. One method for making the structural layer and outer sheath is described below in the examples. In one embodiment, said structural layer and/or outer sheath can vary in thickness along their longitudinal axes. This will allow for different shapes at the second, inflated diameter, and may also vary the amount and/or rate of coating and/or therapeutic agents that are transferred through the outer sheath. In another embodiment, the machine direction of said ePTFE layer is oriented along the longitudinal axis of the medical device. In another embodiment the thickness of the structural layer and/or outer sheath are comprised of different materials to tailor therapeutic agent elution and overall system performance. In another embodiment, the construction of the structural layer and/or outer sheath is discontinuous along the longitudinal axis of the components, e.g., one section of the outer sheath is thicker or comprises a different material, or is thinner than another section. In another embodiment, the ends of the structural layer and/or outer sheath are modified to decrease profile of the agent eluting device at the points on the underlying catheter where the structural layer and/or outer sheath are attached. For example, if the structural layer and/or outer sheath are constructed as tubes, a portion of the circumference of their ends may be skived away to open up the tube, i.e., making the ends of the tube only a portion of their original, full circumference. These end "tabs" are then attached to the catheter (using a method detailed below). Because these tabs comprise less material, the profile at the region of their attachment is decreased. In another embodiment, discrete perforations are created in the outer sheath, further modulating its capacity to elute a coating and/or therapeutic agent.

In various embodiments, the structural layer can comprise reinforcement materials that can withstand high pressures. Reinforcement strands, such as fibers, filaments, or wires can be incorporated into the structural layer to prevent failure during use, particularly under high pressure PTA procedures.

In various embodiments, the outer sheath can optionally attach to the structural layer in a desired location. Attachment sites can define a boundary for the region of drug delivery on the expandable member. For example, the outer sheath can attach to the structural layer or a balloon at its proximal end and a distal end, at or near the site of where balloon shoulders (or "cones") form during inflation. Such a construct can restrict the location of solubilized drug to over the working length of the balloon and limit or eliminate its flow into and out of the sheath overlying the shoulder regions. In other embodiment, attachment sites can define a plurality of discrete containment zones or "pockets" where drug delivery is preferred. For example, the outer sheath can be attached along an intermediate section of a balloon and at or near the site of where balloon shoulders form during inflation, forming zones of drug delivery at the proximal and distal regions of the working length of the balloon. Such constructs can be useful in ensuring uniform drug delivery to tissues and body locations which are structurally and anatomically varied, for example areas of non-uniform vessel conditions such as tapers, stenoses, eccentric lesions, asymmetric plaques, and the like. Unlike embodiments in which the hydrated coating occupies an annulus between the expandable member and outer sheath, or between a structural cover and outer sheath, the coating in these embodiments is sequestered into smaller areas. Upon expansion of the eluting construct and contact with variably shaped target tissues, rather than the coating being moved to areas of less contact pressure (for example distally and proximally when the center of the construct is located at a lesion), the coating is retained more proximate the target tissues, especially in areas of relatively high tissue contact pressures. In other embodiments, attachment to the structural layer in various preferred locations can aid in the re-compaction of the outer sheath (for example, when the structural layer comprises an elastomer) thus facilitating a smaller retraction profile. In various embodiments, an elastomeric adhesive can be used to create the attachment sites, e.g., a thermoplastic copolymer of tetrafluoroethylene and perfluoroalkylvinylether. In other embodiments, selective attachment of the structural layer to the outer sheath can provide manufacturing advantages since the coating and/or drug can be encapsulated within a sub-assembly comprising a structural cover, drug and/or coating and sheath. This sub-assembly can then be attached to a catheter which can offer a number of benefits. For example, such a manufacturing approach can allow for sterilization approached which differ for the subassembly and catheter, followed by aseptic assembly of them together into a finished product.

To make the agent elution construct of the present invention, a hydrophilic layer is formed on an expandable member or a structural layer by applying a hydrophilic substance comprising a therapeutic agent. The hydrophilic layer is applied to the surface of the balloon or a structural layer. The hydrophilic substance may then be optionally bound in place, such as through cross-linking. For a porous surface, the hydrophilic layer may optionally be adsorbed within the porous void spaces of the surface. Certain methods of coating a balloon or structural layer are described in detail in the examples below.

Suitable components for the hydrophilic coating include, but are not limited to, ionic surfactants including benzethonium chloride (e.g. HYAMINE®), benzalkonium chloride, cetylpyridinium chloride, cetalkonium chloride, laurtrimonium bromide, myristyltrimethylammonium bromide, cetrimide, cetrimonium bromide, stearalkonium chloride, n,n-diethylnicotinamide, cholesterol, calcium salicylate, methyl salicylate, sodium salicylate, sodium benzoate, benzoic acid, α-tocopherol, thiamine, niacinamide, dimethyl sulfoxide, decyl methyl sulfoxide, poloxamers (such as 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407), sorbitan monolaurate, sorbitan monostearate, sorbitan tristearate, octoxynols (such as Triton X-100 and Triton X-405), polysorbate 20, polysorbate 40, polysorbate 60, polysorbate 80, polyvinyl alcohol, polyvinylpyrrolidone, polyethylene glycol (PEG, molecular weight ranges from 400-50,000, with preferred from 700-15,000), PEG-amine, PEG-modified biopharmaceuticals and/or molecules, PEG amines (that include azido PEG amines and PEG diamines), JEFFAMINES® which are polyoxyalkyleneamines, quartenary ammonium compounds, 1,2-ditetradecanoyl-sn-glycero-3-phosphocholine, 1,2-dimyristoyl-sn-glycero-3-phospho-rac-(1-glycerol), 1,2-dimyristoyl-sn-glycero-3-phosphocholine, polypropylene glycol, heparin, or heparin derivatives, dextran, lactic acid, citric acid, ascorbyl palmitate, mannitol, palmitic acid, poly acrylic acid (Carbomer), gentisic acid, deoxycholic acid, glucuronic acid, amino acids, (such as histidine, lysine, arginine, glutamate, etc), polymeric chains of amino acids (such as polyarginine, polyglutamate), gluconolactone, agarose, stearic acid, stearyl alcohol, edetate disodium dehydrate edentate, hetastarch, phospholipids, cholesterol, liposomes, inclusion complexes such as cyclic oligosaccharides like cyclodextrin and its derivatives, including hydroxypropyl-β-cyclodextrin (HP-βCD), Captisol® (a trademark of CyDex Pharmaceuticals, Inc.), dimethyl-β-cyclodextrin, α-cyclodextrin (αCD), alginate, polyacrylamide, polyglycidol, poly(vinyl alcohol-co-ethylene), poly(ethyleneglycol-co-propyleneglycol), poly (vinyl acetate-co-vinyl alcohol), poly(tetrafluoroethylene co-vinyl alcohol), poly(acrylonitrile-co-acrylamide), poly (acrylonitrile-co-acrylic acid-co-acrylamide), polyacrylic acid, poly-lysine, polyethyleneimine, polyvinyl pyrrolidone, polyhydroxyethylmethacrylate, cyclodextrins, γ-cyclodextrin, sulfobutylether-β-cyclodextrin, and polysulfone, polysaccharides, and their copolymers, shellolic acid, ipromide, urea, either alone or in combination. Other coatings are known in the art, see, e.g., U.S. Patent Publication 20100233266, which is hereby incorporated by reference in its entirety for all purposes, can also be used as part of this invention. In another embodiment, said hydrophilic coating is a heparin coating, such those described in U.S. Pat. Nos. 4,810,784 and 6,559,131.

In another embodiment, hygroscopic substances may be incorporated in the coating to accelerate fluid uptake. These materials include, but are not limited to saccharides, dimethyl sulfoxide, decyl methyl sulfoxide, polyvinyl alcohol, glycerol, many salts, including, but not limited to, sodium chloride, zinc chloride, and calcium chloride. Such hygroscopic substances will attract and hold water molecules from the surrounding environment through either absorption or adsorption and help in hydrating said dehydrated coating. Such hygroscopic substances may be combined with any of the excipients described herein and/or commonly known in the art.

In another embodiment, the coating can comprise drug binding agents which act to bind drug particles to one another.

In another embodiment, the coating can comprise a tissue uptake enhancer to increase the dwell time of the therapeutic agent on tissues, tissue uptake of the therapeutic agent, or drug efficacy. Tissue uptake enhancers include integrins, lectins, osmotic agents, membrane disrupters, vasodilators, or polyethylene glycol conjugates. Such uptake enhancers may also include but are not limited to mannitol, decyl methyl sulfoxide, dimethyl sulfoxide, histidine, lysine, lysine acetate, arginine, polyarginine, polyglutamate, poly (glutamate-PEG), sorbitan monostearate, sorbitan tristearate, ascorbyl palmitate, palmitic acid, poly acrylic acid (Carbomer), deoxycholic acid, glucuronic acid. In another embodiment, a therapeutic agent can be complexed with or bonded to a tissue uptake enhancer.

In other embodiments, the coating can comprise a thixotropic agent, mucoadhesive or other agent to enhance the amount of time the coating remains in contact with target tissues, i.e., "dwell time". Such thixotropic agents or mucoadhesive agents may include but are not limited to hetastarch, alginate, poly acrylic acid (Carbomer), polyvinylpyrrolidone (PVP), inclusion complexes of PEG and a cyclodextrin, and biochemically reactive PEG. In another embodiment, agents can be incorporated in the coating which serve to bind particles of a therapeutic agent to a target tissue.

In another embodiment, the coating can comprise a stabilizing agent to extend the "shelf life" of a device, such as antioxidants or other known preservatives.

Differential Scanning calorimetry (DSC) can be used to identify and characterize complexes and other physical states of the coating. Fourier Transform Infrared Spectroscopy (FTIR) or Nuclear Magnetic Resonance (NMR) may also be utilized to further characterize complex formation, micelle formation, hydrotrophs, and other formations, which alter the morphology of the therapeutic agent, and to characterize the coating.

A "therapeutic agent" as used herein, which is used interchangeable with the term "drug", is an agent that induces a bioactive response. Such agents include, but are not limited to, cilostazol, everolimus, dicumarol, zotarolimus, carvedilol, anti-thrombotic agents such as heparin, heparin derivatives, urokinase, and dextrophenylalanine proline arginine chloromethylketone; anti-inflammatory agents such as dexamethasone, prednisolone, corticosterone, budesonide, estrogen, sulfasalazine and mesalamine, sirolimus and everolimus (and related analogs), anti-neoplastic/antiproliferative/anti-miotic agents such as major taxane domain-binding drugs, such as paclitaxel and analogues thereof, epothilone, discodermolide, docetaxel, paclitaxel protein-bound particles such as ABRAXANE®(ABRAXANE is a registered trademark of ABRAXIS BIOSCIENCE, LLC), paclitaxel complexed with an appropriate cyclodextrin (or cyclodextrin like molecule), rapamycin and analogues thereof, rapamycin (or rapamycin analogs) complexed with an appropriate cyclodextrin (or cyclodextrin like molecule), 17β-estradiol, 17β-estradiol complexed with an appropriate cyclodextrin, dicumarol, dicumarol complexed with an appropriate cyclodextrin, β-lapachone and analogues thereof, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; lytic agents; anesthetic agents such as lidocaine, bupivacaine and ropivacaine; anti-coagulants such as D-Phe-Pro-Arg chloromethyl ketone, an RGD peptide-containing compound, AZX100 a cell peptide that mimics HSP20 (Capstone Therapeutics Corp., USA), heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; agents that interfere with endogenous vasoactive mechanisms; inhibitors of leukocyte recruitment, such as monoclonal antibodies; cytokines; hormones or a combination thereof. In one embodiment, said therapeutic agent is a hydrophilic agent. In another embodiment, said therapeutic agent is a hydrophobic agent. In another embodiment, said therapeutic agent is paclitaxel.

In another embodiment of the invention, said coating comprises at least one hydrophilic component that raises the solubility point of a hydrophobic therapeutic agent. As used herein, the term "raises the solubility point of a hydrophobic therapeutic agent" means that there is an increase of concentration of a hydrophobic therapeutic agent at least 10% above the maximum solubility for said therapeutic agent in neat DI-water at room temperature and standard atmospheric conditions. This is usually due to the presence of an additional agent that allows for enhanced solubility (i.e., a hydrophilic component in said coating). This still allows for a portion of the therapeutic agent to not be dissolved into the water. For example, paclitaxel at room temperature in neat DI-water has a solubility limit of about 0.4 μM in water. The addition of hydroxypropyl-β-cyclodextrin at a concentration of 60% (w/v in water) raises the solubilized concentration of paclitaxel in solution to approximately 4 mM, well above a 10% increase in solubility (Sharma et al., Journal of Pharmaceutical Sciences 84, 1223 (1995)).

As used herein, weight percent (wt %) is the dry weight of a coating and/or therapeutic agent after solvent removal. In one embodiment, formulations comprising benzethonium chloride and a hydrophobic agent, such as paclitaxel, the preferred range for said hydrophobic agent are from about 1 wt % to about 70 wt %. In another embodiment, said hydrophobic agent, such as paclitaxel, ranges from about 40 wt % to about 70 wt %. In another embodiment, said hydrophobic agent, such as paclitaxel, ranges from about 20 wt % to about 40 wt %. In another embodiment, said hydrophobic agent, such as paclitaxel, ranges from about 1 wt % to about 20 wt %. In another embodiment, said formulations of benzethonium chloride and a hydrophobic agent, such as paclitaxel, is less than 20 wt % of said hydrophobic agent, such as paclitaxel. In another embodiment, said hydrophobic therapeutic agent is selected from the group consisting of taxane domain-binding drugs, such as paclitaxel, and rapamycin.

In another embodiment, formulations of poloxamer and of a hydrophobic agent, such as paclitaxel, range from about 1 wt % to about 70 wt %, from about 1 wt % to about 50 wt %, from about 1 wt % to about 40 wt %, from about 10 wt % to about 20 wt % of said hydrophobic agent, such as paclitaxel.

In another embodiment, formulations of poloxamer, PEG and of a hydrophobic agent, such as paclitaxel, range from: about 1 wt % to about 70 wt %, about 1 wt % to about 50 wt %, or about 8 wt % to about 40 wt % of a hydrophobic agent, such as paclitaxel; about 1 wt % to about 55 wt %, about 1 wt % to about 40 wt %, or about 5 wt % to about 30 wt % of PEG; and about 1 wt % to about 70 wt %, about 20 wt % to about 70 wt %, about 20 wt % to about 60 wt % of poloxamer, e.g. poloxamer-188. In another embodiment, said hydrophobic therapeutic agent is selected from the group consisting of taxane domain-binding drugs, such as paclitaxel, and rapamycin.

In one embodiment, the agent elution construct of the invention comprises a coating comprising benzethonium chloride, and a hydrophobic therapeutic agent, wherein said hydrophobic therapeutic is less than 40 wt % of the dry coating. In another embodiment, said hydrophobic therapeutic agent is about 10 wt % to about 20 wt % of the dry coating and benzethonium chloride is about 80 wt % to about 90 wt % of the dry coating. In another embodiment, said hydrophobic therapeutic agent is selected from the group consisting of taxane domain-binding drugs, such as paclitaxel, and rapamycin.

In another embodiment, the agent elution construct of the invention comprises a coating comprising poloxamer-188, and a hydrophobic therapeutic agent, wherein said hydrophobic therapeutic agent is less than 60 wt % of the dry coating. In another embodiment, said hydrophobic therapeutic agent is about 10 wt % to about 30 wt % of the dry coating and said poloxamer-188 is about 60 wt % to about 75 wt % of the dry coating. In another embodiment, said hydrophobic therapeutic agent is selected from the group consisting of taxane domain-binding drugs, such as paclitaxel, and rapamycin.

In another embodiment, the agent elution construct of the invention comprises a coating comprising poloxamer-188 and PEG, and a hydrophobic therapeutic agent, wherein said hydrophobic therapeutic agent is less than 50 wt % of the dry coating. In another embodiment, said hydrophobic therapeutic agent is less than 50 wt % of the dry coating and PEG is less than 30 wt % of the dry coating. In another embodiment, said hydrophobic therapeutic agent is about 10 wt % to about 30 wt % of the dry coating and PEG is about 10 wt % to about 20 wt % of the dry coating. In another embodiment, said hydrophobic therapeutic agent is about 10 wt % to about 20 wt %, PEG is about 10 wt % to about 20 wt %, and poloxamer-188 is about 50 wt % to about 65 wt % of the dry coating. In another embodiment, said hydrophobic therapeutic agent is selected from the group consisting of taxane domain-binding drugs, such as paclitaxel, and rapamycin.

In another embodiment, the agent elution construct of the invention comprises a coating comprising benzethonium chloride and PEG, and a hydrophobic therapeutic agent, wherein said PEG is less than 30 wt % of the dry coating and said hydrophobic therapeutic agent is less than 50 wt % of the dry coating. In another embodiment, said PEG is about 10 wt % to about 20 wt % of the dry coating and said hydrophobic therapeutic agent is about 10 wt % to about 25 wt % of the dry coating. In another embodiment, said PEG is about 10 wt % to about 20 wt % of the dry coating, said hydrophobic therapeutic agent is about 10 wt % to about 25 wt % of the dry coating, and benzethonium chloride is about 50 wt % to about 65 wt % of the dry coating. In another embodiment, said hydrophobic therapeutic agent is selected from the group consisting of taxane domain-binding drugs, such as paclitaxel, and rapamycin.

In another embodiment, the agent elution construct of the invention comprises a coating comprising benzethonium chloride and poloxamer-188, and a hydrophobic therapeutic agent, wherein poloxamer-188 is less than 30 wt % and said hydrophobic therapeutic agent is less than 50 wt % of the dry coating. In another embodiment, poloxamer-188 is about 10 wt % to about 20 wt % of the dry coating and said hydrophobic therapeutic agent is about 10 wt % to about 35 wt % of the dry coating. In another embodiment, said poloxamer-188 is about 10 wt % to about 20 wt %, said hydrophobic therapeutic agent is about 10 wt % to about 25 wt %, and benzethonium chloride is about 50 wt % to about 65 wt % of the dry coating. In another embodiment, said hydrophobic therapeutic agent is selected from the group consisting of taxane domain-binding drugs, such as paclitaxel, and rapamycin.

In another embodiment, the agent elution construct of the invention comprises a coating comprising hydroxypropyl-β-cyclodextrin, and a hydrophobic therapeutic agent, wherein said hydroxypropyl-β-cyclodextrin is equal to or less than 98 wt % of the dry coating. In another embodiment, said hydroxypropyl-β-cyclodextrin is less than 80 wt % of the dry coating. In another embodiment, said hydrophobic therapeutic agent is selected from the group consisting of taxane domain-binding drugs, such as paclitaxel, and rapamycin.

In another embodiment, the agent elution construct of the invention comprises a coating comprising sodium salicylate, and a hydrophobic therapeutic agent, wherein said sodium salicylate is about 75 wt % to about 95 wt % of the dry coating. In another embodiment, said sodium salicylate is less than 80 wt % of the dry coating. In another embodiment, said hydrophobic therapeutic agent is selected from the group consisting of taxane domain-binding drugs, such as paclitaxel, and rapamycin.

The therapeutic agents useful in conjunction with the system of the invention may be delivered to the tissue in various structural forms, including but not limited to micelles, liposomes, micro-aggregates, nanospheres, microspheres, nanoparticles, microparticles, crystallites, inclusion complexes, emulsions, gels, foams, creams, suspensions, liquids, and solutions or any combination thereof. In one embodiment, the agent is delivered to the tissue in a solubilized form. In another embodiment, the agent is delivered to the tissue in a gel. In another embodiment, the agent is delivered to the tissue in a solubilized form that precipitates from solution into a solid form. In another embodiment, the agent is delivered to the tissue as a combination of solubilized and solid forms.

Figure 7A:
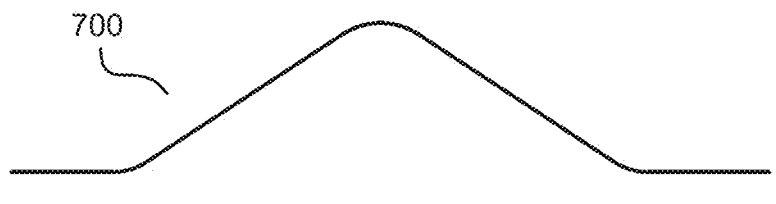
FIG. 7A to 7C depicts a cross-section of a balloon inflating first at a longitudinal center and then gradually inflating toward the proximal and distal ends.
Figure 7B:
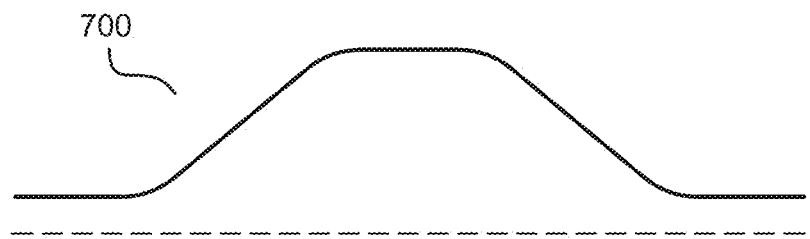
Figure 7C:

The "expandable member" according to the present invention can be a balloon, expandable catheter, stent, stent-graft, a self-expanding construct, a balloon expandable construct, a combination self-expanding and balloon expandable constructs, a blood vessel graft or a mechanical, radially expanding device which may be expanded, for example via application of a torsional or longitudinal force. Expandable members can also include those which expand due to pneumatic or hydraulic pressure, those which expand due to magnetic forces, those which expand due to the application of energy (for example electrical or ultrasonic (piezoelectric) energy), and those which expand due to osmosis. Expandable members can be placed temporarily in any lumen (e.g. a vessel) by expanding said device and then removed by collapsing said device by a torsional or longitudinal force. In one embodiment, a structural layer and outer sheath is placed on the device such that when it is expanded, a therapeutic agent will be delivered. In another embodiment, said expandable member allows for blood perfusion to downstream vasculature while implanted in said vessel. This feature may allow for longer implantation durations. In one embodiment, the expandable members may be detached in vivo, and optionally retrieved, from placement devices (e.g., catheters). Examples can be found in U.S. Pat. Nos. 3,996,938, 4,650,466, 5,222,971, and 6,074,339. In one embodiment, the expandable member is a medical balloon. Balloons useful in the invention may be blow-molded, may be compliant or semi-compliant or non-compliant and may be of various shapes, for example so called "conformable" or "conforming" or "steerable" balloons. In other embodiments, the expandable members may comprise balloons which are constructed of wrapped films, are fiber-wound, are of variable length, are segmented, and/or have controlled or variable inflation profiles. Such inflation profiles can be, for example, middle-out, where the middle of the balloon increases in diameter first, followed by inflation toward and ultimately including the ends; distal to proximal where the distal end inflates first and inflation progresses proximally; proximal to distal where the proximal end of the balloon inflates first and inflation progresses distally; or ends to middle where both ends of the balloon inflate first and inflation progresses toward the middle of the balloon. Controlled or variable inflation profiles may work to transfer fluid from the exterior of the balloon through the sheath in a preferential way. For example, with reference to FIG. 7A to 7C, a balloon 700 that inflates first in its longitudinal center region, and gradually followed by the ends proximal and distal the center region. Such a construct has the advantage of occluding or limiting flow through the vessel prior to a substantial portion of the therapeutic agent passing through the sheath. (In other words, a "no-flow" or "limited-flow" environment is created once the center portion of the balloon engages with the surrounding tissue.) In addition, this construct can have the effect of forcing some of the underlying solubilized therapeutic agent from the intermediate section to the proximal and distal edges of the balloon 700 as it expands. The outer sheath can be attached to the underlying balloon or structural layer at the edges, creating a barrier. Thus, the amount of therapeutic agent delivered through the outer sheath is greater on the proximal and distal sections than it is on the intermediate section. Focusing delivery in this manner can be useful in the case of treating stent re-stenosis, which commonly occurs at the stent ends. In other embodiments, the coating can be only located at the proximal and distal regions to focus delivery about these regions. In addition, the outer sheath can be attached to the balloon or structural layer to create containment zones as described herein. This can be a more efficient application of drug since the drug is not diluted as much at the ends of the balloon when compared to a traditional ends-to-middle deployment, since the blood is not flowing during drug release and application at the ends of the balloon.

Figure 8A:
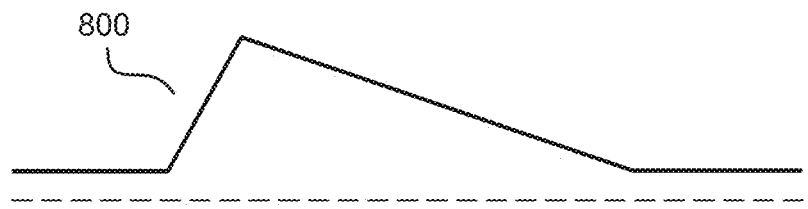
FIG. 8A to 8C depicts a cross-section of a balloon inflating first at a proximal or distal end and then gradually inflating toward the other end.
Figure 8B:
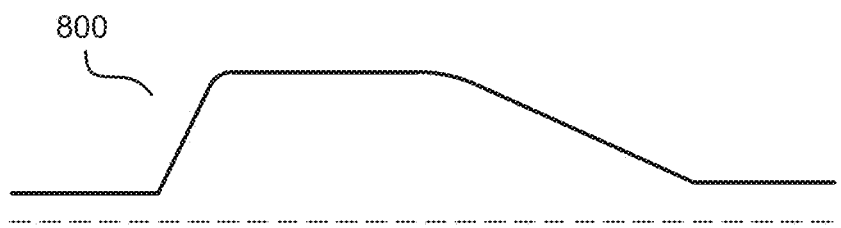
Figure 8C:
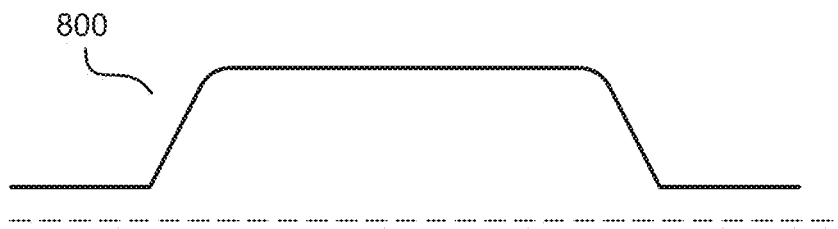

In other embodiments, with reference to FIG. 8A to 8C, a balloon 800 can inflate preferentially in either the distal or proximal region, with the opposite region subsequently inflating. Such a construct provides the advantages of occluding or limiting flow through the vessel prior to a substantial portion of the therapeutic agent passing through the sheath and concentrating the drug at one end of the balloon 800. (In other words, a "no-flow" or "limited-flow" environment is created once the distal or proximal portion of the balloon 800 engages with the surrounding tissue.) In addition, this embodiment can force some of the underlying therapeutic agent and/or coating from the region of the balloon 800 that first contacts the vessel, to remaining regions of the balloon 800 as it expands. Such an embodiment features the advantage of conserving and concentrating the therapeutic agent and/or coating at one end of the balloon 800 but utilizing greater surface for hydration of the coating and/or therapeutic agent. Such an embodiment can also reduce or block downstream transfer of the coating and/or therapeutic agent since proximate blood flow is limited or impeded. Such an embodiment also preserves maximum surface area of balloon available for further drug delivery within the same deployment.

Balloons with controlled or variable inflation profiles can be constructed as follows. In one embodiment, a cover may be created by wrapping a film membrane around the balloon. The number of wrapped layers varies along the length of the balloon with fewer layers being positioned over the balloon where expansion is desired to occur first. For example, a middle-out inflation is achieved by wrapping a larger number of layers on the distal and proximal ends of the balloon, leaving fewer layers in the middle of the balloon. The stress exerted by the balloon on the cover layers during balloon inflation meets a lower resistance in the middle of the balloon in this case, allowing the middle to expand first. This same concept can be applied to control inflation in the directions distal to proximal, proximal to distal, or ends to middle simply by varying the layers comprising the cover accordingly such that fewer layers are used where preferential inflation is desired.

In another embodiment, control of the balloon expansion profile can be achieved by preconditioning a portion of the balloon. Preconditioning can occur via repeated blow molding in different sized molds or can occur via one or more partial or full inflations of a portion of the balloon. Preconditioned regions of the balloon preferentially inflate before non-preconditioned regions since preconditioning lessens the force required to initiate an increase in diameter. Constraints (for example, rigid metal rings) can be used as manufacturing aids to inhibit inflation preconditioning in selected regions of the balloon.

Said drug eluting construct can be configured such that control of the balloon expansion profile can be independent of the final (nominal) diameter of the balloon. In one embodiment, the structural layer can be constructed such that although portions of the balloon may inflate in varying sequences, all regions of the balloon will ultimately reach the same final diameter. For example, a drug eluting construct with a middle out inflation profile can be designed such that the middle portion of the balloon begins to inflate at two atmospheres of pressure. The ends of the same drug eluting construct can be designed to increase in diameter at four atmospheres of pressure. At eight atmospheres, the balloon can be constructed such that the balloon ends reach a diameter essentially equal to the diameter of the middle. At such an inflation pressure, the balloon has essentially an equal diameter along its length. This can be achieved for example, by controlling the expansion profile via the structural layer, but using the underlying balloon to control the final diameter at full inflation.

The physical characteristics of said expandable members may also be modified, for example, they may have modulus values which differ from one another. In various embodiments, the medical balloon can be length adjustable The agent eluting construct of the invention comprises a structural layer and/or the expandable member that comprises a coating (that may or may not comprise at least one therapeutic agent) on said surface of said structural layer and/or the expandable member. Said coating can render said agent eluting construct very rigid. Due to its rigidity said agent eluting construct may be difficult to track through tortuous anatomy. Thus, in one embodiment, after applying coating to said structural layer and/or expandable member, the outer sheath is slipped over said structural layer and/or expandable member and then the coating is cracked by pre-stressing, such as through inflating, bending, and/or twisting said structural layer and/or the expandable member-outer sheath construct. The coating substrate, e.g., the structural layer, can be engineered to facilitate cracking by providing a rough surface or a surface that helps to concentrate stress in localized areas of the coating such as a cover with small nondistensible regions or areas of higher distention. This allows said agent eluting construct to be more conformable, while not allowing any particulates to escape the outer-sheath prior to treatment. In another embodiment, instead of fully coating the structural layer and/or the expandable member, said coating is applied as "rings" of coating such that in between said "rings" of coatings the structural layer and/or the expandable member is conformable and allow said structural layer and/or expandable member to bend at the uncoated region (allows for flexing). Said rings may also reduce hydration time of the coating by maximizing surface area of the coating in contact with a hydrating fluid. Reduced hydration time can improve overall system performance (e.g., time to effect delivery, degree of drug uptake, etc.). In another embodiment, rather than "rings", the coating and/or therapeutic agent are applied to the structural layer and/or the expandable member as an extruded, helically laid-down, continuous beading. In another embodiment, rather than "rings", the coating and/or therapeutic agent are applied to the structural layer and/or the expandable member as discrete dots or other shapes or discrete patterns. In another embodiment, said rings of coating can comprise the same therapeutic agent and/or different therapeutic agent and/or different coatings. In another embodiment, the coating and/or therapeutic agents are applied to a structural layer having a porous microstructure on its outer surface. When fluids are present to hydrate the coating, they can travel through this microstructure to augment hydration from beneath the coating. In an embodiment, the structural layer comprises an ePTFE material over which the coating is applied.

In another embodiment, the coating and/or therapeutic agent are applied to the structural layer and/or the expandable member in a discontinuous fashion. For example, the amount or thickness of coating may be varied over the surface of the substrate. In instances where drug delivery is desired only at the proximal and distal ends of a stent, for example, coatings applied to only the proximal and distal portions of the structural layer, expandable member and/or outer sheath (leaving the middle portion uncoated) may be desirable, especially for treatment or prevention of stent end stenosis. Coating and/or therapeutic agent compounds may similarly vary in thickness and/or over the area of the structural layer and/or the expandable member.

In another embodiment, the viscosity of the coating and/or therapeutic agent is selected to tailor the rate of drug delivery through the outer sheath. Said viscosity can also be varied to increase or decrease dwell time of a therapeutic agent on tissues if desired. In an embodiment, coating can comprise a thickening agent, e.g. a gelling agent. In addition, the microstructure of the outer sheath is configured to expand during expansion to a second diameter and permit transfer of a viscous and/or gelled coating.

In another embodiment, said agent eluting construct comprises an underlying medical balloon, a structural layer (optional), a coating comprising a therapeutic agent, and outer sheath wherein said components are mounted on a catheter. In one embodiment, the expanded diameter of said balloon is about 4 mm, about 5 mm, about 6 mm, about 7 mm, about 8 mm, about 9 mm, or about 10 mm in diameter with lengths ranging from about 30 to about 150 mm. In another embodiment, said balloon catheter will range in length from about 90 to about 150 cm. In another embodiment, said eluting balloon of the invention is about 5, 6, 7, 8, 9 or 10 French (Fr) in size before introduction into a body vessel, cavity or duct.

In another embodiment, said agent eluting construct comprises an underlying medical balloon, a structural layer (optional), a coating comprising a therapeutic agent, and outer sheath wherein said components are mounted on a catheter but may be detached from the catheter for short or long term implantation.

According to the present invention said balloon may be formed using any materials known to those of skill in the art. Commonly employed materials include the thermoplastic elastomeric and non-elastomeric polymers and the thermosets.

Examples of suitable materials include but are not limited to, polyolefins, polyesters, polyurethanes, polyamides, polyether block amides, polyimides, polycarbonates, polyphenylene sulfides, polyphenylene oxides, polyethers, silicones, polycarbonates, styrenic polymers, copolymers thereof, and mixtures thereof. Some of these classes are available both as thermosets and as thermoplastic polymers. See, U.S. Pat. No. 5,500,181, for example. As used herein, the term "copolymer" shall be used to refer to any polymer formed from two or more monomers, e.g. 2, 3, 4, 5 and so on and so forth.

Useful polyamides include, but are not limited to, nylon 12, nylon 11, nylon 9, nylon 6/9 and nylon 6/6. The use of such materials is described in U.S. Pat. No. 4,906,244, for example.

Examples of some copolymers of such materials include the polyether-block-amides, available from Elf Atochem North America in Philadelphia, Pa. under the tradename of PEBAX®. Another suitable copolymer is a polyetheresteramide.

Suitable polyester copolymers, include, for example, polyethyelene terephthalate and polybutylene terephthalate, polyester ethers and polyester elastomer copolymers such as those available from DuPont in Wilmington, Del. under the tradename of HYTREL®.

Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether may also be employed herein.

Specific examples of polyester/polyether block copolymers are poly(butylene terephthalate)-block-poly(tetramethylene oxide) polymers such as ARNITEL® EM 740, available from DSM Engineering Plastics and HYTREL® polymers available from DuPont de Nemours & Co, already mentioned above.

Suitable materials which can be employed in balloon formation are further described in, for example, U.S. Pat. No. 6,406,457; U.S. Pat. No. 6,284,333; U.S. Pat. No. 6,171,278; U.S. Pat. No. 6,146,356; U.S. Pat. No. 5,951,941; U.S. Pat. No. 5,830,182; U.S. Pat. No. 5,556,383; U.S. Pat. No. 5,447, 497; U.S. Pat. No. 5,403,340; U.S. Pat. No. 5,348,538; and U.S. Pat. No. 5,330,428.

The above materials are intended for illustrative purposes only, and not as a limitation on the scope of the present invention. Suitable polymeric materials available for use are vast and too numerous to be listed herein and are known to those of ordinary skill in the art.

Balloon formation may be carried out in any conventional manner using known extrusion, blow molding and other molding techniques. Typically, there are three major steps in the process which include extruding a tubular preform, molding the balloon and annealing the balloon. Depending on the balloon material employed, the preform may be axially stretched before it is blown. Techniques for balloon formation are described in U.S. Pat. No. 4,490,421, RE32,983, RE33, 561 and U.S. Pat. No. 5,348,538.

The balloon may be attached to the tubular body by various bonding means known to the skilled artisan. Examples include, but are not limited to, solvent bonding, laser welding, thermal adhesive bonding and heat shrinking or sealing. The selection of the bonding technique is dependent upon the materials from which the expandable element and tubular body are prepared. Refer to U.S. Pat. No. 7,048,713 to Wang for general teachings relating to the bonding of a balloon to a catheter.

In another embodiment, rather than a balloon acting as the expansion element for embodiments of the present invention, other expandable devices may be used. For example, a swellable gel tube can be located surrounding a catheter. A coating and/or therapeutic agent can then be applied to the outer surface of the gel tube. Optionally, a structural layer can be located between the gel tube and the coating and/or therapeutic agent. An outer sheath is then applied over the construct and sealingly attached to the catheter. A system is provided for hydrating the gel tube at the appropriate time during treatment. Upon hydration, the gel tube expands in diameter and drives the hydrated coating and/or therapeutic agent through the outer sheath and into contact with the tissue to be treated. In another embodiment, hydration of the gel tube also hydrates (or assists the hydration of) the coating and/or therapeutic agent, allowing it to be transferred through the outer sheath.

The agent eluting constructs provided by the present invention are suitable for a wide range of applications including, for example, a range of medical treatment applications within the body. Exemplary applications include use as a catheter balloon for transferred drug to or placement or "touch-up" of implanted vascular grafts, stents, stent-grafts, a permanent or temporary prosthesis, or other type of medical implant, treating a targeted tissue within the body, and treating any body cavity, space, or hollow organ passage(s) such as blood vessels, the urinary tract, the intestinal tract, nasal cavity, neural sheath, intervertebral regions, bone cavities, esophagus, intrauterine spaces, pancreatic and bile ducts, rectum, and those previously intervened body spaces that have implanted vascular grafts, stents, prosthesis, or other type of medical implants. Additional examples include an agent eluting construct device for the removal of obstructions such as emboli and thrombi from blood vessels, as a dilation device to restore patency to an occluded body passage, as an occlusion device to selectively deliver a means to obstruct or fill a passage or space, and as a centering mechanism for transluminal instruments like catheters. In one embodiment, agent eluting constructs provided by the present invention can be used to treat stent restenosis or treat tissue sites where previously placed drug eluting constructs have failed. In another embodiment, agent eluting constructs as described herein can be used to establish or maintain arteriovenous access sites, e.g., those used during kidney dialysis. In one embodiment, said agent eluting construct comprises a medical balloon used for Percutaneous Transluminal Angioplasty (PTA) in patients with obstructive disease of the peripheral arteries. In another embodiment, said agent eluting construct comprises a medical balloon used for Percutaneous Transluminal Coronary Angioplasty (PTCA) In another embodiment, agent eluting constructs provided by the present invention can be used to treat coronary stenosis or obstructions.

Another embodiment of the invention comprises a balloon catheter comprising, a balloon comprising a coating and a therapeutic agent disposed around the outer surface of said balloon, a sheath disposed around said balloon wherein said sheath has a microstructure composed of nodes interconnected by fibrils that prevents macroscopic wetting of said sheath in the unexpanded state, wherein said coating and therapeutic agent are disposed between the surface of the balloon and the sheath, and wherein when said balloon and sheath are expanded, substantially all of said sheath wets out rapidly and allows rapid transfer of said coating through the outer sheath. In one embodiment, said coating is transferred through said outer sheath and onto a target tissue. In another embodiment, said coating remains substantially adhered to the target tissue for greater than 1 minute after balloon deflation. In another embodiment, said sheath undergoes microscopic wetting in a vessel while said balloon and sheath are in the unexpanded state and being delivered to a desired location within a vessel. In another embodiment, bodily fluids substantially wet-out the sheath when said sheath is expanded. In another embodiment, said coating also wets said sheath when said sheath is expanded. In another embodiment, substantially all of said sheath is wet by the time said sheath is fully expanded. In another embodiment, said wetting of the sheath is facilitated when said sheath is in contact with a vessel wall. In another embodiment, said sheath contains a wetting agent to facilitate wetting of the sheath. In another embodiment, said sheath contains the wetting agent polyvinyl alcohol to facilitate wetting of the sheath. In another embodiment, said sheath comprises a fluoropolymer. In another embodiment, said nodes are aligned longitudinally to the longitudinal axis of said balloon catheter and said fibrils are aligned circumferentially to said axis. In another embodiment, said nodes are aligned circumferentially to the longitudinal axis of said balloon catheter and said fibrils are aligned longitudinally to said axis. In another embodiment, said nodes expand (elongate) said outer sheath expands. In another embodiment, said nodes are spread apart as said outer sheath expands. In another embodiment, the orientation of said nodes changes as said outer sheath expands. In another embodiment, said fibrils are spread apart as said outer sheath expands. In another embodiment, said fibrils are unfolded, straightened out or reoriented as said outer sheath expands. In another embodiment, said sheath comprises ePTFE. In another embodiment, said coating comprises a hydrophilic component. In another embodiment, said coating comprises at least one hydrophilic component selected from the group consisting of benzethonium chloride, PEG, poloxamer, sodium salicylate, and hydroxypropyl-β-cyclodextrin. In another embodiment, said therapeutic agent is a hydrophilic agent. In another embodiment, said therapeutic agent is a hydrophobic agent. In another embodiment, said hydrophobic agent is selected from the group consisting of taxane domain-binding drugs, such as paclitaxel, and rapamycin. In another embodiment, said balloon further comprises a structural layer. In another embodiment, said structural layer comprises said coating and therapeutic agent. In another embodiment, the microstructure of the sheath changes as said balloon expands.

Other embodiments of the invention comprise a method of delivering a therapeutic agent to a desired location within a vessel comprising, inserting a catheter in a vessel, said catheter comprising an expandable member comprising a hydrophilic coating with a therapeutic agent, a sheath disposed around said expandable member, wherein said sheath has a variably permeable microstructure that substantially prevents transfer of said coating and said therapeutic agent through said sheath in the unexpanded state, and wherein said coating and therapeutic agent are disposed between the surface of the expandable member and the sheath, advancing said catheter to a desired location within said vessel, and expanding the expandable member and sheath at the desired location within said vessel, and wherein substantially all of said expanded sheath allows transfer of said coating and therapeutic agent from between the surface of the expandable member and the sheath to an area external to said sheath while preventing transfer of particles out of said sheath greater than about 25 microns in size. For example, the maximum effective pore size of the microstructure at second diameter is less than or equal to about 25 microns. In other embodiments, particles greater than about 25 microns in size can transfer through said sheath. In one embodiment, said expandable member is a medical balloon. In another embodiment, said sheath rapidly wets out during expansion and allows rapid transfer of said coating and therapeutic agent. In another embodiment, said sheath undergoes microscopic wetting in a vessel while said balloon and sheath are in the unexpanded state and being delivered to a desired location within a vessel. In another embodiment, said wetting of the sheath is facilitated when said sheath is in contact with the vessel wall. In another embodiment, said sheath contains a wetting agent to facilitate wetting of the sheath. In another embodiment, said sheath contains the wetting agent polyvinyl alcohol to facilitate wetting of the sheath. In another embodiment, said sheath comprises a fluoropolymer. In another embodiment, the sheath comprises a microstructure comprised of nodes interconnected by fibrils. In another embodiment, said nodes are aligned longitudinally to the longitudinal axis of said balloon catheter and said fibrils are aligned circumferentially to said axis. In another embodiment, said nodes are aligned circumferentially to the longitudinal axis of said balloon catheter and said fibrils are aligned longitudinally to said axis. In another embodiment, said nodes expand (elongate) said outer sheath expands. In another embodiment, said nodes and are spread apart as said outer sheath expands. In another embodiment, the orientation of said nodes changes as said outer sheath expands. In another embodiment, said fibrils are spread apart as said outer sheath expands. In another embodiment, said fibrils are unfolded, straightened out or reoriented as said outer sheath expands. In another embodiment, said sheath comprises ePTFE. In another embodiment, said therapeutic agent is a hydrophilic agent. In another embodiment, said therapeutic agent is a hydrophobic agent. In another embodiment, said hydrophobic agent is selected from the group consisting of taxane domain-binding drugs, such as paclitaxel, and rapamycin. In another embodiment, said coating comprises at least one hydrophilic component selected from the group consisting of benzethonium chloride, PEG, poloxamer, sodium salicylate, and hydroxypropyl-β-cyclodextrin. In another embodiment, said expandable member further comprises a structural layer. In another embodiment, said structural layer comprises said coating and therapeutic agent. In another embodiment, the microstructure of the sheath changes as said expandable member expands.

Another embodiment of the invention comprises a balloon catheter comprising, a perfusing balloon comprising a coating and a therapeutic agent disposed around the outer surface of said perfusing balloon, a sheath disposed around said perfusing balloon wherein said sheath has a microstructure comprised of nodes interconnected by fibrils that prevents macroscopic wetting of said sheath in the unexpanded state, wherein said coating and therapeutic agent are disposed between the surface of the balloon and the sheath, and wherein during expansion of the balloon and sheath, the microstructure of the sheath changes and said balloon perfuses an inflation fluid. In one embodiment, said coating is transferred through said outer sheath and onto a target tissue, which is facilitated by the inflation fluid perfusing through said balloon. In another embodiment, said balloon does not begin to perfuse until a threshold pressure is reached or exceeded. Threshold pressures can be as low as about 1-2 atm or as high as about 60 atm. In an embodiment, the perfusing balloon can comprise macropores present in an otherwise impermeable balloon material. Alternatively, perfusing balloon can comprise micropores or a microporous membrane, e.g., ePTFE. In another embodiment, said sheath undergoes microscopic wetting in a vessel while said balloon and sheath are in the unexpanded state and being delivered to a desired location within a vessel. In another embodiment, bodily fluids substantially wet-out the sheath when said sheath is expanded. In other embodiments, the inflation fluid perfuses through said balloon to hydrate the coating. In another embodiment, said coating also wets said sheath when said sheath is expanded. In another embodiment, substantially all of said sheath is wet by the time said sheath is fully expanded. In another embodiment, said wetting of the sheath is facilitated when said sheath is in contact with a vessel wall. In another embodiment, said sheath contains a wetting agent to facilitate wetting of the sheath. In another embodiment, said sheath contains the wetting agent polyvinyl alcohol to facilitate wetting of the sheath. In another embodiment, said sheath comprises a fluoropolymer. In another embodiment, said nodes are aligned longitudinally to the longitudinal axis of said balloon catheter and said fibrils are aligned circumferentially to said axis. In another embodiment, said nodes are aligned circumferentially to the longitudinal axis of said balloon catheter and said fibrils are aligned longitudinally to said axis. In another embodiment, said nodes expand (elongate) as said outer sheath expands. In another embodiment, said nodes are spread apart as said outer sheath expands. In another embodiment, the orientation of said nodes changes as said outer sheath expands. In another embodiment, said fibrils are spread apart as said outer sheath expands. In another embodiment, said fibrils are unfolded, straightened out or reoriented as said outer sheath expands. In another embodiment, said sheath comprises ePTFE. In another embodiment, said coating comprises a hydrophilic component. In another embodiment, said coating comprises at least one hydrophilic component selected from the group consisting of benzethonium chloride, PEG, poloxamer, sodium salicylate, and hydroxypropyl-β-cyclodextrin. In another embodiment, said therapeutic agent is a hydrophilic agent. In another embodiment, said therapeutic agent is a hydrophobic agent. In another embodiment, said hydrophobic agent is selected from the group consisting of taxane domain-binding drugs, such as paclitaxel, and rapamycin. In another embodiment, said balloon further comprises a porous structural layer which allows inflation fluid to pass through the layer. In addition, the structural layer can comprise a wicking material to help ensure fluid is evenly dispersed around the balloon exterior. In another embodiment, said structural layer comprises said coating and therapeutic agent.

In another embodiment of the invention, agent elution constructs of the invention can be applied in configurations other than those which are radially circular. For example, this invention can be used in conjunction with planar devices such as wound dressings, implantable patches (including vascular and hernia patches), transdermal patches, filters, various device delivery components, occluders, and orthopedic implants. In one embodiment, the system of the invention may be incorporated into an implantable lead (e.g., a cardiac or neurostimulation lead), provided the lead is compatible with an expandable member, e.g., features a lumen or pocket into which an expandable member is positionable.

Another embodiment of the invention comprises a balloon catheter comprising: a balloon comprising a coating and a therapeutic agent disposed around the outer surface of said balloon; a first outer sheath disposed around said coating; and a second outer sheath disposed around said first outer sheath, wherein said second sheath does not prevent macroscopic wetting of said sheath in an unexpanded state, wherein said first sheath has a microstructure composed of nodes interconnected by fibrils and has characteristics which prevent macroscopic wetting of said sheath in the unexpanded state and when said balloon and sheaths are expanded, said first sheath forms opening which expose sections of the underlying coating and allows rapid transfer of said coating through the outer sheath. In an embodiment, said first sheath is configured to split or tear to form openings. In another embodiment, said first sheath can be folded or otherwise configured onto the balloon in such a way that a plurality of openings is not exposed through the thickness until inflated. In one embodiment, said coating is transferred through said second sheath and onto or into a target tissue. In one embodiment, upon expansion said coating is transferred through said second sheath in a hydrated or partially hydrated state. In another embodiment, said coating remains substantially adhered to the target tissue for greater than 1 minute after contact between balloon and treatment site is substantially eliminated. In another embodiment, said sheaths undergo microscopic wetting in a vessel while said balloon and sheaths are in the unexpanded state and being delivered to a desired location within a vessel. In an embodiment, said transfer of the hydrated or partially hydrated coatings is facilitated when said second sheath is in contact with a vessel wall. In another embodiment, said first sheath comprises a fluoropolymer. In another embodiment, said second sheath also comprises a fluoropolymer. In another embodiment, said nodes are aligned longitudinally to the longitudinal axis of said balloon catheter and said fibrils are aligned circumferentially to said axis. In another embodiment, said nodes are aligned circumferentially to the longitudinal axis of said balloon catheter and said fibrils are aligned longitudinally to said axis. In another embodiment, said first sheath comprises ePTFE. In another embodiment, said coating comprises a hydrophilic component. In another embodiment, said therapeutic agent is a hydrophilic agent. In another embodiment, said therapeutic agent is a hydrophobic agent. In another embodiment, said therapeutic agent is paclitaxel. In another embodiment, said balloon further comprises a structural layer. In another embodiment, said structural layer comprises said coating and therapeutic agent.

It is contemplated that a plurality of described embodiments can be attached to a single catheter to facilitate a plurality of drug delivery events or dosages can be delivered with the use of a single device. In the case of a balloon embodiment, a catheter can comprise discrete inflation lumens for each balloon, or some other mechanism for limiting and controlling the inflation to a particular balloon.

Optionally, described embodiments can be configured to apply therapeutic vibrational energy, radiofrequency energy, or the like to enhance drug delivery. Similarly, iontophoresis can be used to aid in the transfer of the therapeutic agent across the outer sheath and into surrounding tissue. In various embodiments, the pressure levels within the expandable member can be pulsed to create multiple, increased pressure events, which can facilitate transfer of the therapeutic agent and/or create multiple drug delivery events.

Other embodiments of the invention comprise a hydrophilic coating comprising at least one therapeutic agent applied to at least a portion of the exterior surface of an expandable catheter, stent, stent-graft, or blood vessel graft over which is placed an outer sheath with a variably permeable microstructure. During delivery or when the expandable catheter, stent, stent-graft, or blood vessel graft is exposed to a body fluid, microwetting of the coating occurs. Upon expansion of the catheter, stent, stent-graft or graft, the outer sheath disposed over the expandable device transforms from a closed microstructure to an open microstructure and a hydrated or partially hydrated coating is transported outward. In an embodiment, the coating can be located on the proximal and distal sections of the expandable catheter, stent, stent-graft, or blood vessel graft, e.g., to help decrease the incidence of or prevent edge restenosis.

In another embodiment, the expandable medical device of the invention is combined with an occlusion device such as a balloon located proximate the device. Said occlusion device may mitigate the movement of drug far from the treatment site. In one embodiment, the bodily fluids isolated by this system may be withdrawn from the body by aspiration prior to removal of the system.

Another embodiment of the invention comprises a kit comprising a structural layer comprising a dehydrated or partially dehydrated coating (further comprising a therapeutic agent) and an outer sheath over said structural layer. Such a kit can convert an off the shelf balloon catheter or a catheter into an agent eluting construct of the invention. In a further embodiment, said kit comprises an adhesive (including tapes and liquid adhesives) for bonding said structural layer and outer sheath to a balloon catheter or catheter. In another embodiment, said structural layer, outer sheath and adhesive are sterile, placed in a container with an instruction pamphlet explaining how to apply said structural layer and outer sheath onto said balloon catheter. In another embodiment, said balloon catheter is also sterile.

Another embodiment of the invention comprises a PTA or PTCA balloon catheter sheath that extends along a substantial length of the catheter. The sheath at a distal portion comprises a structural layer, drug coating, and an outer sheath about the PTA or PTCA balloon catheter sheath at the location of the PTA or PTCA balloon.

Another embodiment of the invention comprises a medical device comprising a mass transport barrier and a solubilized therapeutic agent, wherein said mass transport barrier has a first configuration that is substantially permeable to bodily fluids and impermeable to the solubilized therapeutic agent and a second configuration, that is substantially permeable to the solubilized therapeutic agent but impermeable to particles greater than about 25 µm. In one embodiment, said a mass transport barrier is treated with a wetting agent, as described above.

Another embodiment the invention comprises a method of delivering a bioactive agent to biological target through a mass transport barrier, said method comprising a mass transport barrier and a solubilized therapeutic agent, wherein said mass transport barrier has a first configuration that is substantially permeable to bodily fluids and impermeable to the solubilized therapeutic agent and a second configuration that is substantially permeable to the solubilized therapeutic agent but impermeable to particles greater than about 25 µm, wherein upon of an application of mechanical force to the mass transport barrier induces the change between the first and second configurations thereby allowing controlled permeation of the solubilized therapeutic agent through the mass transport barrier. In one embodiment, said a mass transport barrier is treated with a wetting agent, as described above.

Due to the toxicity of some of the drugs delivered, it is important to deliver therapeutic agents to a specific target. In addition, if several areas are to be targeted for therapeutic agent delivery, the problem of overlapping treatment (i.e., areas that may get several doses of a therapeutic agent) and the need to swap multiple drug eluting balloon catheters can be of major concern. One way to overcome these deficiencies is shown in FIGS. 9A and 9B. FIG. 9A illustrates a catheter that can be tracked to a targeted area and also be expanded by an expandable device, such as a medical balloon. Catheter 2000 comprises tip 2003 that interfaces with guidewire 2011. Guidewire 2011 may further comprise guidewire stop 2007. Guidewire stop 2007 can engage with tip 2003 and allow the catheter to be tensioned for better balloon tracking. Catheter 2000 further comprises uncoated section 2100, a coated section 2200, and a stiffer tube section 2300. FIG. 9A further depicts a balloon catheter with a balloon 2004 at the distal end of said balloon catheter. Said balloon catheter with balloon 2004 can be placed inside said catheter 2000. Stiffer tube section 2300 allows for said balloon catheter to be more easily inserted into catheter 2000.

FIG. 9B depicts a cross section at line A-A of coated section 2200. FIG. 9B depicts a distensible layer 2040 (similar to the structural layer described above), a coating (comprising a therapeutic agent) 2050, outer sheath 2020 and guidewire 2011.

Figure 9C:
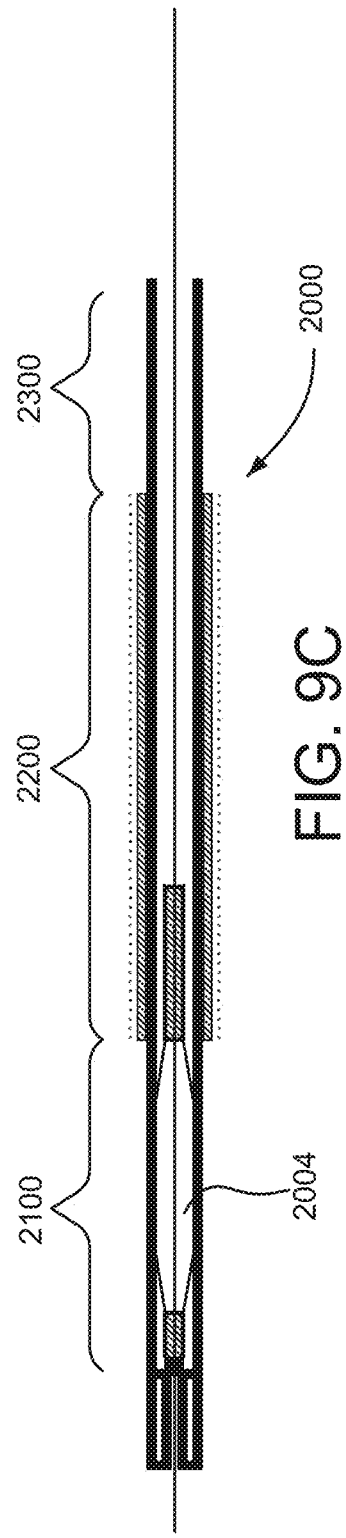
Figure 9D:
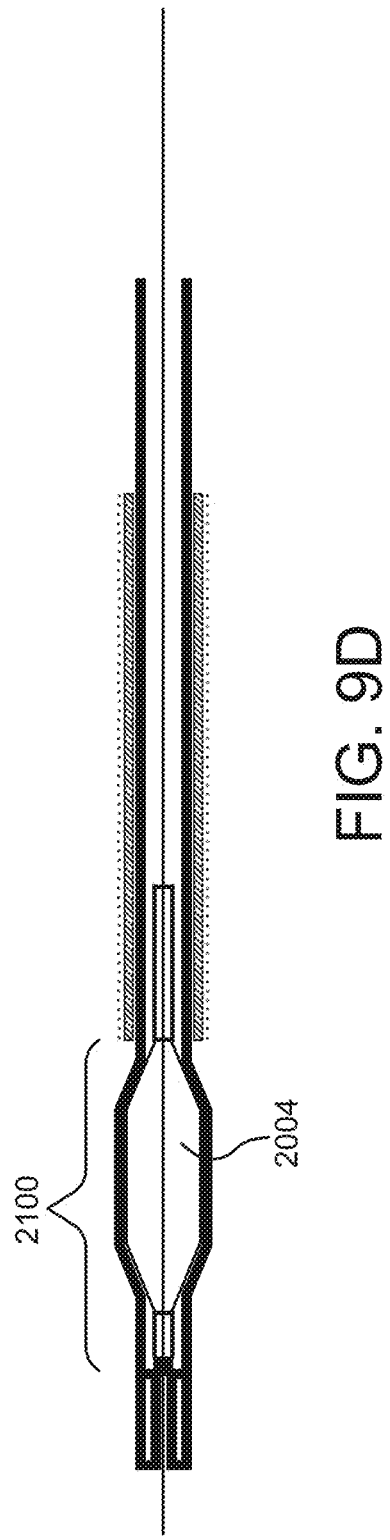

FIGS. 9C through 9F depict the procedural steps for one method of use employing this embodiment. Catheter 2000 is tracked and placed in a targeted vessel for treatment. Then balloon 2004 is tracked into catheter 2000 to a desired location within catheter 2000, as depicted in FIG. 9C. In one embodiment, balloon 2004 is tracked and inflated in uncoated section 2100 to deliver a standard Percutaneous Transluminal Angioplasty (PTA) treatment, as depicted in FIG. 9D. Then, balloon 2004 is deflated after PTA, catheter 2000 is advanced distally to position coated section 2200 at the PTA site and balloon 2004 is repositioned under coated section 2200, as depicted in FIG. 9E. Then, balloon is inflated in coated section 2200, as depicting in FIG. 9F. This will facilitate delivery of a therapeutic agent and/or coating to the vessel. In another embodiment, said balloon is deflated, repositioned to another area of coated section to deliver another dose of a therapeutic agent. In another embodiment, to aid visualization by the clinician, radiopaque or other imaging markers are incorporated in catheter 2000 and/or balloon catheter 2004. In another embodiment, several doses can be delivered to different areas in a vessel by repositioning balloon 2004 and/or catheter 2000. The mechanisms by which the catheter is made, the coating and therapeutic agent are loaded and delivered are described above. In another embodiment, said catheter comprises an elastomeric element (as described above) so that after balloon inflation catheter 2000 can recompact to or near to its delivery diameter.

Thus, one embodiment of the invention comprises a system of delivering a therapeutic agent comprising, a catheter comprising a distensible layer, a coating comprising a therapeutic agent disposed around said distensible layer, and an outer sheath over said distensible layer and said coating; wherein said outer sheath has a variably permeable microstructure that prevents unintended transfer of therapeutic agent through said outer sheath, a medical balloon catheter, wherein said medical balloon is on the distal end of a catheter; wherein said medical balloon can be placed with said catheter; and wherein when said medical balloon is inflated in said catheter, it will distend said distensible layer and outer sheath allowing rapid transfer of said coating and therapeutic agent to an area external to said outer sheath. In one embodiment, said outer sheath prevents the transfer of particles out of said sheath greater than about 25 microns in size. For example, the maximum effective pore size of the microstructure at second diameter is less than or equal to about 25 microns. In other embodiments, particles greater than about 25 microns in size can transfer through said sheath. In another embodiment, said outer sheath rapidly wets out during expansion and allows rapid transfer of said coating and therapeutic agent. In another embodiment, said sheath undergoes microscopic wetting in a vessel while said balloon and sheath are in the unexpanded state and being delivered to a desired location within a vessel. In another embodiment, said sheath comprises a wetting agent and will wet out completely when in contact with fluid in a first diameter. In another embodiment, said coating hydrates when said outer sheath is in a first diameter. In another embodiment, said outer sheath comprises a fluoropolymer. In another embodiment, said outer sheath comprises ePTFE. In another embodiment, said hydrophobic agent is selected from the group consisting of taxane domain-binding drugs, such as paclitaxel, and rapamycin. In another embodiment, said coating comprises at least one hydrophilic component selected from the group consisting of benzethonium chloride, PEG, poloxamer, sodium salicylate, and hydroxypropyl-β-cyclodextrin.

Figure 10A:
FIGS. 10A to 10G depict drug eluting sleeve construct that can be used to deliver therapeutic agents.
Figure 10B:
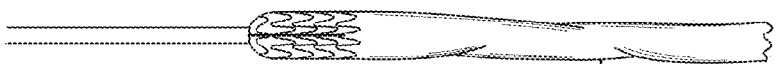
Figure 10C:
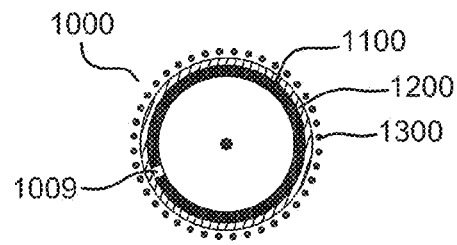

Another similar embodiment that can reduce the need to swap multiple devices and can be useful treating a tortuous length of vessel can comprise a drug eluting sleeve with a expandable member disposed within the sleeve and slideable along the length of the sleeve. The expandable member can expand and contract along the length of the sleeve and/or can be slideably retracted or advanced while remaining in the expanded state. FIGS. 10A and 10B illustrate a proximal end of a drug eluting sleeve 1000 that can be tracked to a targeted area and can also be expanded along a section by an expandable device, such as a medical balloon. FIG. 10C illustrates a cross-section of said sleeve 1000. Said sleeve 1000 comprises a structural layer 1100, a coated section 1200, and optionally, an outer sheath 1300. Said sleeve 1000 is an elongated flexible form having a lumen extending there through. The expandable member can be axially relocated along the length of the lumen. In an embodiment, at its proximal or distal end, said sleeve 1000 can also comprise a self-expanding annular frame 1300, e.g., a small self-expanding stent frame. The frame is constructed to hold the sleeve open, which can facilitate entry of balloon 1004 into the lumen of the sleeve and/or permit blood to flow into the lumen of the sleeve 1000 to fill sleeve such that sleeve presses against the vessel wall. Furthermore, in an embodiment where the self expanding annular frame 1300 is larger than the sleeve 1000 to facilitate contact with the surrounding vessel, the self-expanding annular frame 1300 can be utilized to facilitate distal-to-proximal deployment whereby the distal annular frame 1300 is seated to the vessel wall while the devices is retracted proximally to unfurl, reduce wrinkling, and/or reduce bunching of said sleeve 1000 (alternatively, proximal-to-distal deployment could be achieved in the same fashion). Additionally, the self expanding annular frame 1300 may extend along the full length of the device to facilitate full opening and unfurling of said sleeve 1000, and decrease the propensity for wrinkling, bunching or kinking of said sleeve 1000. Blood flow into the lumen can also be useful for wetting the underside of the coating. For example, said sleeve 1000 comprises a wettable or wickable structural layer 1100 as the base layer.

Figure 10D:
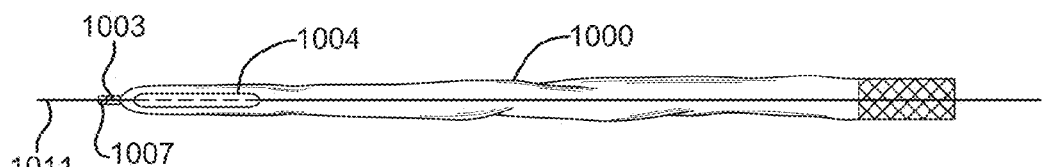

In an embodiment, with reference to FIG. 10D, said sleeve 1000 can comprise tip 1003 that interfaces with guidewire 1011. Guidewire 1011 may further comprise guidewire stop 1007. Guidewire stop 1007 can engage with tip 1003 and allow the sleeve 1000 to be tensioned for better positioning or balloon tracking. In an embodiment, a balloon catheter with a balloon 1004 at the distal end of said balloon catheter can be placed inside said sleeve 1000, and slide axially along the length of the sleeve 1000, inflating and deflating to press firmly the sleeve against the surrounding tissue and deliver a therapeutic agent to a desired area. Optionally, balloon 1004 can remain inflated and slide axially along the length of the sleeve in an inflated state. In an embodiment, balloon 1004 deliver a standard Percutaneous Transluminal Angioplasty (PTA) treatment.

To ensure said sleeve 1000 is properly positioned along the length of a vessel and to prevent potential bunching of said sleeve 1000, said sleeve 1000 can comprise an inflatable lumen or a guidewire lumen 1009 located within the sidewall of the sleeve 1000 in order to increase its relative rigidity to facilitate proper device placement, as shown in FIG. 10C. The inflatable lumen 1009 is in fluid communication with a catheter hub and can receive a pressurized fluid that helps to unfurl, reduce wrinkling, and/or reduce bunching of said sleeve.

Similarly, in an embodiment, a delivery catheter circumscribing said sleeve 1000 can be used to track said sleeve 1000. Once in position, delivery catheter is retracted.

In another embodiment, as depicted in FIG. 10D, a distal section of the sleeve can be coupled to the balloon catheter on the distal side of the balloon 1004. Thus, as the balloon 1004 retracts along the guidewire, it will invert the spent section of sleeve.

In a further embodiment, to aid visualization by the clinician, radiopaque or other imaging markers are incorporated in sleeve 1000 and/or balloon catheter. In another embodiment, several doses can be delivered to different areas in a vessel by repositioning balloon 1004 and/or sleeve 1000. The mechanisms by which the sleeve is made, the coating and therapeutic agent are loaded and delivered are described herein.

Figure 10E:
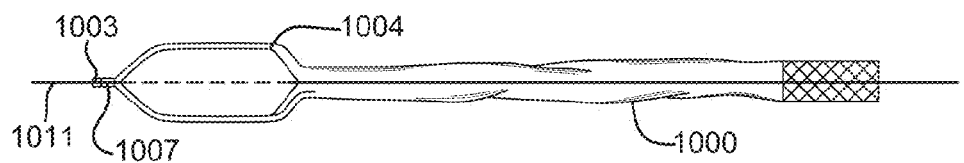
Figure 10F:
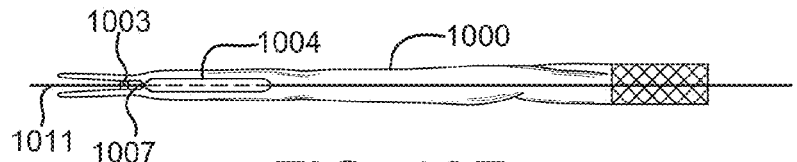
Figure 10G:
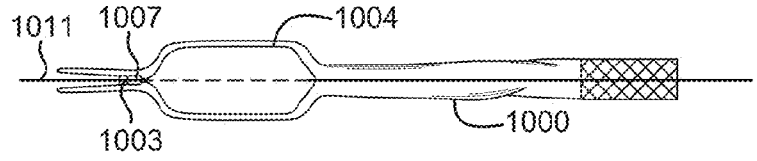

FIGS. 10D to 10G depict the procedural steps for one method of use employing a drug eluting sleeve embodiment. Said embodiment comprising a drug eluting sleeve 1000 having a balloon 1004 located within the distal end of the sleeve is tracked in a distal direction and placed in a targeted vessel for treatment. In an embodiment, self-expanding annular frame expands and blood can flow into the sleeve. In one embodiment, balloon 1004 is inflated to press a first section of said drug eluting sleeve 1000 against the vessel wall, as depicted in FIG. 10E. This will facilitate delivery of a therapeutic agent and/or coating to the vessel about the first section of said sleeve 1000. Then, balloon 1004 is at least partially deflated and retracted a distance such that balloon is located along a second section of said sleeve 1000, as depicted in FIG. 10F. Balloon 1004 is then reinflated to press a second section of said drug eluting sleeve 1000 against the vessel wall, as depicted in FIG. 10G. This can be repeated to a third section, fourth section, and so on.

Alternatively, in another embodiment, said balloon 1004 does not deflate to be repositioned, but instead, slides in a proximal or distal direction along the length of the sleeve in an inflated state, pressing the drug eluting sleeve 1000 against the vessel wall in a continuous fashion. In an embodiment, to facilitate this sliding retraction or advancement while balloon is inflated, the inner face of the sleeve and/or the outer surface of said balloon 1004 can comprise a lubricious surface or coating.

This technique of utilizing the pressure of the expandable member 1004 to release therapeutic agents across a single sleeve 1000 allows for longer devices to be utilized to treat shorter segments as needed. This would allow a sleeve 1000 that could be 20 cm to be tailored to treat a diseased tissue segment that is only 18 cm. Furthermore, the vessel diameter range treated by a single sleeve 1000 would be dependent upon the expandable member diameter chosen by the operator allowing a greater range of vessel diameters treated by the single sleeve 1000. That is to say, a device measuring 4 mm in diameter could be used to treat 4 mm, 5 mm, 6 mm or greater diameters depending upon technical specifications.

Thus, one drug eluting sleeve embodiment comprises a system of delivering a therapeutic agent comprising, a flexible sleeve comprising a structural layer, a coating comprising a therapeutic agent disposed on the outer surface of said structural layer, and optionally, an outer sheath over said sleeve and said coating; wherein said outer sheath has a variably permeable microstructure that prevents unintended transfer of therapeutic agent through said outer sheath, a medical balloon catheter, wherein said medical balloon is on the distal end of a catheter; wherein said medical balloon is located at a distal end of said sleeve; and wherein when said medical balloon is inflated in said sleeve, it will distend said sleeve allowing rapid transfer of said coating and therapeutic agent to an area external to said outer sheath. In one embodiment, said outer sheath prevents the transfer of particles out of said sheath greater than about 25 microns in size. For example, the maximum effective pore size of the microstructure at second diameter is less than or equal to about 25 microns. In other embodiments, particles greater than about 25 microns in size can transfer through said sheath. In another embodiment, said outer sheath rapidly wets out during expansion and allows rapid transfer of said coating and therapeutic agent. In another embodiment, said sheath undergoes microscopic wetting in a vessel while said balloon and sheath are in the unexpanded state and being delivered to a desired location within a vessel. In another embodiment, said sheath comprises a wetting agent and will wet out completely when in contact with fluid in a first diameter. In another embodiment, said coating hydrates when said outer sheath is in a first diameter. In another embodiment, said outer sheath comprises a fluoropolymer. In another embodiment, said outer sheath comprises ePTFE. In another embodiment, said hydrophobic agent is selected from the group consisting of taxane domain-binding drugs, such as paclitaxel, and rapamycin. In another embodiment, said coating comprises at least one hydrophilic component selected from the group consisting of benzethonium chloride, PEG, poloxamer, sodium salicylate, and hydroxypropyl-β-cyclodextrin.

While particular embodiments of the present invention have been illustrated and described herein, the present invention should not be limited to such illustrations and descriptions. It should be apparent that changes and modifications may be incorporated and embodied as part of the present invention within the scope of the following claims. The following examples are further offered to illustrate the present invention.

EXAMPLES

Example 1

Preparation of a Structural Cover

A structural cover was prepared using methods as essentially taught in U.S. Pat. No. 6,120,477 (Campbell, et al.). A film tube was made by helically wrapping 20 layers of a highly fibrillated 5 micron thick ePTFE film (U.S. Pat. No. 5,476,589 to Bacino) at an 83.4° angle to the tubular axis on a 7 mm stainless steel mandrel. Ten layers of the ePTFE were wrapped in one direction and ten layers were wrapped in the opposing direction. The mandrel was baked in an oven set at 380° C. for 6 minutes to fuse the layers together. The resulting tube was removed from the mandrel and "necked" (axially stretched) down to a diameter below 2.2 mm. This necked tube was placed onto a 2.2 mm stainless steel mandrel and overwrapped with approximately 5 layers of a sacrificial ePTFE film to prevent the tube from wrinkling in the subsequent steps. Next, the tube construct was uniformly compressed to approximately 65% of its original length. The construct was placed in an oven set at the 380° C. for 1 minute and then the sacrificial ePTFE layer was removed. This construct was removed from the mandrel and cut to a 65.0 mm length. In alternate embodiments, this structural layer may comprise an elastomer to aid in recompaction of the underlying balloon (see, e.g., U.S. Pat. No. 6,120,477, Campbell, et al.).

Example 2

Assembly of a Structural Cover onto a Balloon Catheter

A semicompliant balloon catheter was purchased from Bavaria Medizin Technologie, Oberpfaffenhofen, Germany (model #BMT-035, article #08PL-604A, with balloon dimensions of 6.0 mm×40 mm). The balloon has the following specifications: a nylon balloon with a 6 atmosphere (atm) nominal inflation pressure and a 14 atm rated burst pressure, a 6 mm nominal diameter, 40 mm balloon working length, mounted on a 0.9 mm guidewire compatible catheter.

The structural tube, as described in Example 1, was centered over the semicompliant balloon and the ends were wetted with a Loctite 7701 primer (Henkel AG & Co. KgaA, Düsseldorf, Germany). The ends were then fixedly attached to the catheter using five layers of a 6.4 mm width of ePTFE film which were wrapped circumferentially around the balloon ends while Loctite 4981 (Henkel AG & Co. KgaA, Düsseldorf, Germany) was applied to the film.

The structural cover was colored black using a Sharpie® permanent marker (Sanford Corporation, Oak Brook, Ill.). The coloring of the structural cover was used to show the extent of outer sheath wetting, as described in more detail below. The structural tube is also known herein as the "structural cover", especially when it is placed and secured over a balloon.

Example 3

Application of a Hydrophilic Coating to a Structural Cover

A 5% (by weight) aqueous solution of polyvinyl alcohol (PVA, USP grade, Spectrum Chemicals & Laboratory Products, Gardena, Calif.) was prepared. This solution is referred herein as Solution 3. A structural tube was assembled onto a balloon catheter as described in Example 2, and was dip-coated with Solution 3 for 30 seconds while rotating. After the 30 seconds, the device was removed from Solution 3. While rotating the device, a heat gun was used to blow warm air (of about 40° C.) over the device for approximately 3 minutes. This process was then repeated two additional times. Next, the device was placed into an oven set at 60° C. for approximately 10 minutes.

The resulting coated structure had an outer diameter (OD) of less than 3.2 mm.

Example 4

Preparation of an Outer Sheath

An outer sheath layer was prepared using the following method. A film tube was created by helically wrapping four layers of a thin ePTFE film (as described in U.S. Pat. No. 5,814,405 Branca et al.) at a 75° angle to the tubular axis on a 6 mm stainless steel mandrel. Two layers of the ePTFE were wrapped in one direction and two layers are wrapped in the opposing direction. The mandrel comprising the ePTFE layers was baked in an oven set at 380° C. for 6 minutes to fuse the layers together. The resulting tube was removed from the mandrel and necked down to a diameter below 3.2 mm. This necked tube was stretched up by slipping the tube onto a 3.2 mm stainless steel mandrel. The tube was then overwrapped with approximately five layers of a sacrificial ePTFE film to prevent wrinkling during the subsequent step. Next, the tube construct was uniformly compressed to approximately 90% of its original length. The construct was then placed in an oven set at 380° C. for 1 minute. After baking the construct, the sacrificial ePTFE layer was removed. The tube construct was then removed from the mandrel and cut to a 65 mm length to form the outer sheath layer.

Example 5

Assembly of an Outer ePTFE Sheath onto a Coated Balloon Catheter

The outer sheath layer, as prepared in Example 4, was then centered over the coated section of the balloon described in Example 3 and the ends were wetted with a Loctite 7701 primer (Henkel AG & Co. KgaA, Düsseldorf, Germany). The ends of the outer sheath layer were then fixedly attached to the balloon using five layers of a 6.4 mm width of ePTFE film. Specifically, the ePTFE film layers were wrapped circumferentially around the balloon ends while Loctite 4981 (Henkel AG & Co. KgaA, Düsseldorf, Germany) was applied to the film.

Example 6

Assembly of an Outer Sheath onto an Uncoated Balloon Catheter

The outer sheath layer, as prepared in Example 4, was centered over the uncoated section of the balloon described in Example 2 and the ends were wetted with a Loctite 7701 primer (Henkel AG & Co. KgaA, Düsseldorf, Germany). The ends of the outer sheath layer were then fixedly attached to the balloon using five layers of a 6.4 mm width of ePTFE film. Specifically, the ePTFE film layers were wrapped circumferentially around the balloon ends while Loctite 4981 (Henkel AG & Co. KgaA, Düsseldorf, Germany) was applied to the film.

Example 7

Methods for Characterizing In Vitro Wetting of Balloon Catheters in Blood

As described above, wetting is the displacement of air by a fluid in an ePTFE structure. It is known to those skilled in the art that ePTFE that is not wet by a fluid is white or opaque in appearance. It is also known to those skilled in the art that ePTFE that is macroscopically wet by a fluid is translucent in appearance. Accordingly, if the outer sheath of a balloon catheter, as prepared in Example 4, has been wet by blood, or another fluid, the outer sheath will become translucent and the underlying structural cover (previously colored black, see Example 2) will become visible.

The test methods described below were used to test wetting of the balloon cover. Specifically, the test described below was used to determine the degree of wetting of the outer sheath of an agent eluting construct after placement in blood at the construct's first state (unexpanded state) and the degree of wetting of the outer sheath after pressurization (expanded state) and contact with a mock vessel wall.

Blood was harvested from a canine, citrated to prevent clotting, and placed into a 50 ml vial. A balloon catheter construct was fully submerged in the canine citrated blood in its deflated state (first state) for 20 minutes. After 20 minutes, the balloon was removed and fully rinsed with saline.

The balloon construct was visually inspected for signs of wetting of the outer sheath. Pictures were taken, and results were noted as "degree of wetting at first state". Visual signs of sheath wetting include the appearance of black regions along the balloon. These black regions become apparent as the outer sheath wets and becomes translucent, allowing for visualization of the underlying black structural cover. A subjective rating scale was used to designate the degree of wetting where a completely wet sheath would be a '10' and fully non-wet sheath would be a '0'. Partial wetting earned a rank correlating to the degree of wetting.

After ranking, the same balloon catheter was placed into a 5.9 mm diameter rigid tube (70 mm in length) submerged in the canine citrated blood. The balloon catheter (which has a nominal inflation diameter of 6 mm) was then inflated to 6 atm for 1 minute. At this pressure, the balloon catheter achieved full apposition against the rigid tube's wall. After a 1 minute inflation period, the balloon catheter was deflated, removed from the tube, and rinsed with saline. After rinsing, the balloon catheter was photographed, and re-inflated to 6 atm and visually inspected.

Pictures were taken, and results were noted as degree of wetting at 6 atm inflation as described above.

The balloon catheter was then reinserted into the 5.9 mm diameter rigid tube (70 mm in length) submerged in the canine citrated blood. The balloon catheter (which has a nominal inflation diameter of 6 mm) was then inflated to 12 atm for 1 minute. At this pressure, the balloon catheter achieved full apposition against the rigid tube's wall. After the 1 minute inflation period, the balloon catheter was deflated, removed from the tube, and rinsed with saline. After rinsing, the balloon catheter was photographed, re-inflated to 12 atm and visually inspected.

Pictures were taken, and results were noted as degree of wetting at 12 atm inflation.

Example 8

Effect of Hydrophilic Coating on Outer Sheath Wetting in Blood with Vessel Contact A PVA coating was applied to a structural cover on a balloon catheter (as described in Example 3). This balloon catheter is herein referred to as Device 8a. The structural cover of the second balloon catheter (herein referred to as Device 8b) was left uncoated.

Outer sheaths were prepared as described in Example 4. An outer sheath was then assembled onto Device 8a as described in Example 5. An outer sheath was then assembled onto Device 8b as described in Example 6.

Devices 8a and 8b underwent testing for in vitro blood wetting according to the methods described in Example 7. The results of this experiment are detailed in Table 1 and FIGS. 11 through 13.

TABLE 1

Degree of Wetting of Balloon Catheters with and without a Hydrophilic Coating

| Degree of Wetting | Device 8a (with hydrophilic coating) | Device 8b (without hydrophilic coating) |
| --- | --- | --- |
| at first state | 1 | 1 |
| at 6 atm inflation | 5 | 2 |
| at 12 atm inflation | 10 | 3 |

As shown in FIG. 11 and in Table 1, when Device 8a (FIG. 11A) and Device 8b (FIG. 11B) were submerged in blood in an unexpanded state, the outer sheaths of these devices did not substantially wet and did not become translucent. Therefore, the colored (black) structural cover below the outer sheath was not visible through the outer sheath.

Figure 12A:
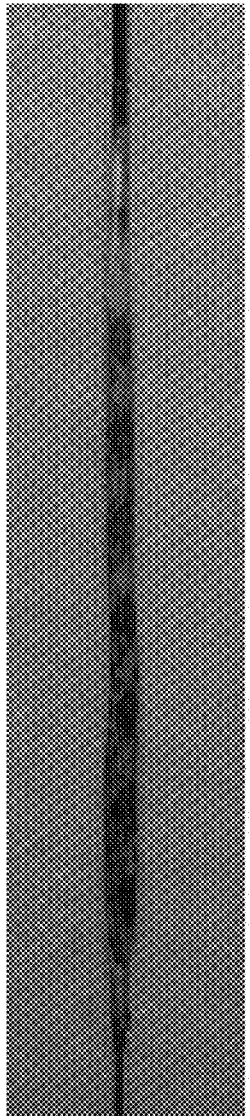
FIGS. 12A and 12B depict degree of wetting of a device with a hydrophilic coating (Device 8a, FIG. 12A) and a device without a coating (Device 8b, FIG. 12B) after being submerged in blood and expanded within a rigid tube (serving as a mock vessel) to a pressure of 6 atmospheres for 1 minute and then deflated and rinsed.
Figure 12B:
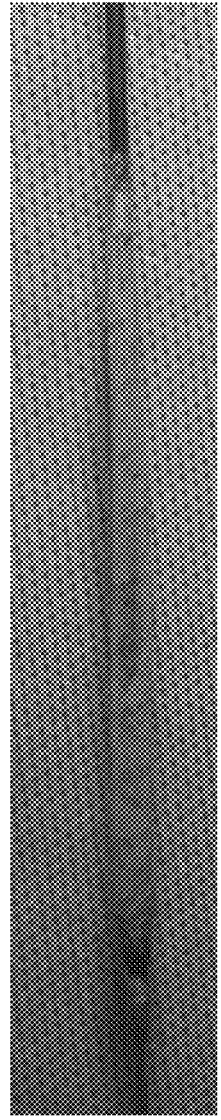
Figure 13A:
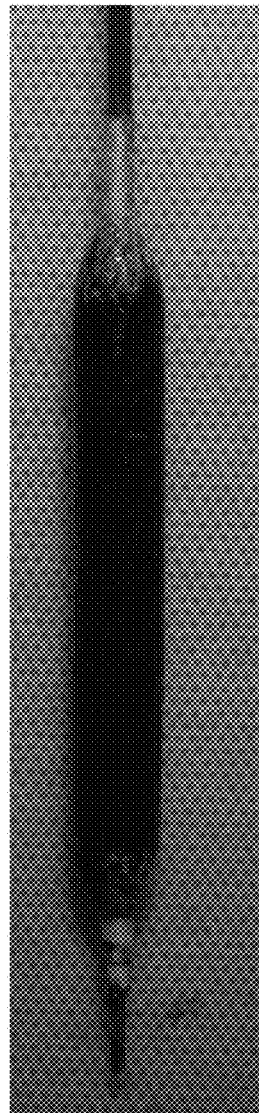
FIGS. 13A and 13B depict degree of wetting of a device with a hydrophilic coating (Device 8a, FIG. 13A) and a device without a coating (Device 8b, FIG. 13B) after being submerged in blood and expanded in a rigid tube to a pressure of 12 atm.
Figure 13B:
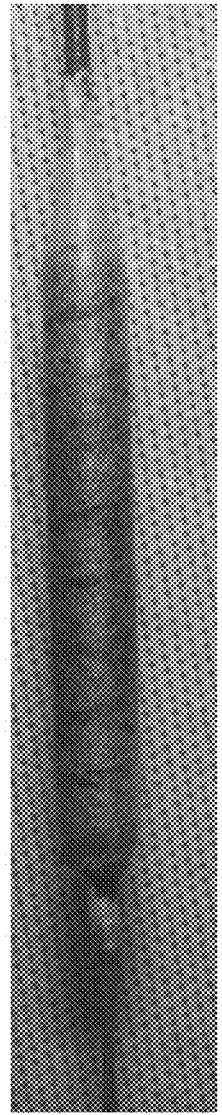

As shown in FIG. 12 and in Table 1, when Device 8a (FIG. 12A) and Device 8b (FIG. 12B) were submerged in blood and expanded to a pressure of 6 atm (as described above), the outer sheath on Device 8a underwent substantial wetting whereas the outer sheath on Device 8b was only partially wetted.

As shown in Table 1, when Device 8a (FIG. 13A) and Device 8b (FIG. 13B) were submerged in blood and expanded to a pressure of 12 atm (as described above), the outer sheath of Device 8a underwent complete wetting whereas the outer sheath of Device 8b was incompletely wet. Thus, these data suggest that the hydrophilic coating of Device 8a aids in rapid cover wetting.

Example 9

Effect of Vessel Contact on the Extent of In Vitro Balloon Catheter Wetting

The experiment described herein was used to determine the effect of vessel contact on balloon catheter wetting.

Figure 14A:
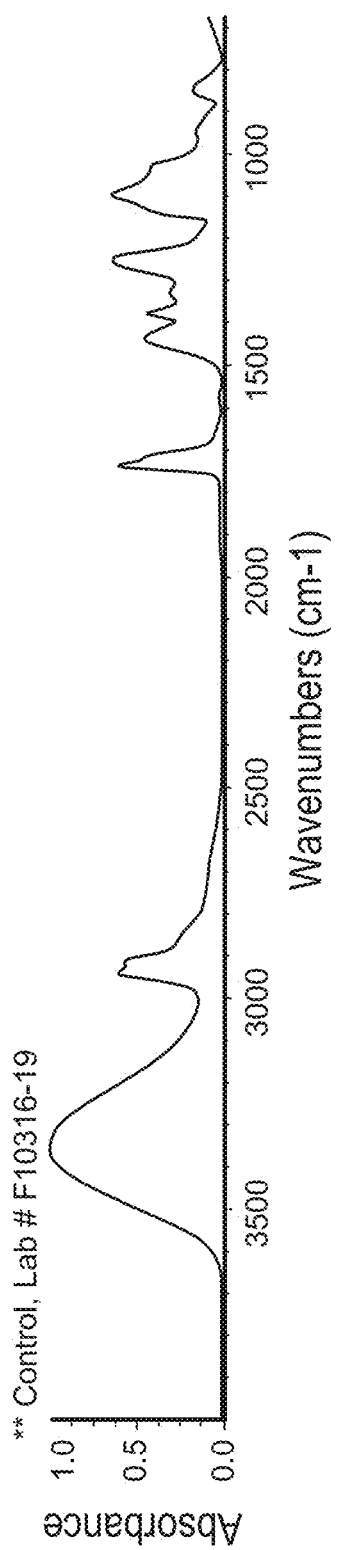
FIGS. 14A and 14B depict Fourier Transform Infrared Spectroscopy (FTIR) interferograms of the PVA coating applied to Device 9 (FIG. 14A) and released from Device 9 after expansion (FIG. 14B).

A coating containing PVA (i.e., a hydrophilic coating) was applied to a structural cover (as described in Example 3). A sample of the solution used in the coating process was analyzed by Fourier Transform Infrared Spectroscopy (FTIR). FIG. 14A is the interferogram of this analysis. An outer sheath (as prepared in Example 4) was placed onto the balloon catheter (as described in Example 5). This balloon catheter construct is herein referred to as Device 9. Device 9 underwent testing for in vitro blood wetting according to the method described below.

Blood was harvested from a canine, citrated to prevent clotting, and placed in a 50 ml vial. Device 9 was fully submerged in the blood at first state (unexpanded) for 20 minutes. After 20 minutes, Device 9 was removed from the blood, fully rinsed with saline, and photographed (FIG. 15A)

Device 9 (which has a nominal inflation diameter of 6 mm) was again submerged in the blood and was inflated to 12 atm for 1 minute. After the 1 minute inflation period, Device 9 was deflated, removed from the blood, and rinsed with saline. After rinsing, Device 9 was re-inflated to 12 atm, visually inspected, and photographed (FIG. 15B). Device 9 was then deflated.

Figure 14B:
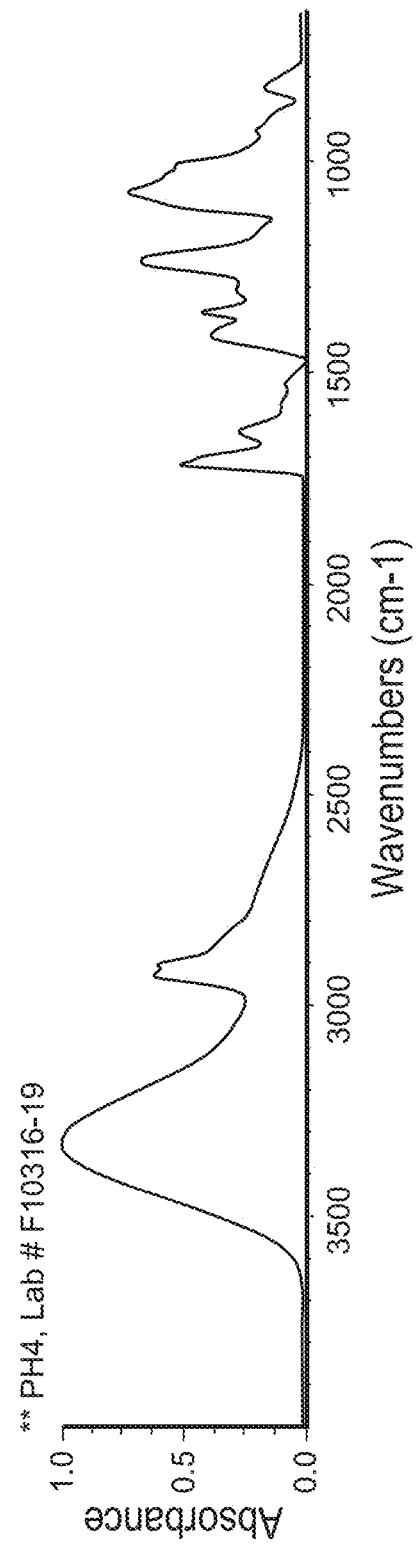

Next, Device 9 was inserted into a 5.9 mm diameter rigid tube (70 mm in length) that was submerged in the canine blood. Device 9 was re-inflated to 12 atm for 1 minute. At this pressure, Device 9 achieved full apposition to the tube's wall. After the 1 minute inflation period, Device 9 was deflated, removed from the blood, and rinsed with saline. After rinsing, Device 9 was re-inflated to 12 atm, visually inspected, and photographed (FIG. 15C). At this time a glass microscope slide was wiped across the outermost surface of Device 9 to collect any coating that had migrated through the outer sheath. The microscope slide was analyzed by FTIR, Fourier Transform Infrared Spectroscopy. FIG. 14B is the interferogram of this analysis. Comparing FIGS. 14A and 14B, the data suggests that PVA from the coating on Device 9 was transported through the outer sheath upon inflation.

Figure 15A:
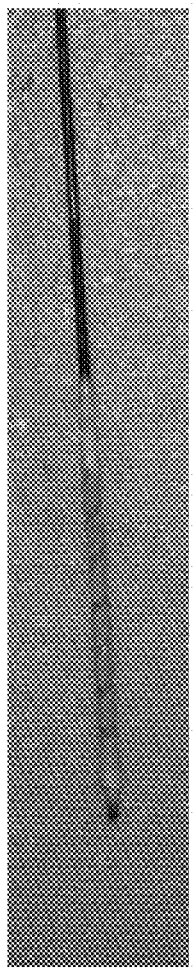
FIGS. 15A through 15C depict degree of wetting of Device 9 when uninflated (FIG. 15A), inflated to 12 atmospheres (atm) in blood without vessel contact (FIG. 15B), and inflated to 12 atm in blood in a rigid tube serving as a mock vessel to provide vessel contact (FIG. 15C).
Figure 15B:
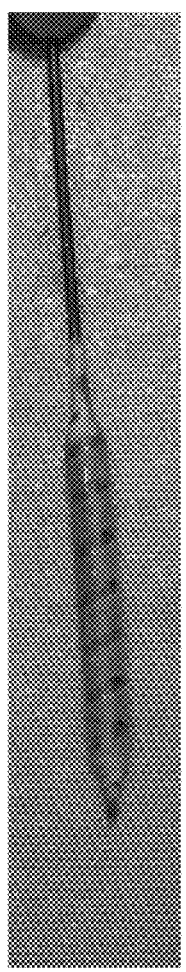
Figure 15C:
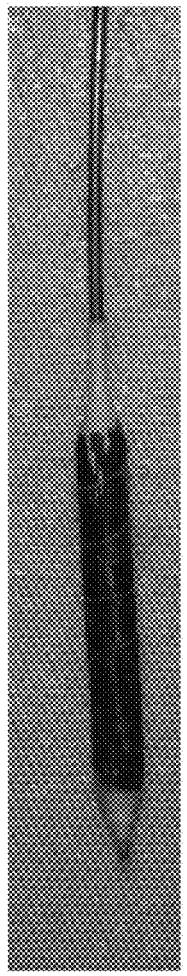

As shown in FIGS. 15A through 15C, the outer sheath of Device 9 underwent more complete blood wetting after contact with the rigid tube, as depicted in FIG. 15C.

Example 10

Effect of an Outer Sheath on Coating Particulation from a Balloon Catheter

The experiment described here characterizes particulation from coated balloon catheters assembled with and without an outer sheath over the coating.

Four structural covers were prepared as described in Example 1. Each structural cover was separately assembled onto a different balloon catheter (as described in Example 2). The structural covers of the four balloon catheters where coated by the method described below.

A 5% (by weight) aqueous solution of PVA (USP grade, Spectrum Chemicals & Laboratory Products, Gardena, Calif.) was prepared. This solution is herein referred to as Solution 10.

Next, the following additives were added to 16.3 g of Solution 10: 3.0 g hydroxypropyl-β-cyclodextrin (Sigma-Aldrich, St. Louis, Mo.), 0.3 g of 2 μm polystyrene microspheres (Polysciences, Warrington, Pa.), 0.3 g of 5 μm polystyrene microspheres (Polysciences, Warrington, Pa.), 0.9 g of 10 μm polystyrene microspheres (Polysciences, Warrington, Pa.), and 0.9 g of 25 μm polystyrene microspheres (Polysciences, Warrington, Pa.). This resulting coating formulation is herein referred to as Formulation 10B.

Next, the balloon catheters with assembled structural covers were dipped into Formulation 10B for 30 seconds while rotating. After the 30 seconds, the devices were removed from Formulation 10B. While rotating the devices, a heat gun was used to blow warm air (about 40° C.) over the devices for approximately 3 minutes. This process was then repeated two additional times. Then the devices were placed into an oven set at 60° C. for approximately 10 minutes.

After coating, two of the balloon catheters were not fit with an outer sheath. These coated, sheath-less, balloon catheters are herein defined as Devices 11C and 11D.

After coating, the other two balloon catheters were fit with outer sheaths. Specifically, two separate outer sheaths were prepared according to Example 4. Then each outer sheath was centered over the coated section of the balloon catheter and the ends were wetted with a Loctite 7701 primer. The ends were then fixedly attached using a reinforcing film wrap. The film wrap comprised five layers of a 6.4 mm width of ePTFE film which were wrapped circumferentially around the balloon ends while Loctite 4981 was applied to the film. The resulting coated balloon catheters with attached outer sheath are herein defined as Devices 11e and 11f.

Next, all four devices were subjected to particulation testing utilizing the method described below.

A 25% (by weight) solution of isopropyl alcohol in water was passed through a 0.2 μm filter and collected in a clean 100 ml graduated glass cylinder. This solution is herein referred to as the collection media. The test device was placed in the graduated cylinder so that the balloon was submerged in the collection media. The device was then immediately inflated to 6 atm for 1 minute. After this time, the device was deflated and immediately removed from the graduated cylinder. Particles in the collection media were then analyzed by an Accusizer Particle Sizer (780/SIS PSS NICOMP, Santa Barbara, Calif. USA) according to test method described by United States Pharmacopeia (USP) monograph 788 for small volume injectables.

As described above two treatment groups were analyzed with a sample size of two per treatment. The treatment groups were: Coated, sheath-less balloon catheters (Devices 11c and 11d); Coated balloon catheters with attached outer sheaths (Devices 11e and 11f).

Figure 16:
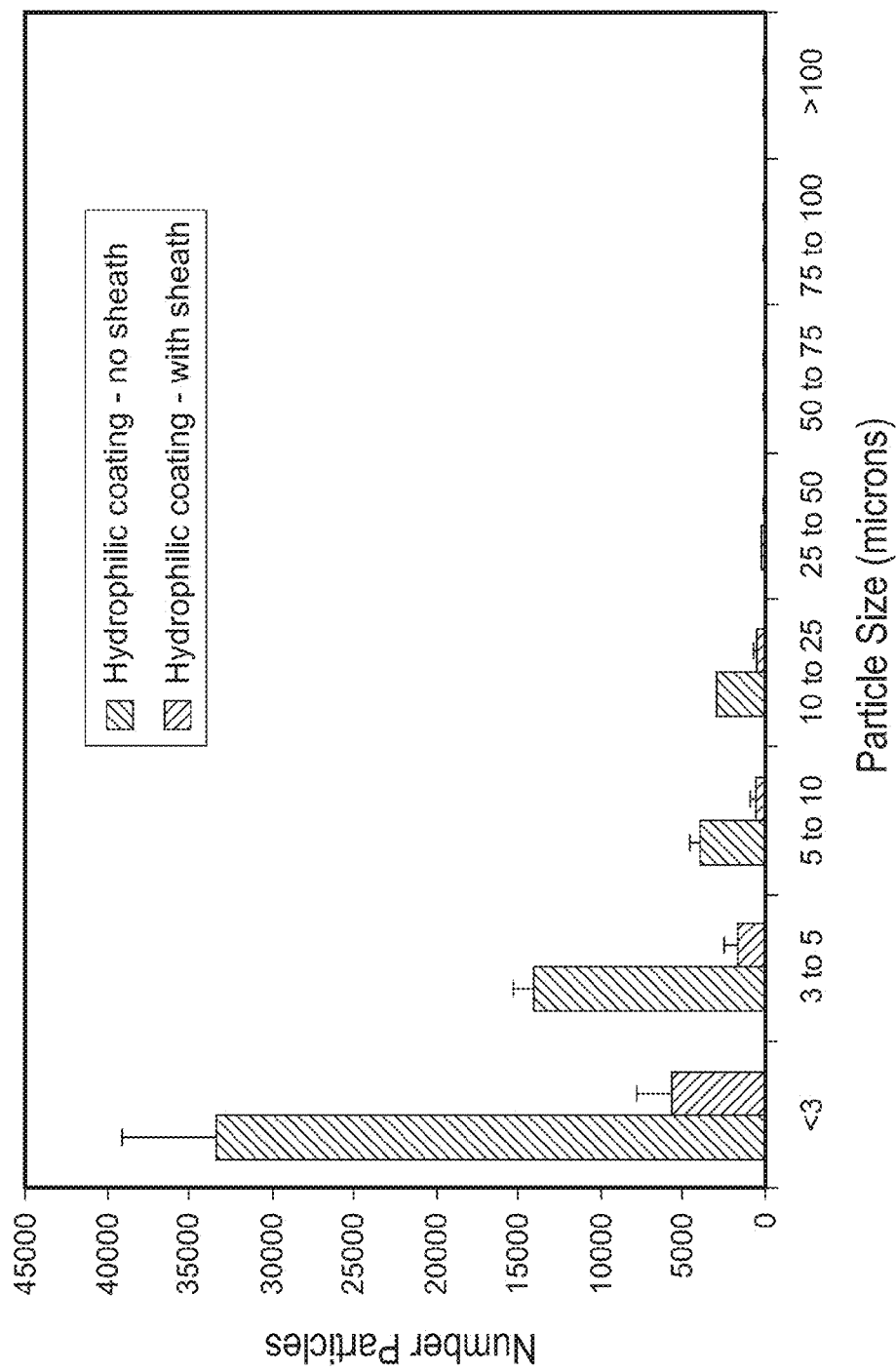
FIG. 16 depicts particulation from coated balloons with and without outer sheaths.

These data are summarized in FIG. 16 as mean particle distributions for the three treatment groups. As shown, the outer sheath reduces particulation of the coated devices.

Example 11

Application of a Texas Red Coating to a Structural Cover

A 5% (w/v) aqueous solution of PVA (USP grade, P1180, Spectrum Chemicals & Laboratory Products, Gardena, Calif.) was prepared. Then, 0.0833 g of dextran (101509, MP Biomedicals, Solon, Ohio) was added to 5 ml of the 5% (w/v) PVA solution. This solution is herein referred to as Solution 11b. Next, 10 mg of Texas-red-labeled-dextran (D3328, Invitrogen, Carlsbad, Calif.) was added to 2 g of the PVA/dextran solution. This solution is herein known as Solution 11c. Solution 11c was vortexed for approximately one minute.

A structural cover was prepared as described in Example 1 and then assembled onto a balloon catheter as described in Example 2. This device was then coated with Solution 11c according to the method described below.

Approximately 0.33 ml of Solution 11c was applied to the device while rotating. The device was then allowed to dry for 10 minutes under warm air. This process was then repeated two additional times. Then the device was allowed to dry overnight at 40° C.

Example 12

Delivery of Texas-Red-Labeled-Dextran to an Explanted Vessel from a Coated Balloon Catheter A cryoprotectant solution was prepared by mixing 100 ml of bovine serum (35022-CV, Mediatech, Manassas, Va.) with 12.8 ml of DMSO (D-8779, Sigma, St. Louis, Mo.) and 3.86 g of sucrose (53928, Sigma, St. Louis, Mo.). Two segments of canine carotid artery were harvested and placed into separate vials containing the cryoprotectant solution. The vials were stored at −20° C. until the time of testing.

A structural cover (as prepared in Example 1) was assembled onto a balloon catheter (as described in Example 2). A hydrophilic coating was then applied to the balloon catheter as described in Example 11. As noted in Example 11, this coating contained a fluorescent molecule (Texas-red-labeled-dextran). An outer sheath layer (previously prepared per Example 4) was then assembled onto the coated balloon catheter (per Example 5). This balloon catheter is herein referred to as Device 12.

At the time of testing, one of the vials containing a segment of cryopreserved artery was thawed. The artery was removed from the vial and submerged in heparinized canine blood (37° C.).

Figure 17A:
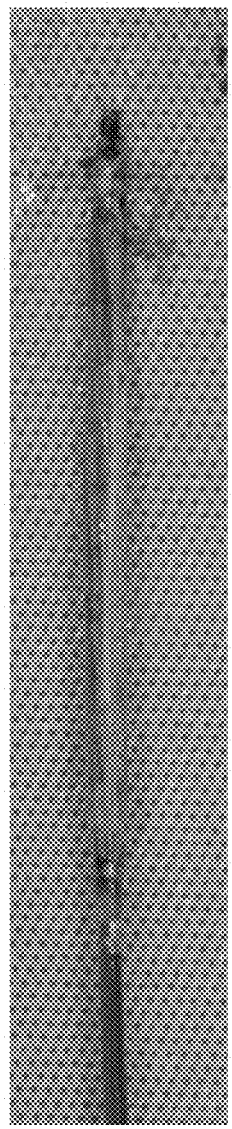
FIGS. 17A and 17B depict degree of wetting of Device 12 that was left unexpanded (FIG. 17A) and expanded inside an artery (FIG. 17B).

Device 12 was placed in heparinized canine blood (37° C.) for 5 minutes. After the 5 minutes, Device 12 was not wet-out and was photographed (FIG. 17A) after rinsing with saline.

Figure 17B:
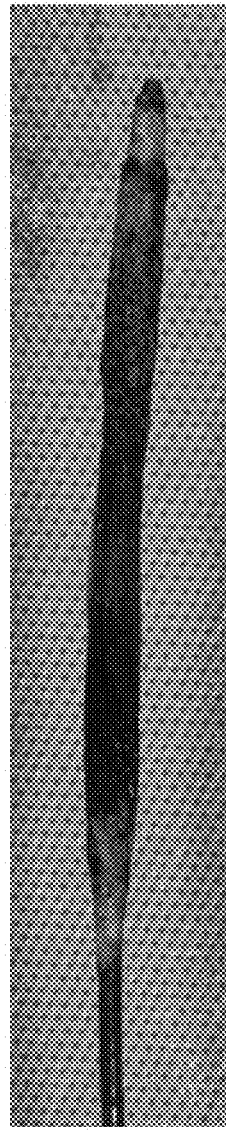

Then, Device 12 was inserted into the artery and inflated to 6 atm for 1 min. Device 12 was deflated, removed from the artery, and photographed (FIG. 17B). After the 1 minute inflation, Device 12 was observed to have wet-out. The artery was rinsed with 25 ml of heparinized canine blood for 5 minutes. Then the artery was incubated in another 25 ml of heparinized canine blood for 5 minutes. Afterward, the artery was then placed in a buffered formalin solution (10% Neutral Buffered Formalin, VWR, Cat#BDH0502-20L, West Chester Pa.) for fixation and storage. This artery herein defined as the Test Artery.

The second vial containing a segment of cryopreserved artery was thawed. This artery was removed from the vial and placed in a buffered formalin solution (10% Neutral Buffered Formalin, VWR, Cat#BDH0502-20L, West Chester Pa.) for fixation and storage. This artery served as a control arterial segment and had no contact with Device 12. This artery herein defined as the Control Artery.

The Test and Control Arteries were each separately cut into approximately 1 cm samples and placed into OCT compound (4583, Tissue-Tek, Sakura Finetek, Torrance, Calif.). The Test and Control Artery samples were frozen in an isopentane/liquid nitrogen solution (2-Methylbutane, M32631-4L, Sigma Aldrich, Saint Louis, Mo.)

While frozen, a cryostat was used to obtain histological sections of Test and Control Artery samples. The resulting histological sections of Test and Control Artery samples were mounted on glass slides and cover-slipped using FluoromountG™ solution (17984-25, Electron Microscopy Sciences, Hatfield, Pa.).

Figure 18A:
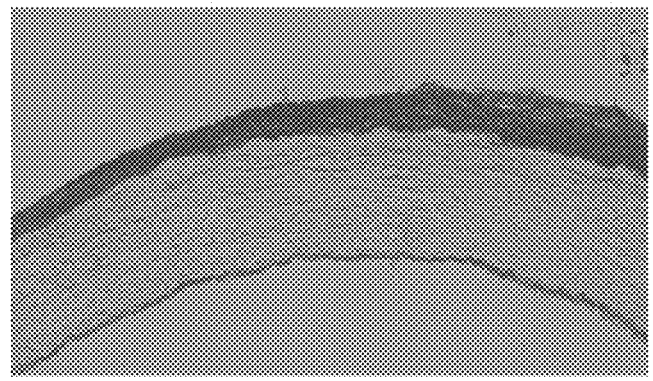
FIGS. 18A through 18D depict histological sections of arteries.
Figure 18B:
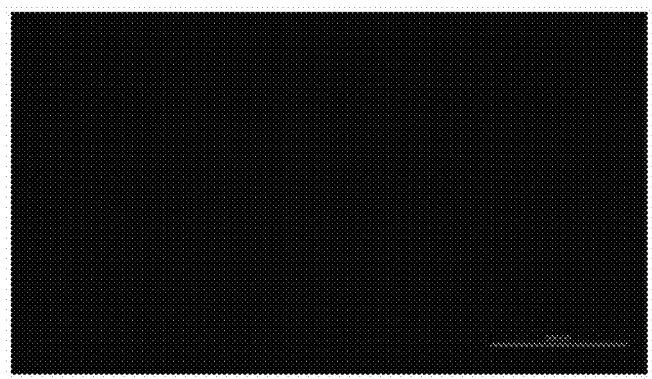
Figure 18C:
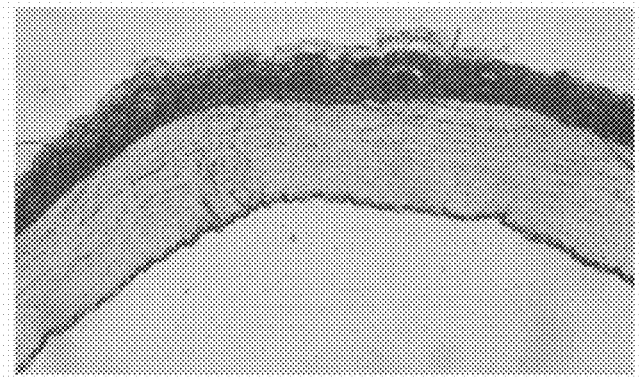
Figure 18D:
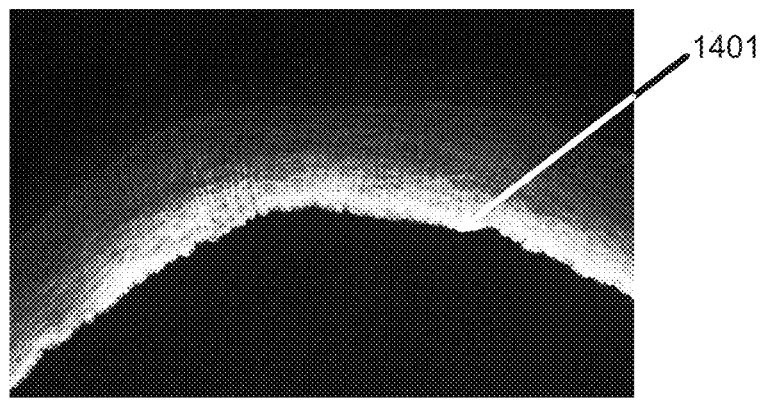

The histological sections of the Control and Test Artery are shown in FIGS. 18A and 18C, respectively. Fluorescence micrographs (596 nm excitation, 615 nm emission) of these images are shown in FIGS. 18B and 18D, respectively. The Test Artery section exhibited fluorescence (FIG. 18D, as depicted by arrow 1401), due to transfer of the Texas-red-labeled-dextran to the artery during Device 12 inflation. The Control Artery section (FIG. 18B) had no contact with Device 12 and exhibited no fluorescence, hence why this Figure is dark.

Example 13

In Vivo Delivery of Texas-Red-Labeled-Dextran to a Canine Artery from a Coated Balloon Catheter A structural cover (as prepared in Example 1) was assembled onto a balloon catheter (as described in Example 2). A hydrophilic coating was then applied to the balloon catheter as described in Example 11. As noted in Example 11, this coating contained a fluorescent molecule (Texas-red-labeled-dextran). An outer sheath layer (previously prepared per Example 4) was then assembled onto the coated balloon catheter (per Example 5). This balloon catheter is herein referred to as Device 13.

Device 13 was inserted into a canine aorta and allowed to dwell for 15 minutes without inflation. After this time, Device 13 was removed from the animal and photographed (FIG. 19A). At this time, Device 13 was not completely wet.

Then Device 13 was inserted into the iliac artery. The balloon was inflated to 12 atm for 1 minute. Device 13 was then deflated, removed from the canine, and photographed (FIG. 19B). At this time, Device 13 was black in color indicating complete wetting.

The animal remained in life for approximately 4 hours. After this time, the animal was euthanized. The ballooned section of iliac artery was harvested and placed in a buffered formalin solution (10% Neutral Buffered Formalin, VWR, Cat#BDH0502-20L, West Chester Pa.). This artery is herein defined as the Test Iliac Artery. An untreated section of iliac artery was harvested and placed in a buffered formalin solution (10% Neutral Buffered Formalin, VWR, Cat#BDH0502-20L, West Chester Pa.). This artery is herein defined as the Control Iliac Artery.

Figure 20A:
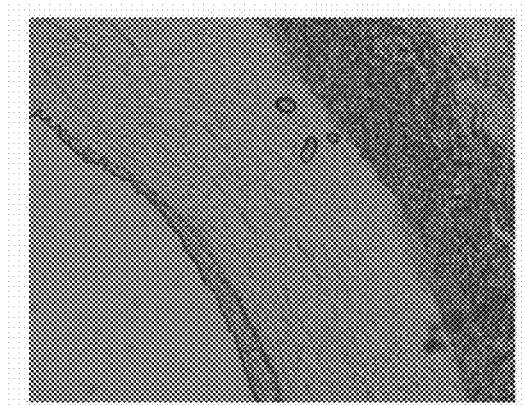
FIGS. 20A through 20D depict histological sections of arteries.
Figure 20B:
Figure 20C:
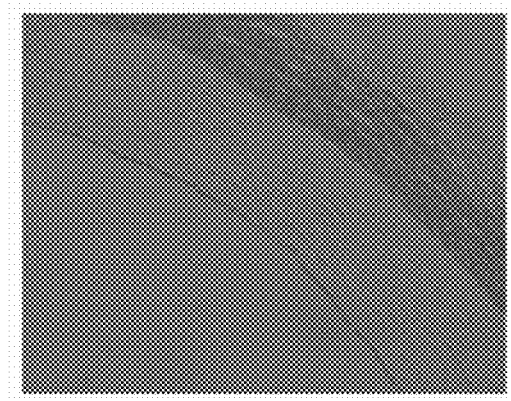
Figure 20D:
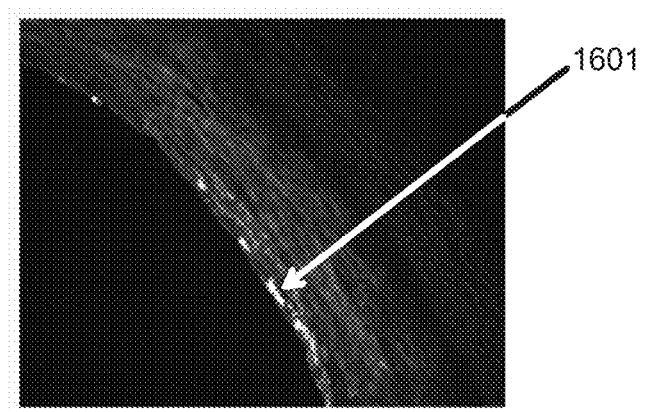

The Test and Control Iliac Arteries were separately sectioned. Light micrographs of the Test and Control Arteries are shown in FIGS. 20C and 20A, respectively. The histological sections were examined and photographed using fluorescence microscopy (596 nm excitation, 615 nm emission). The Test Iliac Artery section (FIG. 20C) exhibited fluorescence (FIG. 20D, as depicted by arrow 1601), due to transfer of the Texas-red-labeled-dextran to the artery during Device 13 inflation. The Control Iliac Artery section (FIG. 20A) had no contact with Device 13 and exhibited no fluorescence (FIG. 20B), hence why this Figure is dark.

Example 14

In-Vitro Evaluation of Pre-Hydration of the PVA Coating Prior to First and Second Inflation Device 14 (as depicted in FIGS. 21A and 21B) was built according to Example 5 and tested in a manner similar to Example 7, except that the Device was not presoaked in blood for 20 minutes in its first state in order to avoid any possibility of pre-hydration of the PVA coating proceeding first inflation. The results of this experiment are detailed in Table 2 and FIGS. 21A and 21B.

The testing began with inflation to 6 atm for 1 minute in blood in a rigid tube. After this time, the degree of wetting was noted, and a picture of Device 14 was taken (FIG. 21A). A subsequent inflation to 12 atm for 1 minute in blood in a rigid tube followed. The degree of wetting was recorded and a picture (FIG. 21B) was taken.

For comparison, Table 2 summarizes the degree of wetting of devices with and without prehydration (Devices 8a and 14, respectively). As noted above, prehydration of Device 8a (Example 8) was facilitated by incubating this device in blood for 20 minutes at its first state prior to device inflation. Device 14 was not incubated in blood at its first state prior to device inflation.

TABLE 2

Degree of Wetting With and Without Prehydration

Figure 22A:
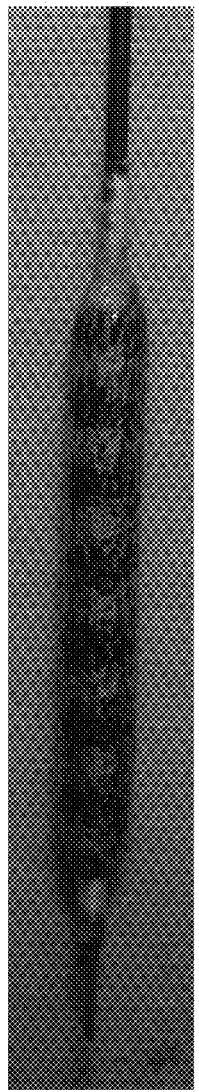
FIG. 22 depicts degree of wetting of Device 8a after prehydration in blood at first state and then expansion in blood in a rigid tube at 6 atm for 1 minute (FIG. 22A), and finally expansion in blood in a rigid tube at 12 atm for 1 minute (FIG. 22B).
Figure 22B:
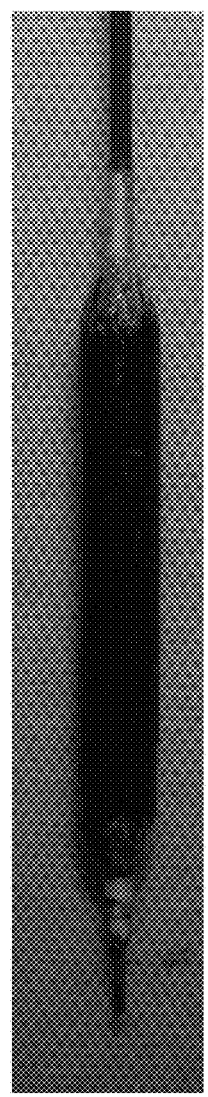

| | Degree of Wetting After: | | |
|---|---|---|---|
| | 20 Min Dwell | 6 atm - 1 min | 12 atm - 1 min |
| Device 14 No Prehydration | N/A | 1 (FIG. 21A) | 5 (FIG. 21B) |
| Device 8a With Prehydration | 1 | 5 (FIG. 22A) | 10 (FIG. 22B) |

This example demonstrates that the outer sheath allows for a degree of coating hydration during the 20 minute dwell at first state and, that although this hydration does not cause excessive wet-out prematurely at first state (Table 2), it does allow for more rapid wetting during the first and second inflations to full diameter.

Example 15

In Vivo Delivery of Texas-Red-Labeled-Dextran to a Femoral Artery from a Coated Balloon Catheter A structural cover (as prepared in Example 1) was assembled onto a balloon catheter (as described in Example 2). A hydrophilic coating was then applied to the balloon catheter as described in Example 11. As noted in Example 11, this coating contained a fluorescent molecule (Texas-red-labeled-dextran). An outer sheath layer (previously prepared per Example 4) was then assembled onto the coated balloon catheter (per Example 5). This balloon catheter is herein referred to as Device 15.

Figure 23:
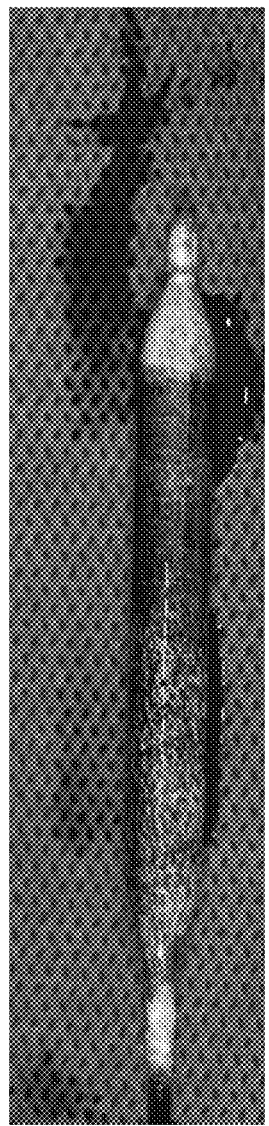
FIG. 23 depicts degree of wetting of Device 15 of Example 15 after expansion in a canine femoral artery in vivo.

Device 15 was inserted into a canine femoral artery and immediately inflated to 6 atm for 1 minute. After this time, Device 15 was removed from the animal, rinsed with saline, re-inflated to 6 atm, and photographed (FIG. 23). At this time, Device 15 was wet-out. As shown in FIG. 24, Texas-red-labeled dextran could be seen on the outer most surface of the device, indicating that the coating became hydrated and was transferred through the outer sheath.

Example 16

In Vitro Wetting of a Balloon Catheter Coated with a Thixotropic Gel

This Example describes the delivery of a thixotropic gel material to a vascular site from a coated balloon.

A first solution (referred herein as Solution 16A) was prepared by mixing phosphate buffered saline (PBS) (0.15M NaCl, pH 7.4, Invitrogen Corporation Carlsbad, Calif.) with 0.40 g/ml hydroxypropyl-β-cyclodextrin (HPβCD) (Sigma-Aldrich, St. Louis, Mo.) and 0.20 g/ml α-cyclodextrin (α-CD) (Sigma-Aldrich) through stirring and heating (60° C.).

A second solution (referred herein as Solution 16B) was prepared by dissolving polyethylene glycol (PEG, Dow Chemical, Midland, Mich.) of average Mn=8 kDa (0.26 g/ml) with PBS.

Equal volumes of Solution 16A and Solution 16 B were combined with mixing to form Gel Material A. Gel Material A was turbid, and was opaque and white in appearance A structural cover was prepared as described in Example 1 and then assembled onto a balloon catheter as described in Example 2. This device (Device 16) was then coated with Gel Material A according to the method described below.

Device 16 was dipped into Gel Material A for about 10 seconds while rotating. After this time, the device was removed from Gel Material A. While rotating the device, a heat gun was used to blow warm air (about 40° C.) over the device for approximately 3 minutes. This process was then repeated two additional times. Next, the device was allowed to air dry overnight.

An outer sheath was prepared as described in Example 4 and then assembled onto Device 16 as described in Example 5. Device 16 underwent testing for in vitro blood wetting according to the method described below.

Blood was harvested from a canine, citrated to prevent clotting, and placed in a 50 ml vial. Device 16 was fully submerged in the blood at first state (unexpanded) for 20 minutes. After 20 minutes, Device 16 was removed from the blood, fully rinsed with saline, and photographed (FIG. 24A).

Device 16 (which has a nominal inflation diameter of 6 mm) was inserted into a 5.9 mm diameter rigid tube (70 mm in length) in blood. Device 16 was then inflated to 6 atm for 1 minute. Afterward, Device 16 was deflated, removed from the blood, rinsed with saline, and photographed (FIG. 24B). After rinsing, Device 16 was re-inserted into the 5.9 mm diameter rigid tube (70 mm in length) in blood and re-inflated to 12 atm for 1 minute. Afterward, Device 16 was deflated, removed from the blood, rinsed with saline, and photographed (FIG. 24C). As shown in FIG. 24C, Device 16 was fully wet at this time.

This example demonstrates that a thixotropic gel coating formulation enables wetting of the device of the agent-eluting invention.

Example 17

Additional Formulations

The coating formulation detailed in Example 16 may be modified to include one or more therapeutic agents. It is expected devices of the agent-eluting invention, coated with these modified formulations will perform as that device described in Example 16 and deliver to target tissues an effective dose of the agent(s).

A first formulation (referred to herein as "Formulation 17A") is prepared by mixing phosphate buffered saline (PBS) (0.15M NaCl, pH 7.4, Invitrogen Corporation Carlsbad, Calif.) with 0.40 g/ml hydroxypropyl-β-cyclodextrin (HPβCD) (Sigma-Aldrich, St. Louis, Mo.) and 0.20 g/ml α-cyclodextrin (α-CD) (Sigma-Aldrich) through stirring and heating (60° C.), followed by adding dexamethasone (Pharmacia & Upjohn Company, Kalamazoo, Mich.) at 20 mg/ml with stirring and heating (60° C.).

A second formulation (referred herein as "Formulation 17B") is prepared by dissolving polyethylene glycol (PEG, Dow Chemical, Midland, Mich.) of average Mn=8 kDa (0.26 g/ml) with PBS.

Equal volumes of Formulation 17A and Formulation 17B are combined via mixing to form a gel, herein referred to as "Material B".

A structural cover is prepared as described in Example 1 and assembled onto a balloon catheter as described in Example 2. This device (hereinafter "Device 17") is then coated with Material B according to the method described in Example 16. Device 17 is tested for in vitro blood wetting according to the method described in Example 16.

This example may be repeated changing only the composition of the "first formulation" (detailed above) as follows.

An alternative first formulation may be prepared by mixing PBS (0.15M NaCl, pH 7.4, Invitrogen) with 0.40 g/ml hydroxypropyl-β-cyclodextrin (HPβCD) (Sigma-Aldrich, St. Louis, Mo.) and 0.20 g/ml α-cyclodextrin (α-CD) (Sigma-Aldrich) through stirring and heating (60° C.), followed by adding 17β-estradiol (20 mg/ml) (Sigma-Aldrich) and then stirring and heating (60° C.).

Another alternative first formulation may be prepared by mixing PBS (0.15M NaCl, pH 7.4) with 0.40 g/ml hydroxypropyl-β-cyclodextrin (HPβCD) (Sigma-Aldrich, St. Louis, Mo.) and 0.20 g/ml α-cyclodextrin (α-CD) (Sigma-Aldrich) through stirring and heating (60° C.), followed by adding dicumarol (0.67 mg/ml) (Sigma-Aldrich) by stirring and heating (60° C.).

An alternative first formulation may be prepared by mixing PBS (0.15M NaCl, pH 7.4) with 0.40 g/ml hydroxypropyl-β-cyclodextrin (HPβCD) (Sigma-Aldrich, St. Louis, Mo.) and 0.20 g/ml α-cyclodextrin (α-CD) (Sigma-Aldrich) through stirring and heating (60° C.), followed by adding rapamycin (0.40 mg/ml) (Sigma-Aldrich) by stirring and heating (60° C.).

Another first formulation may be prepared by mixing PBS (0.15M NaCl, pH 7.4) with 0.40 g/ml hydroxypropyl-β-cyclodextrin (HPβCD) (Sigma-Aldrich, St. Louis, Mo.) and 0.20 g/ml α-cyclodextrin (α-CD) (Sigma-Aldrich) through stirring and heating (60° C.), followed by adding everolimus (0.20 mg/ml) (Sigma-Aldrich) and stirring and heating (60° C.).

Example 18

In Vivo Drug Delivery

This example demonstrates in vivo drug delivery using several different drug eluting balloon catheters of the present invention.

Twelve drug eluting balloon catheters were constructed and deployed in vivo as described below.

Twelve structural covers were prepared as follows. For each structural cover, a film tube was made of an elastomer-imbibed ePTFE film as described in the commonly-assigned, co-pending U.S. Patent Publication 20080125710, entitled INFLATABLE IMBIBED POLYMER DEVICES. Seven layers of the film, 20 cm wide, were longitudinally wrapped on a 1.9 mm stainless steel mandrel with the machine direction of the film parallel to the longitudinal axis of the mandrel. This film tube was overwrapped with approximately 2 layers of a sacrificial ePTFE film to prevent the tube from wrinkling in the subsequent steps. The mandrel was heated in an oven set at 225° C. for 1.75 minutes and the sacrificial ePTFE layers were then removed. Each structural cover construct was removed from the mandrel and cut to a 6.0 cm length.

A dexamethasone coating formulation containing 0.40 g/g deionized water, 0.56 g/g hydroxypropyl-β-cyclodextrin (HPβCD, Sigma-Aldrich, St. Louis, Mo.), and 0.03 g/g dexamethasone (Pharmacia & UpJohn Co, Bridgewater, N.J.), was prepared by placing appropriate quantities of each component in a beaker and stirring overnight at room temperature. This coating formulation is herein referred to as Formulation Dex-ACD.

A paclitaxel coating formulation containing 0.62 g/g deionized water, 0.37 g/g hydroxypropyl-β-cyclodextrin (HPβCD, Sigma-Aldrich, St. Louis, Mo.), and 1.41 mg/g paclitaxel (LC Laboratories, Woburn, Mass.), was prepared by placing appropriate quantities of each component in a beaker and stirring overnight at room temperature. This coating formulation is herein referred to as Formulation Ptx-ACD.

A paclitaxel coating formulation containing 0.73 g/g methanol, 0.22 g/g hydroxypropyl-β-cyclodextrin (HPβCD, Sigma-Aldrich, St. Louis, Mo.), and 58.58 mg/g paclitaxel (LC Laboratories, Woburn, Mass.), was prepared by placing appropriate quantities of each component in a beaker and stirring overnight at room temperature. This coating formulation is herein referred to as Formulation Ptx-MCD+.

A paclitaxel coating formulation containing 0.75 g/g methanol, 0.19 g/g sodium salicylate (Sigma-Aldrich, St. Louis, Mo.), and 59.29 mg/g paclitaxel (LC Laboratories, Woburn, Mass.), was prepared by placing appropriate quantities of each component in a beaker and stirring overnight at room temperature. This coating formulation is herein referred to as Formulation Ptx-MNS.

Each structural cover (prepared as described above) was separately slipped over a mandrel which was subsequently rotated. While the covers were rotating, 100 µl of one of the formulation Dex-ACD, Ptx-ACD, Ptx-MCD+, or Ptx-MNS was applied to a 40 mm length mid section of the structural cover according to the schedule shown in Table 3. Each coated cover was then dried in an oven at approximately 75° C. for 20 minutes.

An ePTFE film was obtained having the following characteristics. Width (parallel to the machine direction): 10 cm. Matrix tensile strength, machine direction: 101,087 psi. Density: 0.415 g/cc. The typical estimated mean fibril length for this film material is 32 µm, arrived at by examination of a scanning electron photomicrograph of the material.

This ePTFE film was used to prepare twelve outer sheaths as follows. For each sheath, a film tube was created by longitudinally-wrapping two layers of the film characterized above onto a 2.5 mm diameter mandrel with the machine direction of the film parallel to the longitudinal axis of the mandrel. This film was overwrapped with approximately 1 layer of a sacrificial ePTFE. The film-covered mandrel was heated in an oven set at 380° C. for 6 minutes and then the sacrificial ePTFE layer was removed. This sheath construct was removed from the mandrel and cut to a 6.0 cm length.

Each of the twelve outer sheaths was modified with a hydrophilic coating using the method essentially as described in co-assigned U.S. Pat. No. 7,020,529, entitled "Defibrillation Electrode Cover". Sheaths were fully submerged in a bath of 100% isopropyl alcohol for 30 seconds, then transferred to a bath containing 2% polyvinyl alcohol (g/mL) in deionized water and allowed to dwell for 20 minutes. Sheaths were then rinsed in deionized water for 15 minutes. Upon rinse completion, the sheaths were transferred to a bath containing 2% glutaraldehyde (mL/mL) and 1.0% hydrochloric acid (mL/mL) in deionized water. The sheaths remained in this bath for 15 minutes and were then transferred to a deionized water rinse for an additional 15 minutes. All sheaths were allowed to dry in ambient air for approximately 2 hours Twelve balloon catheters (Bavaria Medizin Technologie, Oberpfaffenhofen, Germany, model #BMT-035, with balloon dimensions of 6.0 mm×40 mm) were obtained. One coated structural cover (see Table 3, below) was centered over each balloon aligning the distal and proximal ends of the drug coating with the balloon marker bands. Loctite 7701 Primer (Henkel AG & Co. KgaA, Düsseldorf, Germany) was applied to the end of the coated structural layer and surrounding catheter. The ends of the coated structural layer were then fixedly attached to the balloon catheter using approximately five layers of an approximately 6.4 mm width of ePTFE reinforcing film. The reinforcing film layers were wrapped circumferentially around the cover ends while Loctite 4981 was applied to the film.

One outer sheath was then placed over the coated structural cover (now attached to a balloon catheter) with their ends aligned. Loctite 7701 Primer (Henkel AG & Co. KgaA, Düsseldorf, Germany) was applied to the end of the outer sheath and surrounding catheter. The ends of the outer sheath were then fixedly attached to the balloon catheter using approximately five layers of an approximately 6.4 mm width of ePTFE reinforcing film. The reinforcing film layers were wrapped circumferentially around the outer sheath ends while Loctite 4981 was applied to the film.

Each balloon catheter was deployed in a porcine femoral artery as described below.

Prior to surgery, angiography of each treatment site was used to obtain vessel diameter and length measurements and to determine the appropriate balloon inflation pressure required for approximately 20-30% oversizing. Each balloon catheter was tracked to the treatment site and inflated for 60 seconds, and subsequently, deflated and removed from the animal. The animal remained in life under anesthesia for at least 1 hour with blood flow through the treatment site.

After this time period, each animal was euthanized. Then, the treated arterial vessel segment was exposed, attached to a longitudinal retention device, and excised. An untreated, remote artery (the carotid artery) was also harvested to assess potential systemic drug delivery to a remote site.

Adipose tissue was removed from the adventitia of each harvested arterial segment. Then, radial cross-sections (100±50 mg) were carefully cut from each treated and control artery. The mass of each section and its location along the treatment length were noted. Vessel sections distal and proximal to the treatment areas were also harvested.

Arteries treated with devices containing paclitaxel (see Table 3) were analyzed for paclitaxel concentration by LC/MS-MS. Arteries treated with devices containing dexamethasone were analyzed for dexamethasone concentration by LC/MS-MS. For each treated artery, mean drug concentrations in the proximal, treated, distal, and remote segments were calculated as the average drug concentration of all sections in the indicated segment (Table 3). Treatment means (FIG. 25) were then calculated by averaging the segment means with n=3 arteries for each treatment group.

TABLE 3

Summary of Drug Concentrations (ng drug per g tissue) in Arterial Segments Proximal to, Within the Treatment Site, Distal to, or Remote from Tissue Treated by Balloon Catheter Deployment

| Structural Cover/ Device ID | Coating Formulation on Balloon Catheters | Artery | Prox-imal | Treat-ment | Distal | Re-mote |
|---|---|---|---|---|---|---|
| Avg Dexamethasone Per Segment (ng drug/g tissue) | | | | | | |
| 1498-166-19 | Formulation | 1 | 69 | 280 | 131 | 0 |
| 1498-166-25 | Dex- | 2 | 81 | 1408 | 168 | 23 |
| 1498-166-26 | ACD | 3 | 322 | 711 | 94 | 49 |
| Avg Paclitaxel Per Segment (ng drug/g tissue) | | | | | | |
| DEB356 | Formulation | 4 | 48 | 355 | 0 | 0 |
| DEB358 | Ptx- | 5 | 37 | 327 | 49 | 0 |
| DEB353 | ACD | 6 | 13 | 456 | 15 | 0 |
| DEB502 | Formulation | 7 | 178 | 4905 | 273 | 0 |
| DEB506 | Ptx- | 8 | 325 | 5800 | 107 | 0 |
| DEB504 | MCD | 9 | 451 | 8080 | 227 | 0 |
| DEB496 | Formulation | 10 | 2256 | 48750 | 3121 | 0 |
| DEB494 | Ptx- | 11 | 286 | 3680 | 211 | 0 |
| DEB495 | MNS | 12 | 1446 | 31750 | 1968 | 0 |

Figure 25:
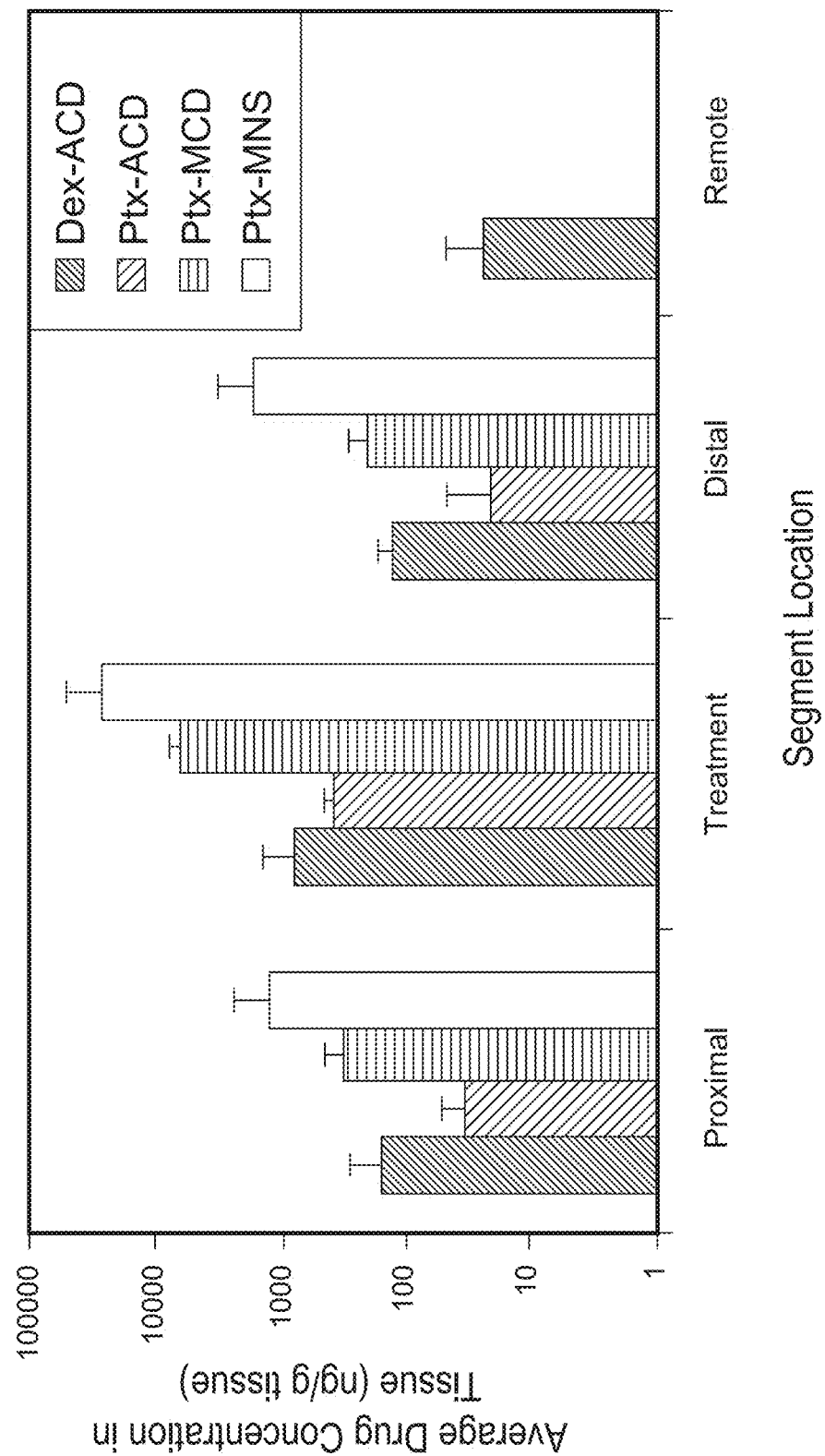
FIG. 25 depicts treatment averages of drug concentration (nanogram (ng) drug per gram (g) tissue, n=3 arteries per treatment) in tissue segments proximal to, within the treatment site, distal to, or remote from tissue treated by constructs of the invention as described in Example 18.

As shown in Table 3 and FIG. 25, deployment of each balloon catheter successfully delivered drug to the treatment site with minimal drug delivery to adjacent (proximal or distal) or remote vascular tissue sites.

Example 19

Alternative Formulations

This example depicts in vivo drug delivery using drug eluting balloon catheters of the present invention which use therapeutic agent formulations different from those in Example 18.

Drug eluting balloon catheters are constructed and deployed in vivo as described in Example 18, above. However the following drug formulations may be substituted for those described in Example 18.

A 17β-estradiol coating formulation containing 0.62 g/g DI water, 0.37 g/g hydroxypropyl-β-cyclodextrin (HPβCD, Sigma-Aldrich, St. Louis, Mo.), and 1.41 mg/g 17β-estradiol (Sigma-Aldrich, St. Louis, Mo.) is prepared by placing appropriate quantities of each component in a beaker and stirring overnight at room temperature.

A 17β-estradiol coating formulation containing 0.73 g/g methanol, 0.22 g/g hydroxypropyl-β-cyclodextrin (HPβCD, Sigma-Aldrich, St. Louis, Mo.), and 50.0 mg/g 17β-estradiol (Sigma-Aldrich, St. Louis, Mo.) is prepared by placing appropriate quantities of each component in a beaker and stirring overnight at room temperature.

A 17β-estradiol coating formulation containing 0.75 g/g methanol, 0.19 g/g sodium salicylate (Sigma-Aldrich, St. Louis, Mo.), and 50.0 mg/g 17β-estradiol (Sigma-Aldrich, St. Louis, Mo.) is prepared by placing appropriate quantities of each component in a beaker and stirring overnight at room temperature.

A dicumarol coating formulation containing 0.62 g/g DI water, 0.37 g/g hydroxypropyl-β-cyclodextrin (HPβCD, Sigma-Aldrich, St. Louis, Mo.), and 0.40 mg/g dicumarol (Sigma-Aldrich, St. Louis, Mo.) is prepared by placing appropriate quantities of each component in a beaker and stirring overnight at room temperature.

A dicumarol coating formulation containing 0.73 g/g methanol, 0.22 g/g hydroxypropyl-β-cyclodextrin (HPβCD, Sigma-Aldrich, St. Louis, Mo.), and 0.40 mg/g dicumarol (Sigma-Aldrich, St. Louis, Mo.) is prepared by placing appropriate quantities of each component in a beaker and stirring overnight at room temperature.

A dicumarol coating formulation containing 0.75 g/g methanol, 0.19 g/g sodium salicylate (Sigma-Aldrich, St. Louis, Mo.), and 0.40 mg/g dicumarol (Sigma-Aldrich, St. Louis, Mo.) is prepared by placing appropriate quantities of each component in a beaker and stirring overnight at room temperature.

A rapamycin coating formulation containing 0.62 g/g DI water, 0.37 g/g hydroxypropyl-β-cyclodextrin (HPβCD, Sigma-Aldrich, St. Louis, Mo.), and 0.40 mg/g rapamycin (Sigma-Aldrich, St. Louis, Mo.) is prepared by placing appropriate quantities of each component in a beaker and stirring overnight at room temperature.

A rapamycin coating formulation containing 0.73 g/g methanol, 0.22 g/g hydroxypropyl-β-cyclodextrin (HPβCD, Sigma-Aldrich, St. Louis, Mo.), and 0.40 mg/g rapamycin (Sigma-Aldrich, St. Louis, Mo.) is prepared by placing appropriate quantities of each component in a beaker and stirring overnight at room temperature.

A rapamycin coating formulation containing 0.75 g/g methanol, 0.19 g/g sodium salicylate (Sigma-Aldrich, St. Louis, Mo.), and 0.40 mg/g rapamycin (Sigma-Aldrich, St. Louis, Mo.) is prepared by placing appropriate quantities of each component in a beaker and stirring overnight at room temperature.

A everolimus coating formulation containing 0.62 g/g DI water, 0.37 g/g hydroxypropyl-β-cyclodextrin (HPβCD, Sigma-Aldrich, St. Louis, Mo.), and 0.20 mg/g everolimus (Sigma-Aldrich, St. Louis, Mo.) is prepared by placing appropriate quantities of each component in a beaker and stirring overnight at room temperature.

A everolimus coating formulation containing 0.73 g/g methanol, 0.22 g/g hydroxypropyl-β-cyclodextrin (HPβCD, Sigma-Aldrich, St. Louis, Mo.), and 0.20 mg/g everolimus (Sigma-Aldrich, St. Louis, Mo.) is prepared by placing appropriate quantities of each component in a beaker and stirring overnight at room temperature.

A everolimus coating formulation containing 0.75 g/g methanol, 0.19 g/g sodium salicylate (Sigma-Aldrich, St. Louis, Mo.), and 0.20 mg/g everolimus (Sigma-Aldrich, St. Louis, Mo.) is prepared by placing appropriate quantities of each component in a beaker and stirring overnight at room temperature.

Example 20

Microstructural Changes

The following example shows the microstructural changes which occur upon expansion of drug eluting balloons of the present invention.

A drug eluting balloon was prepared as described in Example 18 but the structural cover was not coated with a formulation containing a therapeutic agent. FIG. 3C is a scanning electromicrograph (at magnification of 500×) of the film comprising the outer sheath mounted on this balloon as assembled and prior to inflation. It will be noted the microstructure is in a first state with a closed microstructure. The balloon was subsequently expanded to its nominal diameter (6.0 mm) and the scanning electromicrograph of the film comprising the outer sheath at said expanded state is shown in FIG. 3D. As is apparent, a second state results from expansion, i.e., a film with a more open microstructure.

Example 21

In Vivo Drug Delivery from Various Paclitaxel Coating Formulations

Fourteen drug eluting balloon catheters were constructed and deployed in vivo as described below.

Eight structural covers were prepared as follows (see Table 5 for structural cover IDs). For each structural cover, a film tube was made of an elastomer-imbibed ePTFE film as described in the commonly-assigned, co-pending U.S. Patent Publication 20080125710, entitled INFLATABLE IMBIBED POLYMER DEVICES. Seven layers of the film, 20 cm wide, were longitudinally wrapped on a 1.9 mm stainless steel mandrel with the machine direction of the film parallel to the longitudinal axis of the mandrel. This film tube was overwrapped with approximately 2 layers of a sacrificial ePTFE film to prevent the tube from wrinkling in the subsequent steps. The mandrel was baked in an oven set at 225° C. for 1.75 minutes and the sacrificial ePTFE layers were then removed. Each structural cover construct was removed from the mandrel and cut to a 6.0 cm length.

Six structural covers were prepared as follows (see Table 5 for structural cover IDs). For each structural cover, a film tube was made of an elastomer-imbibed ePTFE film as described in the commonly-assigned, co-pending U.S. Patent Publication 200801257, entitled INFLATABLE IMBIBED POLYMER DEVICES. Five layers of the film, 20 cm wide, were longitudinally wrapped on a 1.7 mm stainless steel mandrel with the machine direction of the film parallel to the longitudinal axis of the mandrel. This film tube was overwrapped with approximately 2 layers of a sacrificial ePTFE film to prevent the tube from wrinkling in the subsequent steps. The mandrel was baked in an oven set at 225° C. for 1.75 minutes and the sacrificial ePTFE layers were then removed. Each structural cover construct was removed from the mandrel and cut to a 6.0 cm length.

The following paclitaxel coating formulations were prepared and are summarized in Table 4.

A paclitaxel coating formulation containing 0.72 g/g methanol, 0.21 g/g hydroxypropyl-β-cyclodextrin (HPβCD, Sigma-Aldrich, St. Louis, Mo.), 0.01 g/g dimethyl sulfoxide (DMSO, Sigma-Aldrich, St. Louis, Mo.), and 58.6 mg/g paclitaxel (LC Laboratories, Woburn, Mass.) was prepared by placing appropriate quantities of each component in a beaker and stirring until dissolved. This coating formulation is herein defined as Formulation Ptx-MCD+.

A paclitaxel coating formulation containing 0.70 g/g methanol, 0.19 g/g sodium salicylate (NS, Sigma-Aldrich, St. Louis, Mo.), 0.36 g/g DMSO, and 69.4 mg/g paclitaxel was prepared by placing appropriate quantities of each component in a beaker and stirring until dissolved. This coating formulation is herein defined as Formulation Ptx-MNS4+.

A paclitaxel coating formulation containing 0.74 g/g ethanol (EMD, Rockland, Ma), 0.07 g/g water, 20.0 mg/g paclitaxel, 0.07 g/g HPβCD, 3.2 mg/g DMSO, and 0.10 g/g poloxamer-188 (Lutrol F68, Mutchler Inc, Harrington Park, N.J.) was prepared by placing appropriate quantities of each component in a beaker and stirring until dissolved. This coating formulation is herein defined as Formulation Ptx-Pol/CD/DMSO-30.

A paclitaxel coating formulation containing 0.72 g/g ethanol (EMD, Rockland, Ma), 0.04 g/g water, 30.5 mg/g paclitaxel, 0.05 g/g HPβCD, 18.9 mg/g DMSO, and 0.14 g/g poloxamer-188 was prepared by placing appropriate quantities of each component in a beaker and stirring until dissolved. This coating formulation is herein defined as Formulation Ptx-Pol/CD/DMSO-40.

A paclitaxel coating formulation containing 0.76 g/g methanol, 39.6 mg/g paclitaxel, 0.20 g/g HYAMINE®-1622 (Product#53751, Sigma-Aldrich, St. Louis, Mo.) was prepared by placing appropriate quantities of each component in a beaker and stirring until dissolved. This coating formulation is herein defined as Formulation Ptx-HYA.

A paclitaxel coating formulation containing 0.87 g/g methanol, 43.5 mg/g paclitaxel, 0.08 g/g poloxamer-188, and 0.02 g/g polyethylene glycol (PEG, $M_w$=3350 Da, Product#166978, The Dow Chemical Company, Pittsburg, Calif.) was prepared by placing appropriate quantities of each component in a beaker and stirring until dissolved. This coating formulation is herein defined as Formulation Ptx-PoPEG.

Upon completion of stirring, all coating formulations were clear solutions without any visible precipitation.

TABLE 4

Paclitaxel Coating Formulations Examined in Example 21

| Formulation | Paclitaxel Coating Formulations (g component per g total) | | | | | | | | | |
|---|---|---|---|---|---|---|---|---|---|---|
| | Methanol | Ethanol | Water | Paclitaxel | HPβCD | NS | DMSO | Poloxamer | Hyamine | PEG |
| Ptx-MCD+ | 0.7214 | — | — | 0.0586 | 0.2100 | — | 0.0100 | — | — | — |
| Ptx-MNS4+ | 0.7030 | — | — | 0.0694 | — | 0.1918 | 0.0359 | — | — | — |
| Ptx-Pol/CD/DMSO-30 | — | 0.7428 | 0.0687 | 0.0200 | 0.0659 | — | 0.0032 | 0.0995 | — | — |
| Ptx-Pol/CD/DMSO-40 | — | 0.7173 | 0.0442 | 0.0305 | 0.0490 | — | 0.0189 | 0.1400 | — | — |
| Ptx-HYA | 0.7610 | — | — | 0.0396 | — | — | — | — | 0.1994 | — |
| Ptx-PoPEG | 0.8716 | — | — | 0.0435 | — | — | — | 0.0849 | — | 0.0241 |

Each structural cover (prepared as described above) was separately slipped over a mandrel which was subsequently rotated. While the covers were rotating, 100 μl of one of the paclitaxel formulations described above (and in Table 4) was applied to a 40 mm length mid-section of the structural cover according to the schedule shown in Table 5. Each coated cover was then dried in an oven at approximately 75° C. for 20 minutes.

An ePTFE film tape was obtained having the following characteristics. Width (parallel to the machine direction): 10 cm. Matrix tensile strength, machine direction: 92,000 psi. Matrix tensile strength, transverse direction: 570 psi. Density: 0.52 g/cc. Mean fibril length: 30 µm, arrived at by examination of a scanning electron photomicrograph of the material.

This ePTFE film tape was used to prepare fourteen outer sheaths as follows. For each sheath, a film tube was created by longitudinally wrapping two layers of the film tape characterized above onto a 2.5 mm diameter mandrel with the machine direction of the film parallel to the longitudinal axis of the mandrel. This film was overwrapped with approximately 1 layer of a sacrificial ePTFE. The film-covered mandrel was baked in an oven set at 380° C. for 6 minutes and then the sacrificial ePTFE layer was removed. This sheath construct was removed from the mandrel and cut to a 6.0 cm length.

Each of the fourteen outer sheaths was modified with a hydrophilic coating using the following method. Sheaths were fully submerged in a bath of 100% isopropyl alcohol for 30 seconds, then transferred to a bath containing 2% polyvinyl alcohol (g/mL) in deionized (DI) water and allowed to dwell for 20 minutes. Sheaths were then rinsed in DI water for 15 minutes. Upon rinse completion, the sheaths were transferred to a bath containing 2% glutaraldehyde (mL/mL) and 1% hydrochloric acid (mL/mL) in DI water. The sheaths remained in this bath for 15 minutes and were then transferred to a DI water rinse for an additional 15 minutes. All sheaths were allowed to dry in ambient air for approximately 2 hours.

Fourteen balloon catheters were obtained from either Bavaria Medizin Technologie (BMT, Oberpfaffenhofen, Germany, model #BMT-035, with balloon dimensions of 6.0 mm×40 mm or 5.0 mm×40 mm) or Creagh Medical, LTD (Galway, Ireland, model #PN00084-540L, with balloon dimensions of 5.0 mm×40 mm) (see Table 5).

One coated structural cover (from Table 5) was centered over each balloon aligning the distal and proximal ends of the drug coating with the balloon marker bands. Loctite 7701 Primer (Henkel AG & Co. KgaA, Düsseldorf, Germany) was applied to the end of the coated structural layer and surrounding catheter. The ends of the coated structural layer were then fixedly attached to the balloon catheter using approximately five layers of an approximately 6.4 mm width of ePTFE reinforcing film. The reinforcing film layers were wrapped circumferentially around the cover ends while Loctite 4981 was applied to the film.

One outer sheath was then placed over the coated structural cover (now attached to a balloon catheter) with their ends aligned. Loctite 7701 Primer (Henkel AG & Co. KgaA, Düsseldorf, Germany) was applied to the end of the outer sheath and surrounding catheter. The ends of the outer sheath were then fixedly attached to the balloon catheter using approximately five layers of an approximately 6.4 mm width of ePTFE reinforcing film. The reinforcing film layers were wrapped circumferentially around the outer sheath ends while Loctite 4981 was applied to the film.

Each balloon catheter was deployed in a porcine femoral artery as described below.

Prior to surgery, angiography of each treatment site was used to obtain vessel diameter and length measurements and to determine the appropriate balloon inflation pressure required for approximately 20-30% oversizing. Each balloon catheter was tracked to the treatment site and inflated for 60 seconds, and subsequently, deflated and removed from the animal. The animal remained in life for either 1 hour or 24 hour with blood flow through the treatment site.

After this time period, each animal was euthanized. Then, the treated arterial vessel segment was exposed, attached to a longitudinal retention device, and excised. An untreated, remote artery (the carotid artery) was also harvested to assess potential systemic drug delivery to a remote site.

Adipose tissue was removed from the adventitia of each harvested arterial segment. Then, radial cross-sections (100±50 mg) were carefully cut from each treated and control artery. The mass of each section and its location along the treatment length were noted. Vessel sections distal and proximal to the treatment areas were also harvested.

The vessel sections were analyzed for paclitaxel concentration by LC/MS-MS. For each treated artery, mean drug concentrations in the proximal, treated, distal, and remote segments were calculated as the average drug concentration of all sections in the indicated segment (Table 5). Treatment means were then calculated by averaging the segment means with n=2 arteries for each 24 h treatment group (FIG. 26) and n=3 arteries for each 1 h treatment group (FIG. 27).

Figure 26:
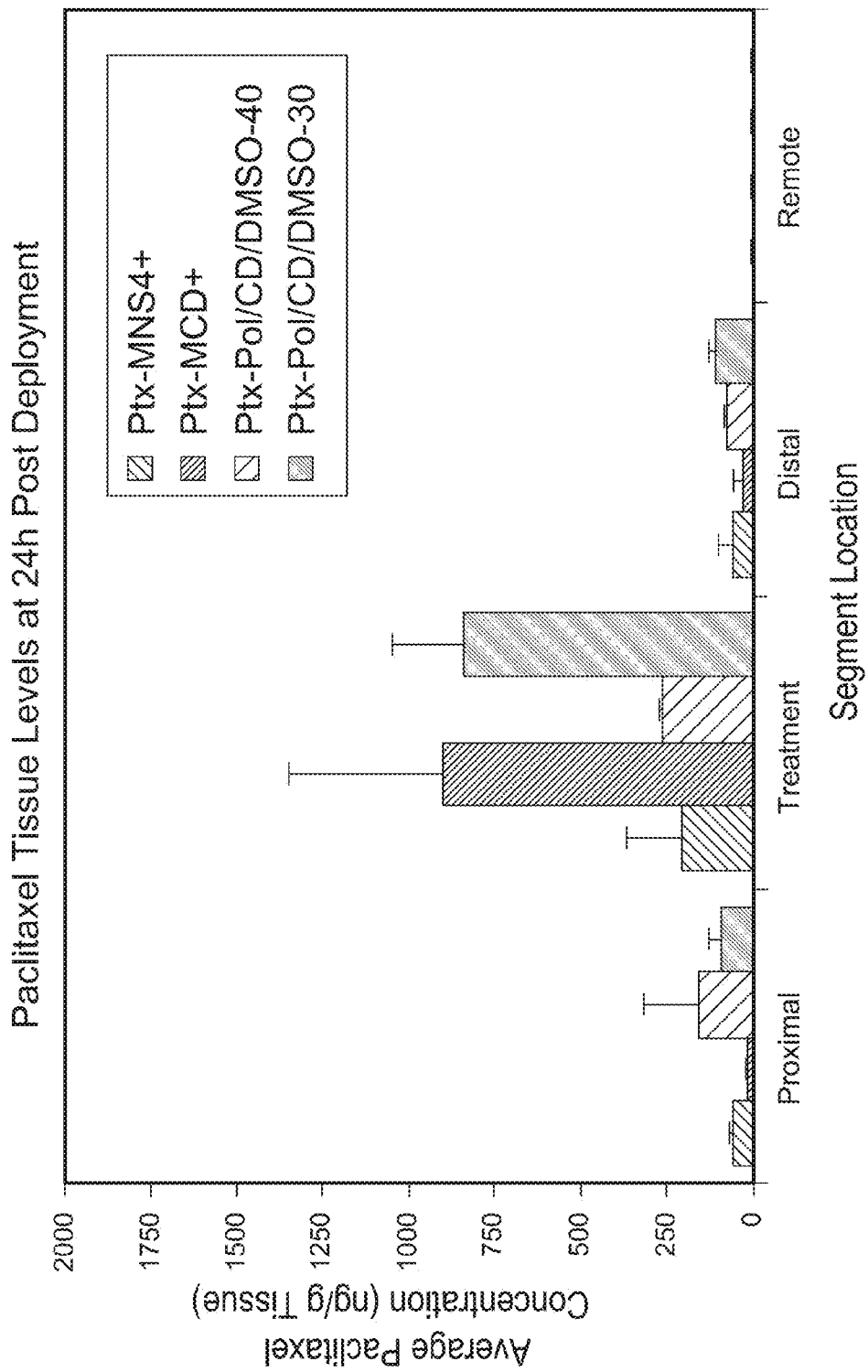
FIG. 26 depicts 24 hours treatment averages of paclitaxel concentration (ng drug per g tissue, n=2 arteries per treatment) in tissue segments proximal to, within the treatment site, distal to, or remote from tissue treated by constructs of the invention as described in Example 21.
Figure 27:
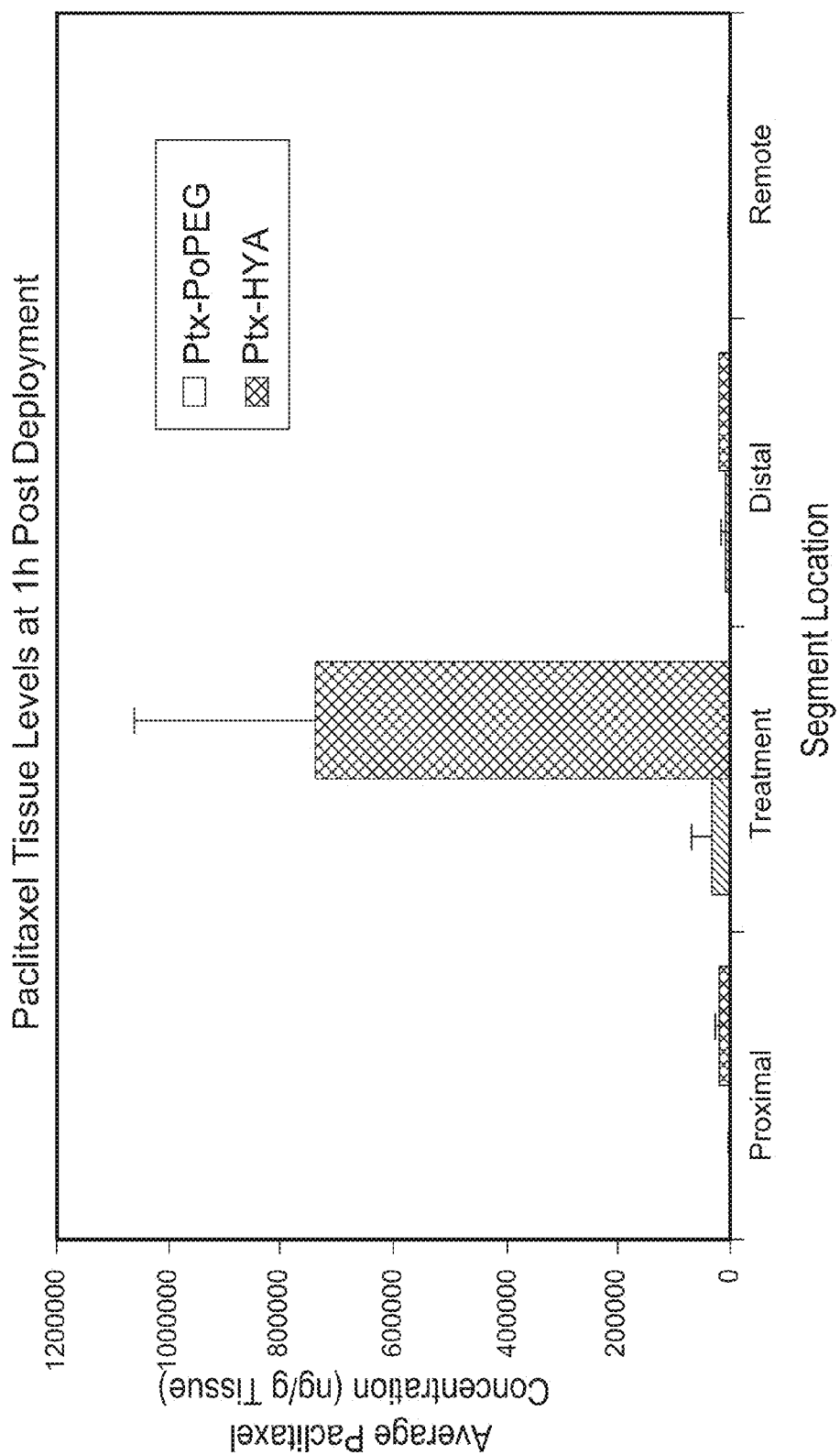
FIG. 27 depicts 1 hour treatment averages of paclitaxel concentration (ng drug per g tissue, n=3 arteries per treatment) in tissue segments proximal to, within the treatment site, distal to, or remote from tissue treated by constructs of the invention as described in Example 21.

As shown in Table 5 and FIGS. 26 and 27, deployment of each balloon catheter successfully delivered paclitaxel to the treatment site with minimal drug delivery to adjacent or remote vascular tissue sites.

TABLE 5

Summary of Paclitaxel Concentrations (ng drug per g tissue) in Arterial Segments Proximal to, Within the Treatment Site, Distal to, or Remote from Tissue Treated by Balloon Catheter Deployment at 1 h or 24 h Post-Deployment

| Structural Cover/Device ID | | | Balloon | | | Average Paclitaxel Per Segment (ng drug/g tissue) | | | |
|---|---|---|---|---|---|---|---|---|---|
| ID | # film layers, inner diameter | Coating Formulation | Manufacturer, Diameter | Time (Post Deployment) | Artery | Proximal | Treatment | Distal | Remote |
| DEB586 | 7 layers, | Ptx-MNS4+ | BMT, 5 mm | 24 h | 1203-L | 41 | 97 | 83 | 0 |
| DEB588 | 1.9 mm diameter | | | | 1204-R | 61 | 320 | 18 | 0 |
| DEB532 | (uninflated) | Ptx-MCD+ | BMT, 6 mm | | 1201-R | 9 | 581 | 18 | 0 |
| DEB531 | | | | | 1201-L | 14 | 1218 | 44 | 0 |
| DEB597 | | Ptx-Pol/CD/ | BMT, 5 mm | | 1203-R | 269 | 264 | 81 | 0 |
| DEB601 | | DMSO-40 | | | 1204-L | 33 | 254 | 63 | 0 |
| DEB529 | | Ptx-Pol/CD/ | | | 1219-R | 111 | 695 | 120 | 0 |
| DEB530 | | DMSO-30 | | | 1219-L | 65 | 988 | 92 | 0 |
| DEB746 | 5 layers, | Ptx-PoPEG | Creagh, 5 mm | 1 h | 1239-R | 482 | 75790 | 15746 | 0 |

TABLE 5-continued

Summary of Paclitaxel Concentrations (ng drug per g tissue) in
Arterial Segments Proximal to, Within the Treatment Site, Distal to, or Remote
from Tissue Treated by Balloon Catheter Deployment at 1 h or 24 h Post-Deployment

| Structural Cover/Device ID | | | Balloon | | | Average Paclitaxel Per Segment | | | |
|---|---|---|---|---|---|---|---|---|---|
| | # film layers, inner | Coating | Manufacturer, | Time (Post | | (ng drug/g tissue) | | | |
| ID | diameter | Formulation | Diameter | Deployment) | Artery | Proximal | Treatment | Distal | Remote |
| DEB747 | 1.7 mm diameter | | | | 1246-L | 2424 | 5120 | 567 | 0 |
| DEB745 | (uninflated) | | | | 1241-R | 340 | 11500 | 705 | 0 |
| DEB736 | | Ptx-HYA | | | 1239-L | 12726 | 949000 | 14367 | 0 |
| DEB738 | | | | | 1246-R | 24830 | 891500 | 16300 | 0 |
| DEB737 | | | | | 1241-L | 5538 | 351500 | 12800 | 0 |

Example 22

Paclitaxel Coating Formulations

The following paclitaxel coating formulations were prepared (and are summarized in Table 6) as described below.

A paclitaxel coating formulation containing 0.87 g/g methanol, 44.4 mg/g paclitaxel, 0.09 g/g poloxamer-188 was prepared by placing appropriate quantities of each component in a beaker and stirring until dissolved. This coating formulation is herein defined as Formulation Ptx-POLO.

A paclitaxel coating formulation containing 0.86 g/g methanol, 41.7 mg/g paclitaxel, and 0.10 g/g Vitamin B3 (Niacinamide, USP Grade, Spectrum Chemicals & Laboratory Products, New Brunswick, N.J.) was prepared by placing appropriate quantities of each component in a beaker and stirring until dissolved. This coating formulation is herein defined as Formulation Ptx-VB.

A paclitaxel coating formulation containing 0.82 g/g methanol, 39.5 mg/g paclitaxel, 0.04 g/g Vitamin E (α-Tocopherol, Product#T3251, Sigma-Aldrich, St. Louis, Mo.), and 0.10 g/g Vitamin B3, was prepared by placing appropriate quantities of each component in a beaker and stirring until dissolved. This coating formulation is herein defined as Formulation Ptx-VBE.

Upon completion of stirring, all coating formulations were clear solutions without any visible precipitation.

TABLE 6

Paclitaxel Coating Formulations Examined in Example 22

| | Paclitaxel Coating Formulations (g component per g total) | | | | |
|---|---|---|---|---|---|
| Formulation | Methanol | Paclitaxel | Vitamin E | Vitamin B3 | Poloxamer |
| Ptx-POLO | 0.8676 | 0.0444 | — | — | 0.0880 |
| Ptx-VBE | 0.8204 | 0.0395 | 0.0399 | 0.1002 | — |
| Ptx-VB | 0.8550 | 0.0417 | — | 0.1033 | — |

Structural covers were prepared per the methods described in Example 21 and as detailed in Table 7. Each structural cover was separately slipped over a mandrel which was subsequently rotated. While the covers were rotating, 100 μl of one of the paclitaxel formulation described in Table 6 was applied to a 40 mm length mid-section of the structural cover. Each coated cover was then dried in an oven set at 75° C. for 20 minutes.

Following the methods of Example 21, each coated structural cover was used in the construction of a drug elution balloon. In brief, outer sheaths were prepared as described in Example 21. Each outer sheath was modified with a hydrophilic coating using the methods described in Example 21.

Balloon catheters were obtained from either Bavaria Medizin Technologie (BMT, Oberpfaffenhofen, Germany, model #BMT-035, with balloon dimensions of 6.0 mm×40 mm or 5.0 mm×40 mm) or Creagh Medical, LTD (Galway, Ireland, model #PN00084-540L, with balloon dimensions of 5.0 mm×40 mm).

One coated structural cover was then attached to one balloon catheter using the methods described in Example 21. One outer sheath was then placed over the coated structural cover (now attached to a balloon catheter) with their ends aligned. The outer sheath was attached to the balloon catheter per the methods of Example 21.

TABLE 7

Drug-Eluting Balloons Built Using Formulations Examined in Example 22

| Structural Cover/Device ID | | | Balloon |
|---|---|---|---|
| ID | # film layers, inner diameter | Coating Formulation | Manufacturer, Diameter |
| DEB629 | 7 layers, | Ptx-VB | BMT, 5 mm |
| DEB630 | 1.9 mm diameter | Ptx-VBE | BMT, 5 mm |
| DEB631 | (uninflated) | | |
| DEB642 | | | |
| DEB643 | | | |
| DEB641 | | | |
| DEB727 | 5 layers, | Ptx-POLO | Creagh, 5 mm |
| DEB728 | 1.7 mm diameter | | |
| DEB729 | (uninflated) | | |

Example 23

Alternative Formulations

The following drug formulations may be substituted for those described in Example 21.

A rapamycin coating formulation containing 0.76 g/g methanol, 39.6 mg/g rapamycin (Sigma-Aldrich, St. Louis, Mo.), 0.20 g/g HYAMINE®-1622 (Product#53751, Sigma-Aldrich, St. Louis, Mo.) is prepared by placing appropriate quantities of each component in an airtight beaker and stirring overnight.

A rapamycin coating formulation containing 0.87 g/g methanol, 43.5 mg/g rapamycin (Sigma-Aldrich, St. Louis, Mo.), 0.08 g/g poloxamer-188, and 0.02 g/g polyethylene glycol (PEG, $M_w$=3350 Da, Product#166978, The Dow Chemical Company, Pittsburg, Calif.) is prepared by placing appropriate quantities of each component in an airtight beaker and stirring overnight.

An everolimus coating formulation containing 0.76 g/g methanol, 39.6 mg/g everolimus (Sigma-Aldrich, St. Louis, Mo.), and 0.20 g/g HYAMINE®-1622 is prepared by placing appropriate quantities of each component in an airtight beaker and stirring overnight.

An everolimus coating formulation containing 0.87 g/g methanol, 43.5 mg/g everolimus (Sigma-Aldrich, St. Louis, Mo.), 0.08 g/g poloxamer-188, and 0.02 g/g polyethylene glycol (PEG, $M_w$=3350 Da, Product#166978, The Dow Chemical Company, Pittsburg, Calif.) is prepared by placing appropriate quantities of each component in an airtight beaker and stirring overnight.

A dicumarol coating formulation containing 0.76 g/g methanol, 39.6 mg/g dicumarol (Sigma-Aldrich, St. Louis, Mo.), 0.20 g/g HYAMINE®-1622 (Product#53751, Sigma-Aldrich, St. Louis, Mo.) is prepared by placing appropriate quantities of each component in an airtight beaker and stirring overnight.

A dicumarol coating formulation containing 0.87 g/g methanol, 43.5 mg/g dicumarol (Sigma-Aldrich, St. Louis, Mo.), 0.08 g/g poloxamer-188, and 0.02 g/g polyethylene glycol (PEG, $M_w$=3350 Da, Product#166978, The Dow Chemical Company, Pittsburg, Calif.) is prepared by placing appropriate quantities of each component in an airtight beaker and stirring overnight.

A zotarolimus coating formulation containing 0.76 g/g methanol, 39.6 mg/g zotarolimus (LC Laboratories, Woburn, Mass.), 0.20 g/g HYAMINE®-1622 (Product#53751, Sigma-Aldrich, St. Louis, Mo.) is prepared by placing appropriate quantities of each component in an airtight beaker and stirring overnight.

A zotarolimus coating formulation containing 0.87 g/g methanol, 43.5 mg/g zotarolimus (LC Laboratories, Woburn, Mass.), 0.08 g/g poloxamer-188, and 0.02 g/g polyethylene glycol (PEG, $M_w$=3350 Da, Product#166978, The Dow Chemical Company, Pittsburg, Calif.) is prepared by placing appropriate quantities of each component in an airtight beaker and stirring overnight.

A docetaxel coating formulation containing 0.76 g/g methanol, 39.6 mg/g docetaxel (Sigma-Aldrich, St. Louis, Mo.), and 0.20 g/g Hyamine-1622 (Product#53751, Sigma-Aldrich, St. Louis, Mo.) is prepared by placing appropriate quantities of each component in an airtight beaker and stirring overnight.

A docetaxel coating formulation containing 0.87 g/g methanol, 43.5 mg/g docetaxel (Sigma-Aldrich, St. Louis, Mo.), 0.08 g/g poloxamer-188, and 0.02 g/g polyethylene glycol (PEG, $M_w$=3350 Da, Product#166978, The Dow Chemical Company, Pittsburg, Calif.) is prepared by placing appropriate quantities of each component in an airtight beaker and stirring overnight.

A docetaxel coating formulation containing 0.62 g/g DI water, 0.37 g/g hydroxypropyl-β-cyclodextrin (HPβCD, Sigma-Aldrich, St. Louis, Mo.), and 0.40 mg/g docetaxel (Sigma-Aldrich, St. Louis, Mo.) is prepared by placing appropriate quantities of each component in a beaker and stirring overnight at room temperature.

A docetaxel coating formulation containing 0.73 g/g methanol, 0.22 g/g hydroxypropyl-β-cyclodextrin (HPβCD, Sigma-Aldrich, St. Louis, Mo.), and 0.40 mg/g docetaxel (Sigma-Aldrich, St. Louis, Mo.) is prepared by placing appropriate quantities of each component in a beaker and stirring overnight at room temperature.

Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein. In addition to being directed to the embodiments described above and claimed below, the present invention is further directed to embodiments having different combinations of the features described above and claimed below. As such, the invention is also directed to other embodiments having any other possible combination of the dependent features claimed below.

What is claimed is:

1. A medical device comprising:
   a. an expandable member;
   b. a hydrophilic coating comprising a therapeutic agent disposed around said expandable member;
   c. a sheath disposed around said coating, wherein said sheath comprises an ePTFE material having a variably permeable microstructure comprised of nodes interconnected by fibrils, and wherein the microstructure is configured to be substantially closed when the sheath is not under a strain so as to limit unintended transfer of therapeutic agent through said sheath;
   d. wherein said sheath includes a wetting agent; and
   e. wherein the microstructure is further configured such that when said expandable member and sheath are expanded, said sheath has an open microstructure sufficient to allow fluid external to said sheath to flow through said sheath and contact said therapeutic agent.

2. The medical device of claim 1, wherein upon expansion, said sheath allows for transfer of said therapeutic agent to an area external to the sheath.

3. The medical device of claim 1, wherein the wetting agent is selected from the group consisting of heparin coatings polyvinyl alcohol, polyethylene glycol, polypropylene glycol, dextran, agarose, alginate, polyacrylamide, polyglycidol, poly(vinyl alcohol-co-ethylene), poly(ethyleneglycolco-propyleneglycol), poly(vinyl acetate-co-vinyl alcohol), poly(tetrafluoroethylene-co-vinyl alcohol), poly(acrylonitrile-co-acrylamide), poly(acrylonitrile-co-acrylic acid-co-acrylamidine), polyacrylic acid, poly-lysine, polyethyleneimine, polyvinyl pyrrolidone, polyhydroxyethylmethacrylate, and polysulfone, and their copolymers, either alone or in combination.

4. The medical device of claim 1, wherein said sheath undergoes wetting as a result of a preinsertion preparatory procedure.

5. The medical device of claim 1, wherein said medical device comprises a catheter.

6. The medical device of claim 1, wherein said sheath limits the transfer of particles out of said sheath greater than about 25 microns in size.

7. The medical device of claim 1, wherein said expandable member is a medical balloon.

8. The medical device of claim 1, wherein said sheath is configured such that it undergoes microscopic wetting in a vessel while said expandable member and sheath are in the unexpanded state.

9. The medical device of claim 1, wherein said medical device is configured such that bodily fluids substantially wet-out the sheath as said sheath is expanded.

10. The medical device of claim 1, wherein said medical device is configured such that said wetting of the sheath is facilitated when said sheath is in contact with the vessel wall.

11. The medical device of claim 1, wherein said sheath further comprises at least one material from the group consisting of a fluoropolymer, polyamides, polyurethane, polyolefins, polyesters, polyglycolic acid, poly lactic acid, and trimethylene carbonate.

12. The medical device of claim 1, wherein said nodes are aligned substantially longitudinally to the longitudinal axis of said balloon catheter and said fibrils are aligned substantially circumferentially to said axis.

13. The medical device of claim 12, wherein the sheath is configured such that a distance between said nodes increases as said outer sheath expands.

14. The medical device of claim 1, wherein said medical device is configured such that hydrophilic component in said coating raises the solubility point of a hydrophobic therapeutic agent.

15. The medical device of claim 1, wherein said coating comprises at least one compound selected from the group consisting of benzethonium chloride, PEG, poloxamer, sodium salicylate, and hydroxypropyl-β-cyclodextrin.

16. The medical device of claim 1, wherein said therapeutic agent is a hydrophilic agent.

17. The medical device of claim 1, wherein said therapeutic agent is a hydrophobic agent.

18. The medical device of claim 17, wherein hydrophobic agent is selected from the group consisting of taxane domain-binding drugs, such as paclitaxel, and rapamycin.

19. The medical device of claim 1, wherein said coating comprises benzethonium chloride and said therapeutic agent is a hydrophobic agent, wherein said hydrophobic agent is less than 40 wt % of the dry coating.

20. The medical device of claim 1, wherein said coating comprises poloxamer-188 and said therapeutic agent is a hydrophobic agent, wherein said hydrophobic agent is less than 60 wt % of the dry coating.

21. The medical device of claim 1, wherein said coating comprises poloxamer-188 and PEG and said therapeutic agent is a hydrophobic agent, wherein said hydrophobic agent is less than 50 wt % of the dry coating.

22. The medical device of claim 1, said coating comprises benzethonium chloride, and PEG and said therapeutic agent is a hydrophobic agent, wherein said PEG is less than 30 wt % of the dry coating and wherein said hydrophobic agent is less than 50 wt % of the dry coating.

23. The medical device of claim 1, wherein said coating comprises benzethonium chloride, poloxamer-188 and said therapeutic agent is a hydrophobic agent, wherein poloxamer-188 is less than 30 wt % and wherein said hydrophobic agent is less than 50 wt % of the dry coating.

24. The medical device of claim 1, wherein said coating comprises hydroxypropyl-3-cyclodextrin and said therapeutic agent is a hydrophobic agent, wherein said hydroxypropyl-3-cyclodextrin is equal to or less than 98 wt % of the dry coating.

25. The medical device of claim 1, wherein said coating comprises sodium salicylate and said therapeutic agent is a hydrophobic agent, wherein said sodium salicylate is equal to or less than 80 wt % of the dry coating.

26. The medical device of claim 1, wherein said expandable member further comprises a structural layer disposed around an outer surface of the expandable member.

27. The medical device of claim 26, wherein said coating and said therapeutic agent are disposed on said structural layer.

* * * * *